US011229855B2

(12) United States Patent
Brown et al.

(10) Patent No.: US 11,229,855 B2
(45) Date of Patent: Jan. 25, 2022

(54) CONDENSER SYSTEMS FOR PROCESSING A FLUID

(71) Applicant: LIFE TECHNOLOGIES CORPORATION, Carlsbad, CA (US)

(72) Inventors: Jason D. Brown, Logan, UT (US); Clinton C. Staheli, Brigham City, UT (US); Anthony D. Meeks, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 86 days.

(21) Appl. No.: 15/993,078

(22) Filed: May 30, 2018

(65) Prior Publication Data

US 2018/0272247 A1    Sep. 27, 2018

Related U.S. Application Data

(63) Continuation of application No. 14/588,063, filed on Dec. 31, 2014, now Pat. No. 10,005,005.
(Continued)

(51) Int. Cl.
*B01D 5/00* (2006.01)
*C12M 1/00* (2006.01)
(Continued)

(52) U.S. Cl.
CPC ............. *B01D 5/0015* (2013.01); *B01D 5/00* (2013.01); *B01D 53/002* (2013.01);
(Continued)

(58) Field of Classification Search
CPC ...... C12M 23/14; C12M 23/26; B01D 53/002; B01D 53/265; F28F 17/005; F28F 21/06; F28F 2255/02
See application file for complete search history.

(56) References Cited

U.S. PATENT DOCUMENTS 3,140,716 A   7/1964   Harrison et al.
3,212,274 A   10/1965  Eidus
(Continued)

FOREIGN PATENT DOCUMENTS

CN    2642387 Y    9/2004
CN    1649654 A    8/2005
(Continued)

OTHER PUBLICATIONS

BIOSTAT D-DCU Publication No. SB1512-e1101, Sartorius Stedim (Year: 2011).*
(Continued)

*Primary Examiner* — Eric S Ruppert
(74) *Attorney, Agent, or Firm* — Workman Nydegger

(57) ABSTRACT

A condenser system includes a collapsible container bag bounding a compartment and having an upper end and an opposing lower end, the container bag being formed of a polymeric film and being adapted to hold a fluid. A condenser bag is formed of a polymeric film and bounds a channel that extends between a first end and an opposing second end, the first end of the condenser bag being fluid coupled with the upper end of the container bag. A tubular transfer line has a first end coupled with the condenser bag at a first location so as to communicate with the channel and an opposing second end coupled with the condenser bag at a second location located between the container bag and the first location so as to communicate with the channel.

23 Claims, 27 Drawing Sheets

Related U.S. Application Data

(60) Provisional application No. 61/968,772, filed on Mar. 21, 2014.

(51) Int. Cl.
*C12M 1/06* (2006.01)
*B01D 53/26* (2006.01)
*B01D 53/00* (2006.01)

(52) U.S. Cl.
CPC .......... *B01D 53/265* (2013.01); *C12M 23/14* (2013.01); *C12M 27/02* (2013.01); *C12M 29/06* (2013.01)

(56) References Cited

U.S. PATENT DOCUMENTS

| | | | |
|---|---|---|---|
| 3,221,724 A | 12/1965 | Wentworth | |
| 3,422,887 A | 1/1969 | Berkeley | |
| 3,672,959 A | 6/1972 | Sweet | |
| 3,690,045 A | 9/1972 | Neumann | |
| 3,747,899 A * | 7/1973 | Latinen | B01F 7/02 366/168.1 |
| 3,867,260 A * | 2/1975 | Freedman | B01D 5/0003 202/185.6 |
| 4,112,829 A * | 9/1978 | Poinsard | C12F 3/02 165/111 |
| 4,177,816 A | 12/1979 | Torgeson | |
| 4,182,656 A | 1/1980 | Ahnell et al. | |
| 4,194,950 A | 3/1980 | Zalles | |
| 4,197,098 A | 4/1980 | Stiehl | |
| 4,258,784 A | 3/1981 | Perry et al. | |
| 4,309,592 A | 1/1982 | Le Boeuf | |
| 4,502,876 A | 3/1985 | Behnke, Jr. et al. | |
| 4,561,498 A | 12/1985 | Nowobilski et al. | |
| 4,573,933 A | 3/1986 | Camron | |
| 4,574,876 A | 3/1986 | Aid | |
| 4,612,086 A | 9/1986 | Dominguez | |
| 4,668,388 A | 5/1987 | Dibble et al. | |
| 4,731,072 A | 3/1988 | Aid | |
| 4,744,414 A | 5/1988 | Schon | |
| 4,797,587 A | 1/1989 | Tschudi et al. | |
| 4,910,148 A | 3/1990 | Sorensen et al. | |
| 4,935,134 A | 6/1990 | Hensgen | |
| 5,121,857 A | 6/1992 | Hutchinson | |
| 5,243,833 A | 9/1993 | Coelho et al. | |
| 5,245,693 A | 9/1993 | Ford et al. | |
| 5,271,557 A | 12/1993 | Lynch et al. | |
| 5,287,918 A | 2/1994 | Banks et al. | |
| 5,350,513 A * | 9/1994 | Markowitz | A61F 5/441 210/264 |
| 5,372,621 A | 12/1994 | Staton | |
| 5,381,510 A | 1/1995 | Ford et al. | |
| 5,411,077 A | 5/1995 | Tousignant | |
| 5,417,729 A | 5/1995 | Greenleaf, Sr. | |
| 5,443,985 A | 8/1995 | Lu et al. | |
| 5,512,141 A | 4/1996 | Koistinen et al. | |
| 5,536,475 A | 7/1996 | Moubayed et al. | |
| 5,632,793 A | 5/1997 | Haggard | |
| 5,875,282 A | 2/1999 | Jordan et al. | |
| 5,885,453 A | 3/1999 | Chatelin et al. | |
| 6,003,593 A | 12/1999 | Halligan | |
| 6,083,587 A | 7/2000 | Smith et al. | |
| 6,126,835 A | 10/2000 | Barbera-Guillem et al. | |
| 6,133,021 A | 10/2000 | Gu et al. | |
| 6,165,105 A | 12/2000 | Boutellier et al. | |
| 6,241,010 B1 | 6/2001 | Ramm-Schmidt et al. | |
| 6,391,093 B1 | 5/2002 | French | |
| 6,409,785 B1 | 6/2002 | Smithies et al. | |
| 6,432,698 B1 | 8/2002 | Gaugler et al. | |
| 6,446,463 B2 | 9/2002 | Bernini | |
| 6,490,824 B1 | 12/2002 | Maekawa et al. | |
| 6,535,689 B2 | 3/2003 | Augustine et al. | |
| 6,547,000 B1 | 4/2003 | Rantala et al. | |
| 6,619,054 B1 | 9/2003 | Cargnelli et al. | |
| 6,626,983 B1 | 9/2003 | Cairns | |
| 6,673,098 B1 | 1/2004 | Machold et al. | |
| 6,673,598 B1 | 1/2004 | Akers et al. | |
| 6,701,742 B2 | 3/2004 | Mack et al. | |
| 6,882,797 B2 | 4/2005 | Stewart et al. | |
| 6,966,974 B1 | 11/2005 | Ramm-Schmidt et al. | |
| 7,011,797 B2 | 3/2006 | Bakke | |
| 7,232,457 B2 | 6/2007 | Schmidt et al. | |
| 7,235,402 B2 | 6/2007 | Aubry | |
| 7,289,724 B2 | 10/2007 | Furnrohr et al. | |
| 7,384,783 B2 | 6/2008 | Kunas et al. | |
| 7,394,976 B2 | 7/2008 | Entenman et al. | |
| 7,487,688 B2 | 2/2009 | Goodwin | |
| 7,629,167 B2 | 12/2009 | Hodge et al. | |
| 7,682,067 B2 | 3/2010 | West et al. | |
| 7,722,839 B2 | 5/2010 | Kuzyk | |
| 7,748,438 B2 | 7/2010 | Ghelli et al. | |
| 7,819,934 B2 | 10/2010 | Galliher | |
| 7,831,318 B2 | 11/2010 | Bartee et al. | |
| 7,878,099 B2 | 2/2011 | Loibl | |
| 7,879,599 B2 | 2/2011 | Goodwin et al. | |
| 7,932,078 B2 | 4/2011 | Posseme et al. | |
| 7,955,841 B2 | 6/2011 | Belgrader et al. | |
| 8,268,059 B2 | 9/2012 | Van et al. | |
| 8,381,780 B2 | 2/2013 | Fisher et al. | |
| 8,455,242 B2 | 6/2013 | Staheli et al. | |
| 8,506,198 B2 | 8/2013 | West et al. | |
| 8,603,805 B2 | 12/2013 | Goodwin et al. | |
| 8,623,640 B2 | 1/2014 | Kunas et al. | |
| 8,641,314 B2 | 2/2014 | Thacker et al. | |
| 9,457,306 B2 | 10/2016 | Jones et al. | |
| 10,005,005 B2 | 6/2018 | Brown et al. | |
| 10,059,916 B2 | 8/2018 | Jones et al. | |
| 2001/0024820 A1 | 9/2001 | Mastromatteo et al. | |
| 2001/0039692 A1 | 11/2001 | Wright et al. | |
| 2002/0073715 A1 | 6/2002 | Logan et al. | |
| 2002/0131654 A1 | 9/2002 | Smith et al. | |
| 2002/0166656 A1 | 11/2002 | Howard et al. | |
| 2003/0077466 A1 | 4/2003 | Smith et al. | |
| 2003/0106294 A1 | 6/2003 | Chung et al. | |
| 2003/0167927 A1 | 9/2003 | Ostberg | |
| 2004/0062140 A1 | 4/2004 | Cadogan et al. | |
| 2004/0149127 A1 | 8/2004 | Lyons | |
| 2004/0209331 A1 | 10/2004 | Ririe | |
| 2005/0239198 A1 | 10/2005 | Kunas et al. | |
| 2005/0272146 A1 | 12/2005 | Hodge et al. | |
| 2005/0279125 A1 | 12/2005 | Operschall | |
| 2005/0287660 A1 * | 12/2005 | Aubry | C12M 41/34 435/297.1 |
| 2006/0196501 A1 | 9/2006 | Bibbo et al. | |
| 2006/0240546 A1 | 10/2006 | Goodwin et al. | |
| 2006/0270036 A1 | 11/2006 | Goodwin et al. | |
| 2006/0275894 A1 | 12/2006 | Felder et al. | |
| 2006/0279167 A1 | 12/2006 | Turner | |
| 2007/0175831 A1 | 8/2007 | Almaasbak et al. | |
| 2007/0199890 A1 | 8/2007 | Trogolo | |
| 2007/0275452 A1 | 11/2007 | Yamasaki et al. | |
| 2008/0016059 A1 | 1/2008 | Henkin et al. | |
| 2008/0060216 A1 | 3/2008 | Reilly | |
| 2008/0068920 A1 | 3/2008 | Galliher et al. | |
| 2008/0127832 A1 | 6/2008 | Zhang | |
| 2008/0160591 A1 | 7/2008 | Willson et al. | |
| 2008/0272146 A1 | 12/2008 | Hodge et al. | |
| 2009/0035856 A1 | 2/2009 | Galliher et al. | |
| 2009/0081742 A1 | 3/2009 | Dunlop et al. | |
| 2009/0087903 A1 | 4/2009 | Belgrader et al. | |
| 2009/0119869 A1 | 5/2009 | Yoo | |
| 2009/0148143 A9 | 6/2009 | Entenman et al. | |
| 2009/0155885 A1 | 6/2009 | Bartsch | |
| 2009/0233334 A1 | 9/2009 | Hildinger et al. | |
| 2010/0075405 A1 | 3/2010 | Broadley et al. | |
| 2010/0124564 A1 | 5/2010 | Martinson et al. | |
| 2010/0151558 A1 | 6/2010 | Alianell et al. | |
| 2010/0170400 A1 * | 7/2010 | van den Boogard | C12M 29/20 96/221 |
| 2010/0229296 A1 | 9/2010 | Samuel | |
| 2010/0237009 A1 | 9/2010 | Horst | |
| 2010/0248333 A1 | 9/2010 | Bartilson | |
| 2011/0003355 A1 | 1/2011 | Clark et al. | |

(56) References Cited

U.S. PATENT DOCUMENTS

| | | |
|---|---|---|
| 2011/0046551 A1 | 2/2011 | Augustine et al. |
| 2011/0076759 A1 | 3/2011 | Reif et al. |
| 2011/0124087 A1 | 5/2011 | Meiser et al. |
| 2011/0188928 A1 | 8/2011 | West et al. |
| 2011/0198066 A1 | 8/2011 | Starbard |
| 2011/0198286 A1 | 8/2011 | Niazi |
| 2011/0207170 A1 | 8/2011 | Niazi |
| 2011/0207218 A1 | 8/2011 | Staheli et al. |
| 2011/0258975 A1 | 10/2011 | Lundgren |
| 2011/0310696 A1 | 12/2011 | Goodwin et al. |
| 2012/0094785 A1 | 4/2012 | Cheng et al. |
| 2012/0103579 A1* | 5/2012 | Reif .................. F28D 9/005 165/167 |
| 2012/0132548 A1 | 5/2012 | Galliher et al. |
| 2012/0177533 A1 | 7/2012 | Lee et al. |
| 2012/0260671 A1* | 10/2012 | Damren ............... B01D 5/0093 62/3.4 |
| 2013/0067721 A1 | 3/2013 | Scannon et al. |
| 2013/0082410 A1 | 4/2013 | Goodwin et al. |
| 2013/0089925 A1 | 4/2013 | Damren et al. |
| 2013/0101982 A1 | 4/2013 | Goodwin et al. |
| 2013/0260463 A1 | 10/2013 | Staheli et al. |
| 2014/0106453 A1 | 4/2014 | Kunas et al. |
| 2014/0251322 A1* | 9/2014 | Miller ............... A61M 16/0057 128/201.13 |
| 2014/0298612 A1 | 10/2014 | Williams et al. |
| 2015/0265943 A1 | 9/2015 | Brown et al. |
| 2015/0265958 A1 | 9/2015 | Brown et al. |

FOREIGN PATENT DOCUMENTS

| | | | |
|---|---|---|---|
| CN | 201276562 Y | 7/2009 | |
| CN | 201396935 Y | 2/2010 | |
| CN | 202129073 U | 2/2012 | |
| CN | 102711969 A | 10/2012 | |
| CN | 103458982 A | 12/2013 | |
| DE | 20004438 U1 | 6/2000 | |
| DE | 69801982 T2 | 4/2002 | |
| DE | 69813252 T2 | 5/2004 | |
| DE | 102006013271 A1 | 9/2007 | |
| DE | 20 2009 006 839 U1 | 8/2009 | |
| DE | 10 2008 027 638 A1 | 12/2009 | |
| DE | 102009003972 A1 | 7/2010 | |
| EP | 0003774 A1 * | 9/1979 | .......... C07C 309/00 |
| EP | 0 073 079 B1 | 3/1986 | |
| EP | 0 400 829 A1 | 12/1990 | |
| EP | 0471947 A1 | 2/1992 | |
| EP | 0639096 A1 | 2/1995 | |
| EP | 1132695 A1 | 9/2001 | |
| EP | 1222433 A1 | 7/2002 | |
| EP | 1676623 A1 | 7/2006 | |
| EP | 1 837 640 A2 | 9/2007 | |
| EP | 1916488 A1 | 4/2008 | |
| EP | 1 950 281 A1 | 7/2008 | |
| EP | 2 065 085 A1 | 6/2009 | |
| EP | 2 123 745 A2 | 11/2009 | |
| EP | 2195412 A2 | 6/2010 | |
| EP | 2297292 A2 | 3/2011 | |
| EP | 2483614 A1 | 8/2012 | |
| GB | 2491623 A | 12/2012 | |
| GB | 2496141 A | 5/2013 | |
| JP | 58-47485 A | 3/1983 | |
| JP | 59-042884 A | 3/1984 | |
| JP | 60-183003 A | 9/1985 | |
| JP | 61-149080 A | 7/1986 | |
| JP | 3-196836 | 8/1991 | |
| JP | H04-118015 | 4/1992 | |
| JP | H04-122618 | 11/1992 | |
| JP | 05-168463 A | 7/1993 | |
| JP | 08-70845 A | 3/1996 | |
| JP | 8-501927 | 3/1996 | |
| JP | 9-14837 | 1/1997 | |
| JP | 09-014937 A | 1/1997 | |
| JP | H10-505542 | 6/1998 | |
| JP | 10-216466 A | 8/1998 | |
| JP | H10-216446 | 8/1998 | |
| JP | 11-512968 A | 11/1999 | |
| JP | H11-333239 | 12/1999 | |
| JP | 2002-3505 | 1/2002 | |
| JP | 2003-305134 A | 10/2003 | |
| JP | 2004-271031 | 9/2004 | |
| JP | 2007-534335 | 11/2007 | |
| JP | 2009-50838 | 3/2009 | |
| JP | 2009-539408 | 11/2009 | |
| JP | 2009-291192 | 12/2009 | |
| JP | 4809903 B2 | 11/2011 | |
| JP | 2012170364 A * | 9/2012 | .......... C12M 27/02 |
| JP | 2013-520299 A | 6/2013 | |
| KR | 101152862 B1 * | 6/2012 | |
| TW | 200906503 A | 2/2009 | |
| WO | 92/10265 A1 | 6/1992 | |
| WO | 94/01530 | 1/1994 | |
| WO | 01/27551 A1 | 4/2001 | |
| WO | 2003/092849 A1 | 11/2003 | |
| WO | 2006/116139 | 11/2006 | |
| WO | 2007/042331 A1 | 4/2007 | |
| WO | 2009/034439 A2 | 3/2009 | |
| WO | 2009/093995 A1 | 7/2009 | |
| WO | 2009/146769 A | 12/2009 | |
| WO | 2010/068912 A2 | 6/2010 | |
| WO | 2011/041508 A1 | 4/2011 | |
| WO | 2011/078773 A1 | 6/2011 | |
| WO | 2011/102931 A2 | 8/2011 | |
| WO | 2011/110726 A1 | 9/2011 | |
| WO | 2012/170878 A2 | 12/2012 | |
| WO | 2013/009668 A2 | 1/2013 | |
| WO | 2013/032392 A1 | 3/2013 | |
| WO | 2013/053779 A1 | 4/2013 | |
| WO | 2015/142406 A1 | 9/2015 | |

OTHER PUBLICATIONS

BIOSTAT D-DCU, Your "Fast Lane" to Production, Sartorius Stedim.*

G. Catapano et al., *Bioreactor Design and Scale Up*, Chapter 5 of Cell and Tissue Reaction Engineering, 2009, pp. 173-259.

Minghui Hu et al., *Study of an Efficient Temperature Measurement for an Industrial Bioreactor*, ScienceDirect, Measure, vol. 44, 2011, pp. 875-880.

Zhiwei Zhou et al., *Optimizing of Bioreactor Heat Supply and Material Feeding by Numberical Calculation*, ICICIS, 2011, pp. 195-202.

Discovery Scientific Product Lines, Discovery Scientific, http://discoveryscientific.com/products-by-type2/b/mammalian-insect-cell-culture-bioreactor, Apr. 25, 2014, 3 pages.

DASbox Single-Use Vessel, Brochure, DASGIP Information and Process Technology, GMBH, 2012, 2 pages.

European Search Report dated Dec. 13, 2017, issued in EP Application No. 17193579.4, filed Sep. 27, 2017.

Extended European Search Report dated Aug. 14, 2014, issued in EP Application No. 14173779.1, filed Jun. 24, 2014.

International Search Report and Written Opinion dated Jan. 5, 2016, issued in PCT Application No. PCT/US2015/054241, filed Oct. 6, 2015.

International Search Report and Written Opinion dated Jun. 29, 2015, issued in PCT Application No. PCT/US2014/073067, filed Dec. 31, 2014.

International Search Report dated May 17, 2011, issued in PCT Application No. PCT/US2011/021714, filed Jan. 19, 2011.

Partial International Search Report dated Mar. 30, 2015, issued in PCT Application No. PCT/US2014/073067, filed Dec. 31, 2014.

* cited by examiner

CONDENSER SYSTEMS FOR PROCESSING A FLUID

CROSS-REFERENCE TO RELATED APPLICATIONS

This application is a continuation of U.S. application Ser. No. 14/588,063, filed Dec. 31, 2014, which claims the benefit of U.S. Provisional Application No. 61/968,772, filed Mar. 21, 2014, which are incorporated herein by specific reference.

BACKGROUND OF THE INVENTION

1. The Field of the Invention

The present invention relates to condenser systems that can be used for processing a fluid, such as a cell culture.

2. The Relevant Technology

Bioreactors are used in the growth of cells and microorganisms. A typical bioreactor includes a container which holds a suspension comprised of liquid growth media, a culture of cells or microorganisms, and other desired nutrients and components. A rotatable impeller is operated within the suspension to maintain the suspension in a substantially homogenous state. Small gas bubbles are continuously sparged into the suspension and are typically used to help oxygenate the culture, strip out unwanted $CO_2$ from the suspension and control the pH of the suspension.

To maintain the viability of the culture, the compartment in which the culture is being grown must remain sterile. To remove the sparged gas that is being continuously added to the suspension while maintaining sterility of the compartment, the gas is typically removed through a filter system. One conventional filter system is referred to as a cartridge filter system and includes a rigid, metal housing into which a cartridge filter is removably positioned. Gas from the container is delivered to an inlet on the housing. The gas then travels through the filter within the housing and is then expelled to the environment through an outlet on the housing. The filter prevents any biological matter within the container from being expelled into the environment and prevents any contaminates in the environment from entering into the container.

Although useful, the conventional cartridge filter system has a number of shortcomings. For example, the metal housing in which the cartridge filter is placed is time consuming and labor intensive to maintain because it must be cleaned and sterilized between each use. Cleaning the metal housing can introduce chemical contaminants and leave production residuals. Furthermore, in addition to being expensive to purchase, the metal housing is cumbersome, both because it is a stand-alone item that occupies substantial space around the bioreactor and because it requires a relatively long length of tubing that must be run from the container and then sterilely connected to the housing. In addition, because the filter slowly clogs during use, the problems are compounded because multiple filter housings must be connected in parallel to ensure that the process can be continuously operated until the culture is fully grown.

In one attempt to address some of the above shortcomings, capsule filters have also been used with bioreactors. A capsule filter comprises a rigid plastic housing that permanently encases a filter. Although capsule filters are disposable and thus do not need to be cleaned or sterilized, they have their own drawbacks. For example, capsule filters are designed to be capable of operating at relatively high pressures and are typically rated for about 500 kPa. To enable operation at this pressure, the plastic housing is required to be relatively thick, thereby increasing the expense to the filter and making it relatively large and bulky. Furthermore, the capsule filters have a relatively small inlet and outlet port through which the gas travels. As a result of the small diameter ports, if a large gas flow rate is being processed, the system must either be operated at a high gas pressure, which can be undesirable in some circumstances, or multiple filters must be used, which increases cost and complexity.

The sparge gas passing through the suspension will carry moisture toward the filter assembly. Moisture that condenses on the filters will clog the filters. To limit the rate at which the filters are clogged, a condenser system can be placed between the reactor container and the filter system. The condenser system removes a portion of the moisture from the gas before it reaches the filter system. Traditional condenser systems, however, are often inconvenient to use in that they are typically complex, stand-alone systems that require multiple tubes that need sterile connections with the container and filter assembly. Furthermore, the condenser systems typically restrict the gas flow rate and thereby require that the system be operated at an elevated pressure. Condenser system can also be difficult to adjust for different gas flow rates.

Accordingly, what is needed in the art are condenser systems and filtration systems that can be used with bioreactors and other fluid processing systems that solve some or all of the above problems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
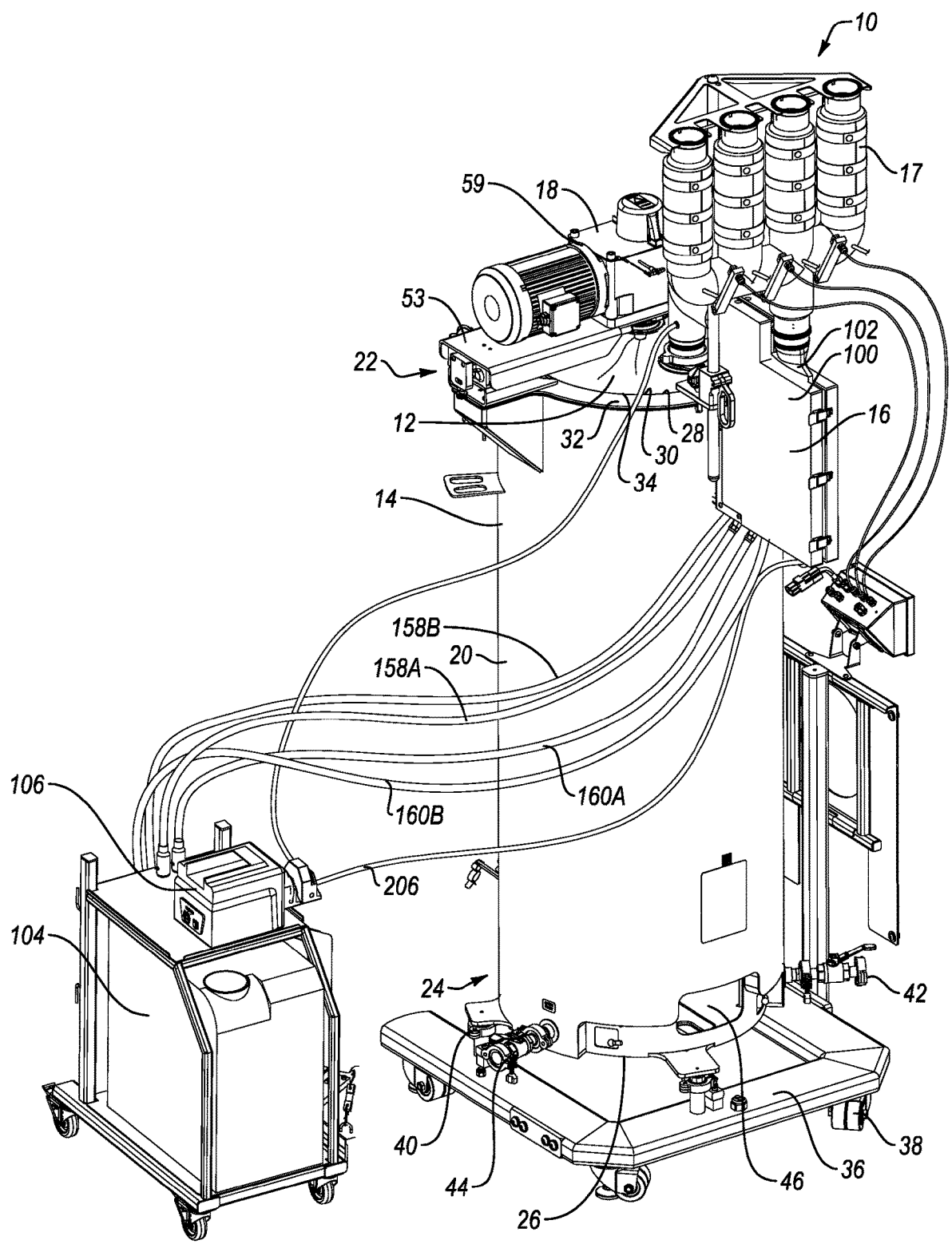
FIG. 1 is a perspective view of a fluid processing system including a condenser system and a filter system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present invention, and is not intended to limit the scope of the invention in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," "having" or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

Where possible, like numbering of elements have been used in various figures. Furthermore, multiple instances of an element and or sub-elements of a parent element may each include separate letters appended to the element number. For example two instances of a particular element "91" may be labeled as "91a" and "91b". In that case, the element label may be used without an appended letter (e.g., "91") to generally refer to instances of the element or any one of the elements. Element labels including an appended letter (e.g., "91a") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12a" and "12b."

Various aspects of the present devices and systems may be illustrated by describing components that are coupled, attached, and/or joined together. As used herein, the terms "coupled", "attached", "connected" and/or "joined" are used to indicate either a direct connection between two components or, where appropriate, an indirect connection to one another through intervening or intermediate components. In contrast, when a component is referred to as being "directly coupled", "directly attached", "directly connected" and/or "directly joined" to another component, there are no intervening elements present.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

The present invention relates to condenser systems, filter systems and to processing systems and methods for mixing and sparging solutions and/or suspensions that incorporate such condenser systems and filter systems. The processing systems can be bioreactors or fermenters used for culturing cells or microorganisms. By way of example and not by limitation, the inventive systems can be used in culturing bacteria, fungi, algae, plant cells, animal cells, protozoans, nematodes, and the like. The systems can accommodate cells and microorganisms that are aerobic or anaerobic and are adherent or non-adherent. The systems can also be used in association with the formation and/or treatment of solutions and/or suspensions that are not biological but nevertheless incorporate mixing and sparging. For example, the systems can be used in the production of media, chemicals, food products, beverages, and other liquid products which require sparging with a gas.

The inventive systems are designed so that a majority of the system components that contact the material being processed can be disposed of after each use. As a result, the inventive systems substantially eliminate the burden of cleaning and sterilization required by conventional stainless steel mixing and processing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Depicted in FIG. 1 is one embodiment of an inventive fluid processing system 10 incorporating features of the present invention. In general, processing system 10 comprises a container 12 that is disposed within a rigid support housing 14 and that is coupled with a condenser system 16. A filter system 17 is coupled with condenser system 16 and functions to both filter gas exiting from condenser system 17 and prevent contaminates from entering container 12. A mixer system 18 is designed for mixing and/or suspending components within container 12. The various components of fluid processing system 10 will now be discussed in greater detail.

With continued reference to FIG. 1, support housing 14 has a substantially cylindrical sidewall 20 that extends between an upper end 22 and an opposing lower end 24. Lower end 24 has a floor 26 mounted thereto. Support housing 14 has an interior surface 28 that bounds a chamber 30. An annular lip 32 is formed at upper end 22 and bounds an opening 34 to chamber 30. Floor 26 of support housing 14 rests on a cart 36 having wheels 38. Support housing 14 is removable secured to cart 36 by connectors 40. Cart 36 enables selective movement and positioning of support housing 14. In alternative embodiments, however, support housing 14 need not rest on cart 36 but can rest directly on a floor or other structure.

Although support housing 14 is shown as having a substantially cylindrical configuration, in alternative embodiments support housing 14 can have any desired shape capable of at least partially bounding a compartment. For example, sidewall 20 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 30 can hold a volume of less than 50 liters or more than 1,000 liters. Support housing 14 is typically made of metal, such as stainless steel, but can also be made of other materials capable of withstanding the applied loads of the present invention.

In one embodiment of the present invention means are provided for regulating the temperature of the fluid that is contained within container 12 disposed within support housing 14. By way of example and not by limitation, electrical heating elements can be mounted on or within support housing 14. The heat from the heating elements is transferred either directly or indirectly to container 12. Alternatively, in the depicted embodiment support housing 14 is jacketed with one or more fluid channels being formed therein. The fluid channels have a fluid inlet 42 and a fluid outlet 44 that enables a fluid, such as water or propylene glycol, to be pumped through the fluid channels. By heating, cooling or otherwise controlling the temperature of the fluid that is passed through the fluid channels, the temperature of support housing 14 can be regulated which in turn regulates the temperature of the fluid within container 12 when container 12 is disposed within support housing 14. Other conventional means can also be used such as by applying gas burners to support housing 14 or pumping the fluid out of container 12, heating or cooling the fluid and then pumping the fluid back into container 12. When using container 12 as part of a bioreactor or fermenter, the means for heating can be used to heat the culture within container 12 to a temperature in a range between about 30° C. to about 40° C. Other temperatures can also be used.

Support housing 14 can have one or more opening 46 formed on the lower end of sidewall 20 and on floor 26 to enable gas and fluid lines to couple with container 12 and to enable various probes and sensors to couple with container 12 when container 12 is within support housing 14. Further disclosure on support housing 14 and alternative designs thereof is disclosed in U.S. Pat. No. 7,682,067 and US Patent Publication No. 2011-0310696, which are incorporated herein by specific reference.

Figure 2:
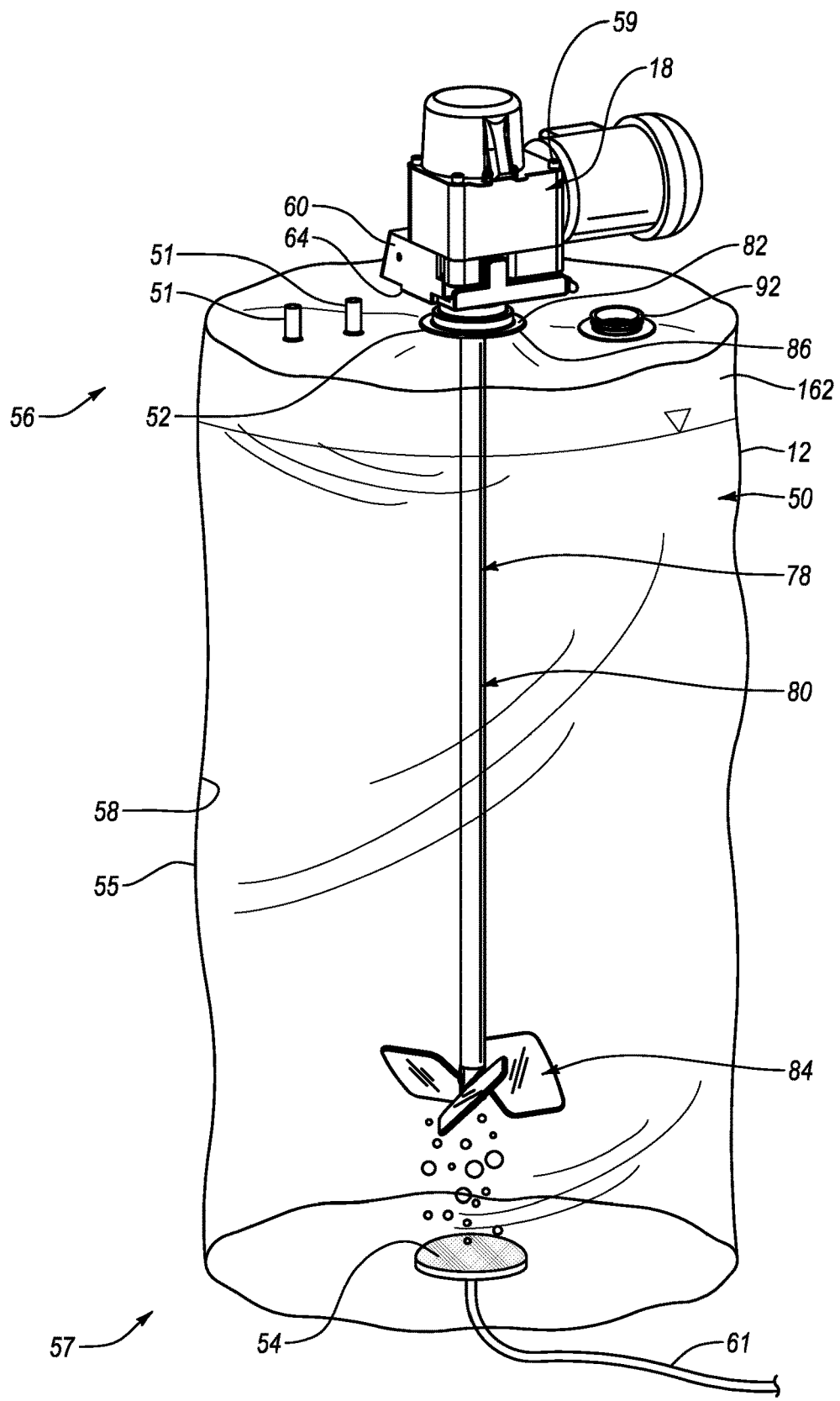
FIG. 2 is a perspective view of a container of the system shown in FIG. 1 with a mixing system.

FIG. 2 shows container 12 coupled with mixer system 18. Container 12 has a side 55 that extends from an upper end 56 to an opposing lower end 57. Container 12 also has an interior surface 58 that bounds a compartment 50 in which a portion of mixer system 18 is disposed. In the embodiment depicted, container 12 comprises a flexible bag and is also referred to herein as a container bag. Formed on container 12 are a plurality of ports 51 that communicate with compartment 50. Although only two ports 51 are shown, it is appreciated that container 12 can be formed with any desired number of ports 51 and that ports 51 can be formed at any desired location on container 12 such as upper end 56, lower end 57, and/or alongside 55. Ports 51 can be the same configuration or different configurations and can be used for a variety of different purposes. For example, ports 51 can be coupled with fluid lines for delivering media, cell cultures, and/or other components into and out of container 12.

Ports 51 can also be used for coupling probes to container 12. For example, when container 12 is used as a bioreactor for growing cells or microorganisms, ports 51 can be used for coupling probes such as temperatures probes, pH probes, dissolved oxygen probes, and the like. Examples of ports 51 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 51 can also be used for coupling container 12 to secondary containers and to other desired fittings.

Figure 11:
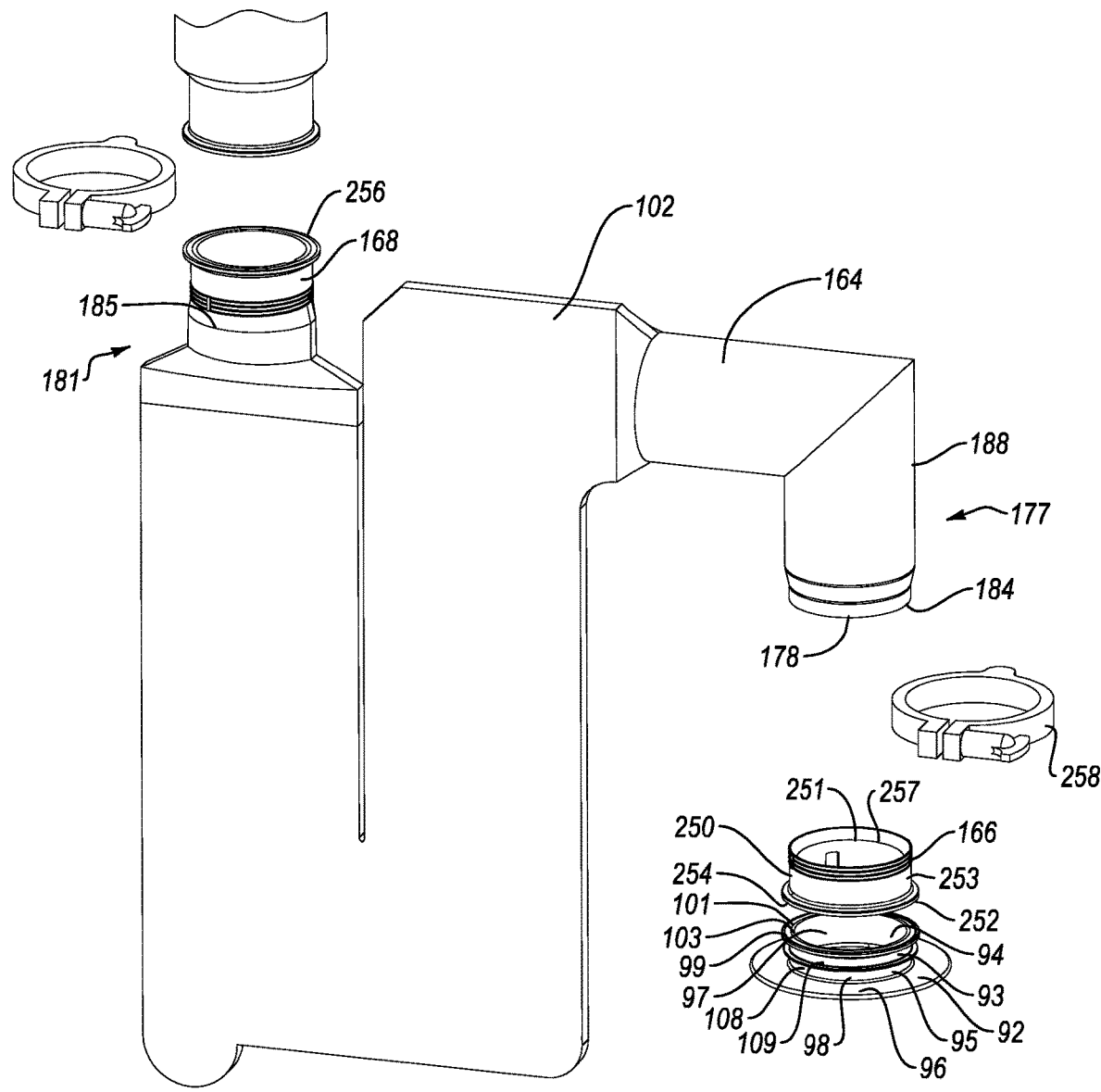
FIG. 11 is a partially exploded view of the condenser bag shown in FIG. 10 with ports that can be coupled therewith.

As also depicted in FIG. 2, an exhaust port 92 is mounted on upper end 56 of container 12 and is used for coupling with condenser system 16. As depicted in FIG. 11, exhaust port 92 includes a stem 93 having an interior surface 94 and an opposing exterior surface 95 that extend between a first end and an opposing second end. Encircling and radially outwardly projecting from the first end is a mounting flange 96. Mounting flange 96 is welded or otherwise secured to interior surface 58 of container 12 (FIG. 2) so that stem 93 projects out through an opening on container 12. Interior surface 58 bounds a port opening 97 that extends through stem 93 and communicates with compartment 50 of container 12. In the depicted embodiment, port opening 97 has a circular transverse cross section. Other configurations can also be used such as elliptical, polygonal, irregular or the like. The transverse cross section of port opening 97 typically has a maximum diameter in a range between about 0.5 cm to about 15 cm with about 2 cm to about 10 cm being more common. For high gas throughput, the maximum diameter is typically greater than 3 cm, 4 cm, 5 cm or 6 cm. Other dimensions can also be used depending on the application.

Encircling and outwardly projecting from exterior surface 95 of stem 93 at a location between the opposing ends is a retention flange 98. Encircling and outwardly projecting from the second end of stem 93 is a coupling flange 99. Coupling flange 99 has a top surface 101 with an annular seal 103 formed thereon. A first annular groove 108 is formed between mounting flange 96 and retention flange 98 while a second annular groove 109 is formed between retention flange 98 and coupling flange 99. The body of exhaust port 92 is typically molded from a polymeric material and is more rigid than container 12. Annular seal 103 is typically formed from an elastomeric material that is more flexible than the port body on which it is attached. The use of exhaust port 92 will be discussed below in greater detail.

In one embodiment of the present invention, means are provided for delivering a gas into the lower end of container 12. By way of example and not by limitation, as also depicted in FIG. 2, a sparger 54 can be either positioned on or mounted to lower end 57 of container 12 for delivering a gas to the fluid within container 12. As is understood by those skilled in the art, various gases are typically required in the growth of cells or microorganisms within container 12. The gas typically comprises air that is selectively combined with oxygen, carbon dioxide and/or nitrogen. However, other gases can also be used. The addition of these gases can be used to regulate the dissolved oxygen and $CO_2$ content and to regulate the pH of a culture solution. Depending on the application, sparging with gas can also have other applications. A gas line 61 is coupled with sparger 54 for delivering the desired gas to sparger 54. Gas line 61 need not pass through lower end 57 of container 12 but can extend down from upper end 56 or from other locations.

Sparger 54 can have a variety of different configurations. For example, sparger 54 can comprise a permeable membrane or a fritted structure comprised of metal, plastic or other materials that dispense the gas in small bubbles into container 12. Smaller bubbles can permit better absorption of the gas into the fluid. In other embodiments, sparger 54 can simply comprise a tube, port, or other type opening formed on or coupled with container 12 through which gas is passed into container 12. In contrast to being disposed on container 12, the sparger can also be formed on or coupled with mixer system 18. Examples of spargers and how they can be used in the present invention are disclosed in United States Patent Publication Nos. 2006-0270036 and 2006-0240546 which were previously incorporated by reference. Other conventional spargers can also be used.

In the depicted embodiment, container 12 has an opening 52 that is sealed to a rotational assembly 82 of mixer system 18, which will be discussed below in greater detail. As a result, compartment 50 is sealed closed so that it can be sterilized and be used in processing sterile fluids. During use, container 12 is disposed within chamber 30 of support housing 14 as depicted in FIG. 1. Container 12 is supported by support housing 14 during use and can subsequently be disposed of following use. In one embodiment, container 12 comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween.

The material is approved for direct contact with living cells and is capable of maintaining a solution sterile. In such an embodiment, the material can also be sterilizable such as by radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 12 comprises a two-dimensional pillow style bag wherein two sheets of material are placed in overlapping relation and the two sheets are bounded together at their peripheries to form the internal compartment. Alternatively, a single sheet of material can be folded over and seamed around the periphery to form the internal compartment. In another embodiment, the containers can be formed from a continuous tubular extrusion of polymeric material that is cut to length and is seamed closed at the ends.

In still other embodiments, container 12 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002, which is hereby incorporated by reference.

It is appreciated that container 12 can be manufactured to have virtually any desired size, shape, and configuration. For example, container 12 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 12 can be any shape, in one embodiment container 12 is specifically configured to be complementary or substantially complementary to chamber 30 of support housing 14. It is desirable that when container 12 is received within chamber 30, container 12 is at least generally uniformly supported by support housing 14. Having at least general uniform support of container 12 by support housing 14 helps to preclude failure of container 12 by hydraulic forces applied to container 12 when filled with fluid.

Although in the above discussed embodiment container 12 has a flexible, bag-like configuration, in alternative embodiments it is appreciated that container 12 can comprise any form of collapsible container or semi-rigid container. Container 12 can also be transparent or opaque and can have ultraviolet light inhibitors incorporated therein.

Mixer system 18 is used for mixing and/or suspending a culture or other solution within container 12. As depicted in FIG. 2, mixer system 18 generally comprises a drive motor assembly 59 that is mounted on support housing 14 (FIG. 1), a impeller assembly 78 coupled to and projects into container 12, and a drive shaft 72 (FIG. 4) that extends between drive motor assembly 59 and impeller assembly 78.

Figure 3:
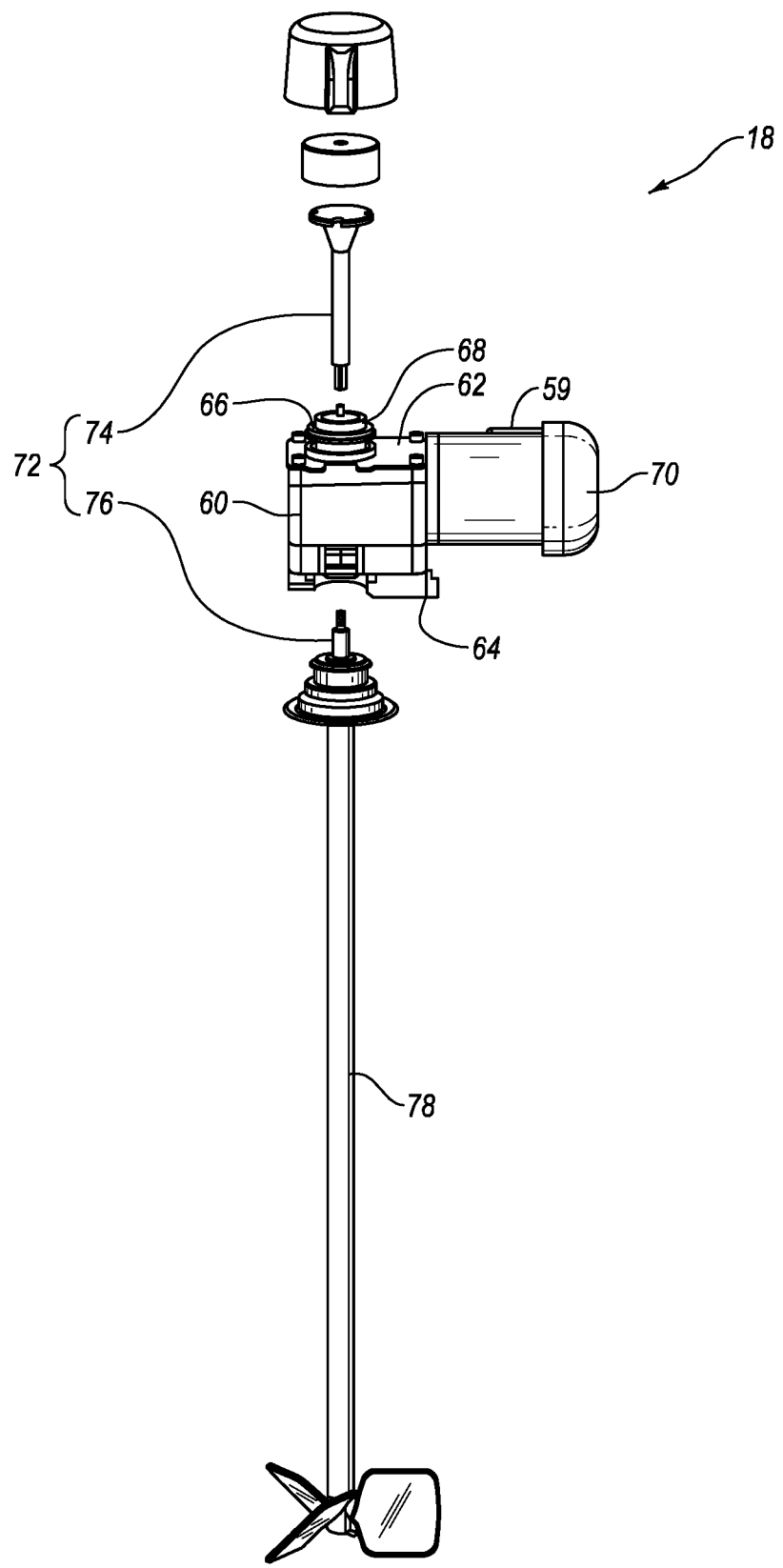
FIG. 3 is a partially exploded view of the mixer system shown in FIG. 2.

Turning to FIG. 3, drive motor assembly 59 comprises a housing 60 having a top surface 62 and an opposing bottom surface 64 with an opening 66 extending through housing 60 between surfaces 62 and 64. A tubular motor mount 68 is rotatably secured within opening 66 of housing 60. A drive motor 70 is mounted to housing 60 and engages with motor mount 68 so as to facilitate select rotation of motor mount 68 relative to housing 60. As depicted in FIG. 1, drive motor assembly 59 is coupled with support housing 14 by a bracket 53. In alternative embodiments, however, drive motor assembly 59 can be mounted on a separate structure adjacent to support housing 14.

Figure 4:
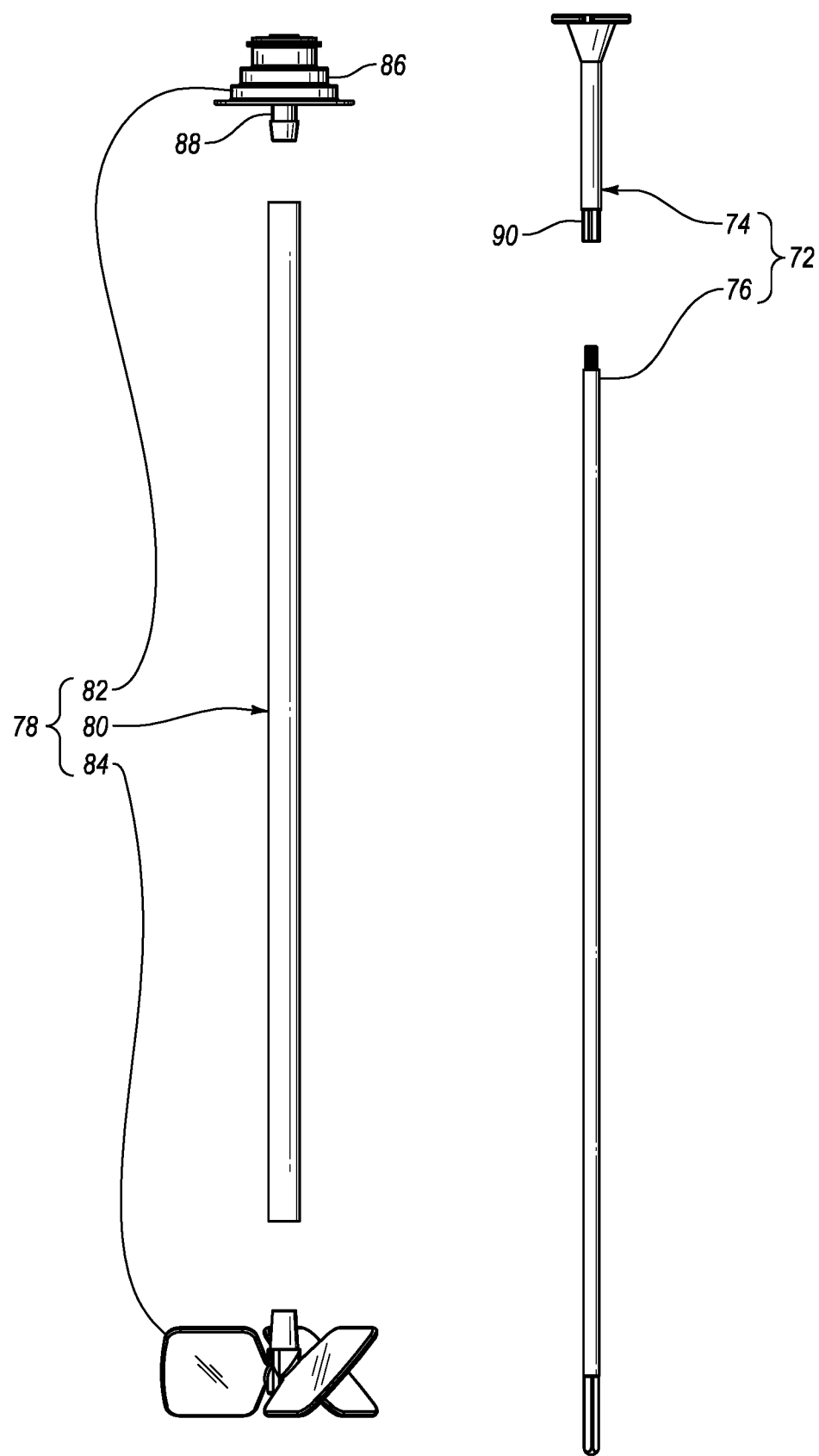
FIG. 4 is an exploded view of an impeller assembly and drive shaft of the mixing system shown in FIG. 3.

Drive shaft 72 is configured to pass through motor mount 68 and thus through housing 60. Turning to FIG. 4, drive shaft 72 comprises a head section 74 and a shaft section 76 that are either connected together or integrally formed as a single piece. Impeller assembly 78 comprises an elongated tubular connector 80 having rotational assembly 82 secured at one end and an impeller 84 secured to the opposing end. Rotational assembly 82 comprises an outer casing 86 and a tubular hub 88 that centrally extends through outer casing 86 and is rotatably coupled thereto. One or more dynamic seals can be formed between outer casing 86 and tubular hub 88 so that a sterile seal can be maintained therebetween. As depicted in FIG. 2, outer casing 86 is secured to container 12 so that tubular connector 80, which is coupled with hub 88, extends into compartment 50 of container 12. Impeller 84, which is disposed on the end of connector 80, is also disposed within compartment 50 of container 12.

During use, container 12 with impeller assembly 78 secured thereto are positioned within chamber 30 of support housing 14. Rotational assembly 82 is then removably connected to bottom surface 64 of housing 60 of drive motor assembly 59 so that hub 88 is aligned with motor mount 68. The distal end of drive shaft 72 is advanced down through motor mount 68, through hub 86 of rotational assembly 82, and through tubular connector 80. Finally, the distal end of drive shaft 72 is received within a socket on impeller 84 so that rotation of drive shaft 72 facilitates rotation of impeller 84.

With drive shaft 72 engaging impeller 84, a driver portion 90 (FIG. 4) of drive shaft 72 is received within and engages hub 88 so that rotation of draft shaft 72 also rotates hub 88. Because outer casing 86 is secured to housing 60, hub 88 rotates relative to casing 86 and housing 60 as drive shaft 72 is rotated. It is further noted that tubular connector 80 also rotates concurrently with impeller 84, hub 88 and drive shaft 72.

Finally, once drive shaft 72 is fully passed through motor mount 68, head section 74 of drive shaft 72 engages motor mount 68. Accordingly, as motor 70 facilitates rotation of motor mount 68, motor mount 68 facilitates rotation of drive shaft 72. In turn, as discussed above, drive shaft 72 facilitates rotation of hub 88, connector 80 and impeller 84. Rotation of impeller 84 facilities mixing and suspension of the fluid within compartment 50 of container 12. Further disclosure with regard to mixer system 18, the operation thereof, and alternative embodiments thereof are disclosed in United States Patent Publication No. 2011-0188928 A1, published Aug. 4, 2011, which is incorporated herein by specific reference.

The above described mixer system 18 and the alternatives thereto comprise one embodiment of means for mixing fluid contained within container 12. In alternative embodiments, it is appreciated that mixer system 18 can be replaced with a variety of other mixing systems. For example, mixer system 18 can be replaced with a conventional rigid drive shaft that projects into container 12 through a dynamic seal and has an impeller or other mixing element mounted on the end thereof. External rotation of the drive shaft thus facilitates rotation of the impeller or other mixing element which mixes and/or suspends the fluid within container 12.

In another embodiment, the drive shaft projecting into container 12 can be configured to repeatedly rise and lower a mixing element located within container 12 for mixing the fluid. Alternatively, a magnetic stir bar can be disposed within compartment 50 of container 12 and rotated by a magnetic mixer disposed outside of container 12. In yet other embodiments, a stir bar, paddle, or the like that projects into compartment 50 of container 12 can be pivoted, swirled or otherwise moved to mix the fluid. In addition, the mixing can be accomplished by circulating fluid through compartment 50, such as by using a peristaltic pump to move the fluid into and out of compartment 50 through a tube having opposing ends sealed to container 12. Gas bubbles can also be passed through the fluid to achieve the desired mixing. Finally, support housing 14 and container 12 can be pivoted, rocked, rotated or otherwise moved so as to mix the fluid within container 12. Other conventional mixing techniques can also be used. Specific examples of how to incorporate a mixer into a flexible bag, such as container 12, are disclosed in U.S. Pat. No. 7,384,783, issued Jun. 10, 2008; U.S. Pat. No. 7,682,067, issued Mar. 23, 2010; and US Patent Publication No. 2006/0196501, published Sep. 7, 2006 which are incorporated herein by specific reference.

Figure 5:
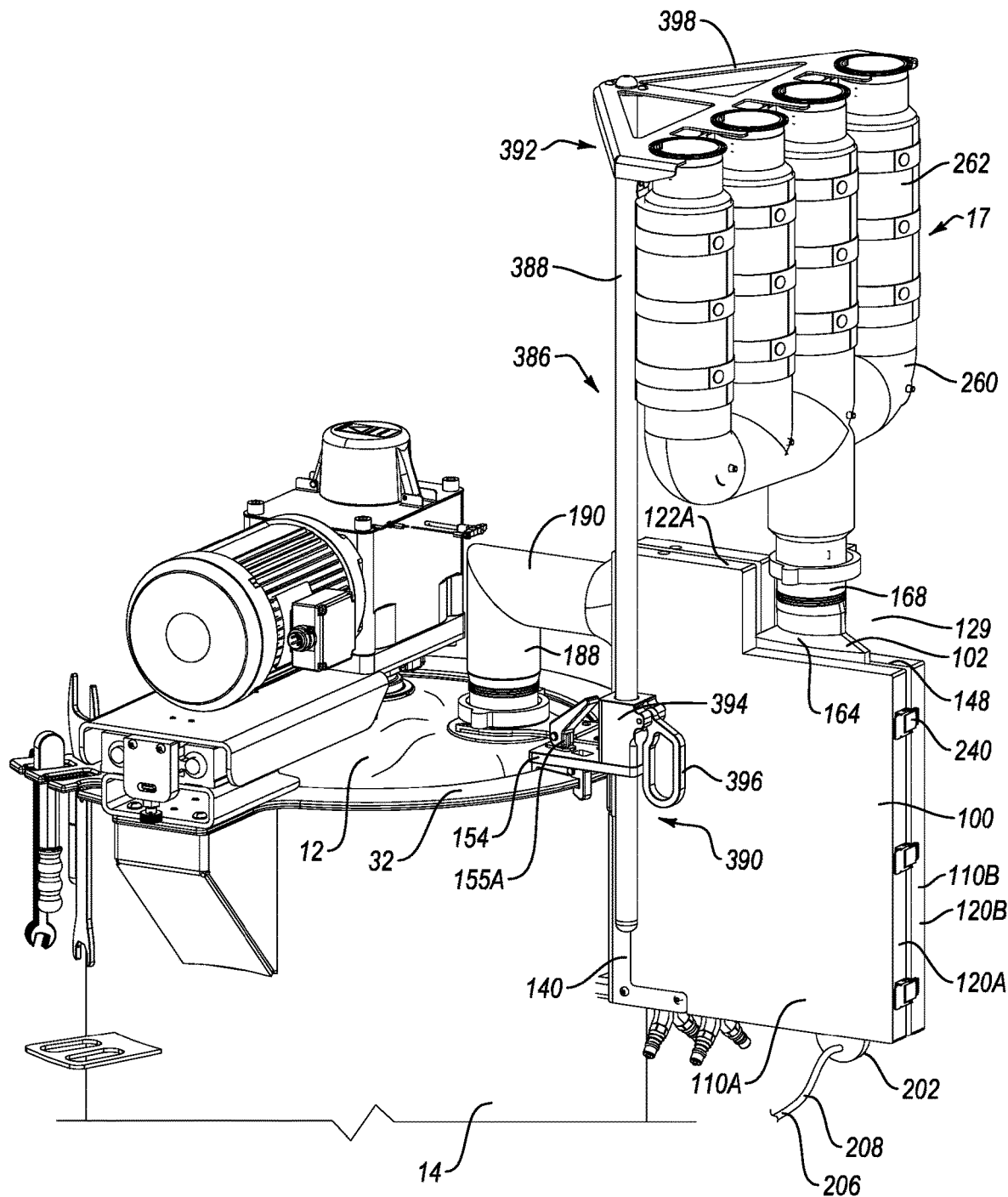
FIG. 5 is an enlarged perspective view of portions of the condenser system and filter system shown in FIG. 1.
Figure 6:
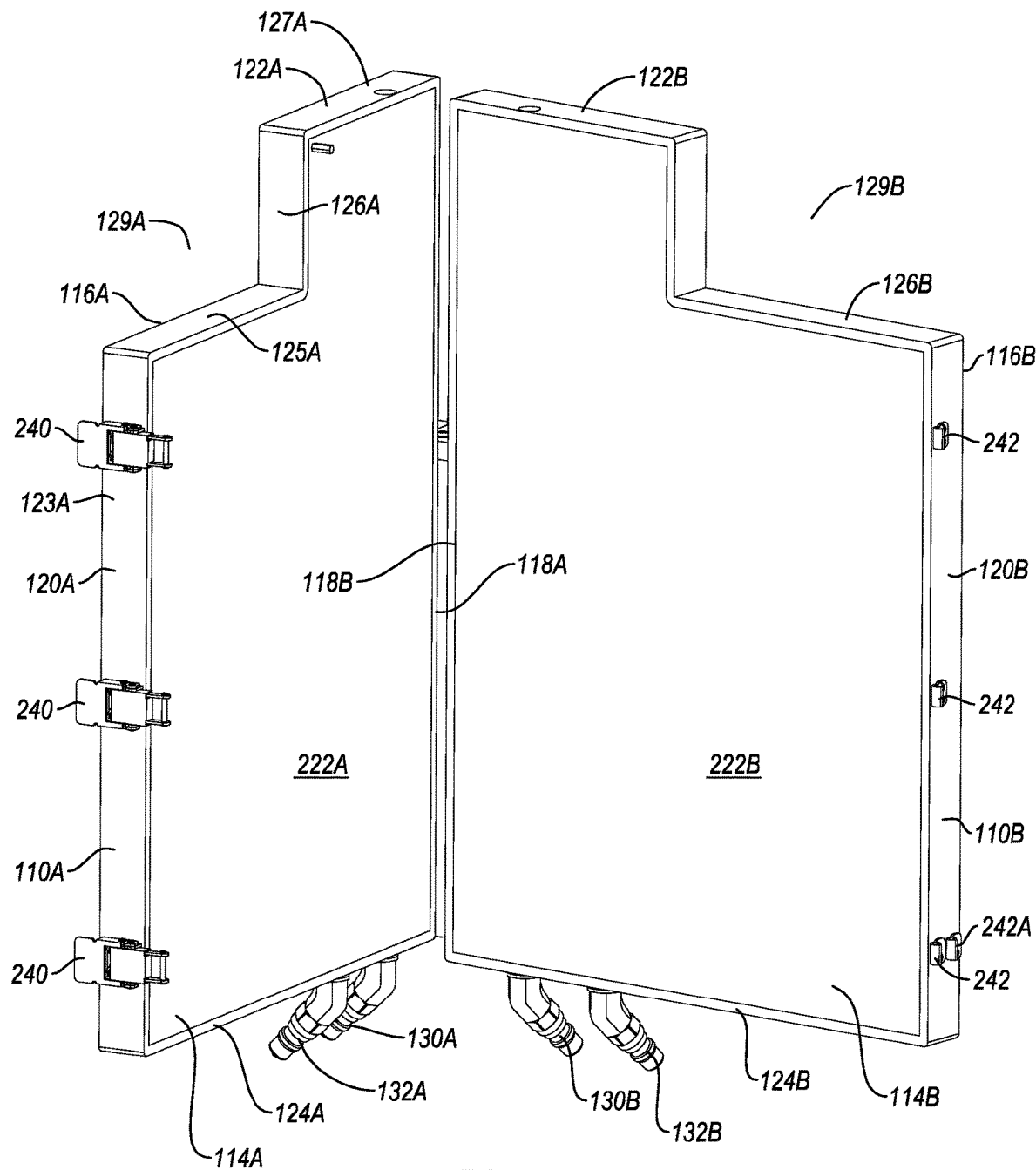
FIG. 6 is a perspective view of the condenser shown in FIG. 5 in an opened position.

Returning to FIG. 1, condenser system 16 generally comprises a condenser 100, a condenser bag 102, a chiller 104, and a pump 106. Turning to FIG. 5, condenser 100 comprises a first panel 110A and a second panel 110B that are hingedly coupled together by a bracket 140. As depicted in FIG. 6, first panel 110A includes interior face 114A and an opposing exterior face 116A that extend between an inside edge 118A and an outside edge 120A. First panel 110A also includes a top edge 122A and an opposing bottom edge 124A. Edges 118A, 120A, 122A and 124A combine to form a perimeter edge 123A that encircles panel 110A. An enlarged notch 129A is formed on top edge 122A at the intersection with outside edge 120A. As such, top edge 122A includes a first section 125A inwardly extending from outside edge 120A, a third section 127A inwardly extending from inside edge 118A and a second section 126A upwardly extending from first section 125A to third section 127A.

Notch 129A is bounded by sections 125A and 126A which can extend orthogonally to each other to form an inside corner having a substantially square or rectangular configuration. However, other configurations can also be used. For example, sections 125A and 126A can form a curved arch.

Faces 114A and 116A of panel 110A are typically planer and are typically disposed in parallel alignment. In one embodiment panel 110A has a maximum thickness extending between faces 114A and 116A in a range between about 1 cm and 6 cm. Other thicknesses can also be used. If desired, exterior face 116A can be contoured and/or sloped relative to interior face 114A. Interior face 114A, however, is typically smooth/planar to achieve full contact with condenser bag 102 without risk of damage to condenser bag 102.

Figure 7:
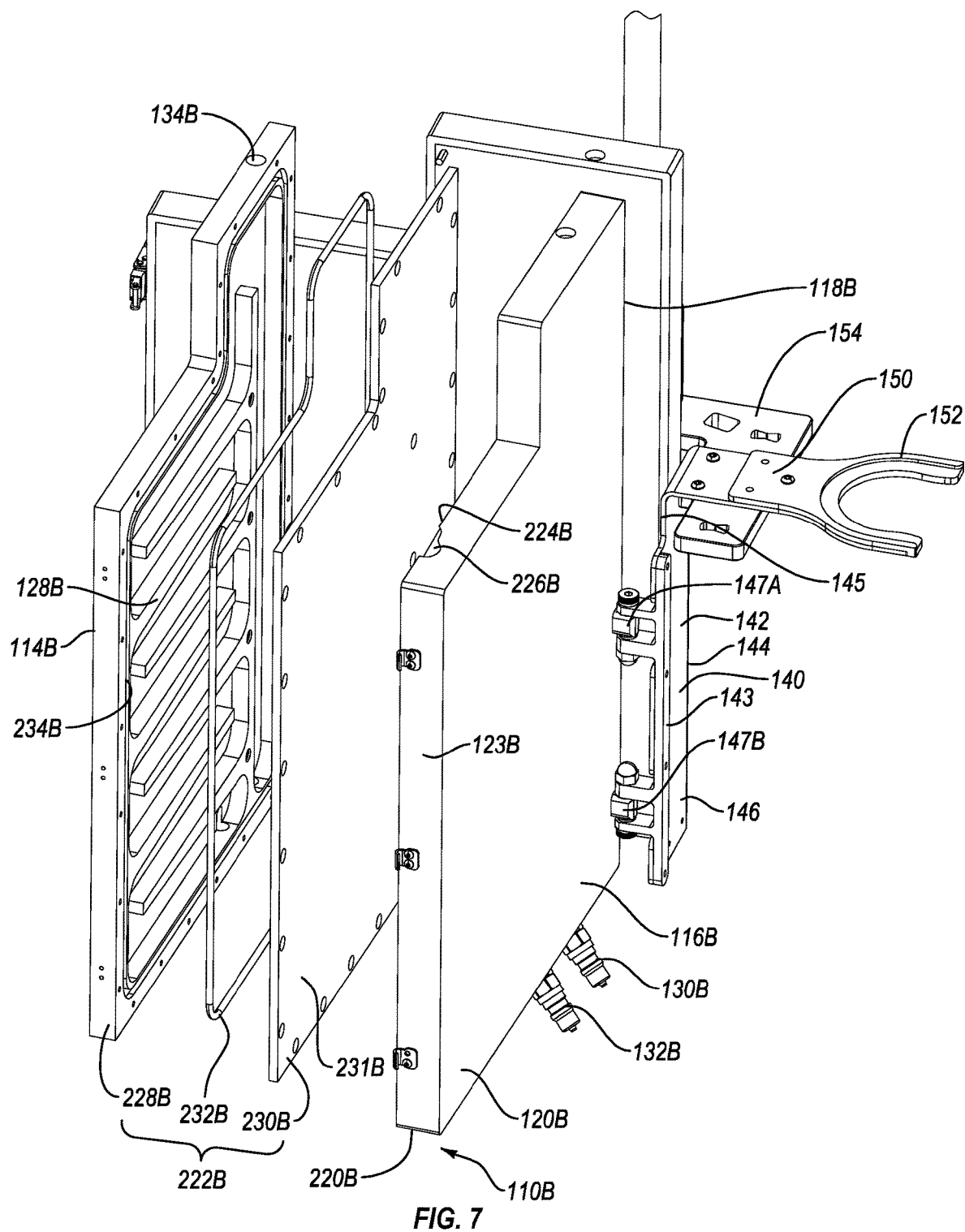
FIG. 7 is a partially exploded view of the condenser shown in FIG. 6.

Second panel 110B has substantially the same configuration and same components as first panel 110A but is the mirror image in design Like elements between panels 110A and B are identified by like reference characters except that the elements of first panel 110A include the letter "A" while element of second panel 110B include the letter "B". As depicted in FIG. 7, second panel 110B comprises an outer cover 220B and an inner panel 222B. Outer cover 220B has an inside face 224B and opposing exterior face 116B with perimeter edge 123B extending therebetween. A recessed pocket 226B is formed on inside face 224B that is complementary to and configured to receive inner panel 222B. In one embodiment, outer cover 220B is made from a polymeric material, such as a polyurethane foam, that can be over molded onto inner panel 222B. Otherwise, it can be attached by an adhesive or other fastening technique.

In general, inner panel 222B has interior face 114B and an opposing exterior face 231B with a perimeter edge 236B extending therebetween. Perimeter edge 236B has a configuration complementary to perimeter edge 123A except that it has a slightly reduced dimension so that it can snugly fit within recessed pocket 226B. Inner panel 222B bounds a fluid channel 128B. More specifically, inner panel 222B comprises a panel body 228B, a cover plate 230B and seal 232B that is disposed therebetween. Panel body 228B has interior face 114B and an opposing outer face 234B. Recessed within outer face 234B is fluid channel 128B.

Figure 8:
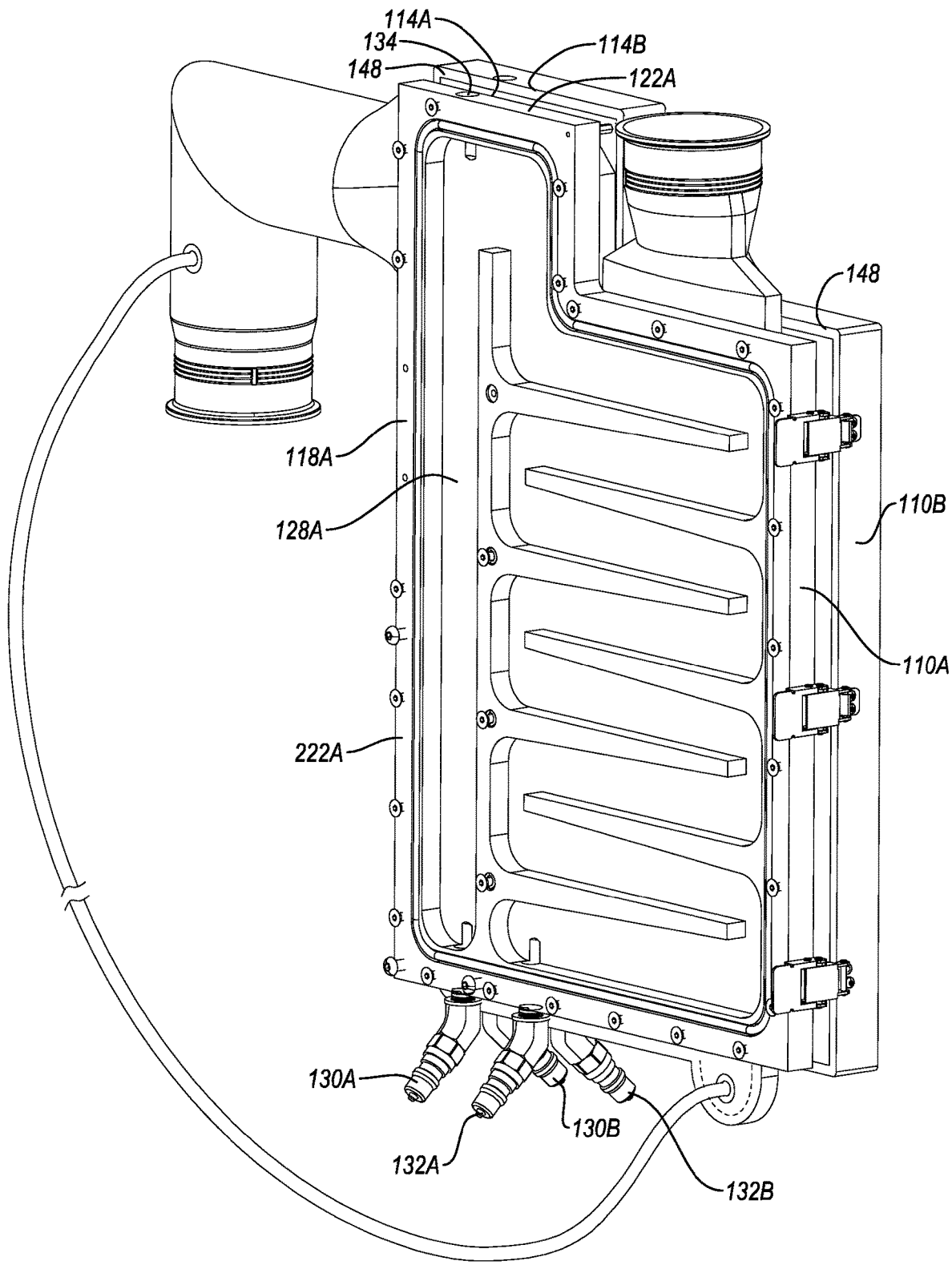
FIG. 8 is a partially disassembled view of the condenser shown in FIG. 6.

As more clearly depicted in FIG. 8, fluid channel 128A of first panel 110A, which has the same configuration as fluid channel 128B of second panel 110B, lies beneath at least 60% and more commonly at least 70%, 80% or 90% of interior face 114A (FIG. 6). Fluid channel 128A starts at an inlet port 130A that communicates through a bottom edge of inner panel 222A and terminates at an outlet port 132A that communicates through the bottom edge of inner panel 222A. In alternative embodiments, ports 130A and 132A can be disposed at different locations on inner panel 222A. Furthermore, fluid channel 128A is shown having, in part, a sinusoidal or tortious path but can have a variety of different configurations. By traveling in a tortious path, the fluid traveling through fluid channel 128A is retained within inner panel 222A/first panel 110A for an extended period, thereby optimizing heat transfer between the fluid traveling through fluid channel 128A and inner panel 222A. A vent port 134A extends through the top edge of inner panel 222A and communicates with fluid channel 128A. Vent port 134A is used for removing air from fluid channel 128A when filling fluid channel 128A with liquid and can be plugged during use by any conventional form of plug.

Returning to FIG. 7, cover plate 230B is secured on outer face 234B of panel body 228B with seal 232B positioned therebetween so as to seal fluid channel 128B closed except for access through ports 130B, 132B and 134B. Cover plate 230B can be secured by use of screws, welding, other fasteners, or other conventional techniques.

Inner panel 222B, and particularly panel body 228B, is typically comprised of a material having high thermal conductivity to permit good heat transfer between inner panel 222B and condenser bag 102. Preferred materials include metals such as aluminum, stainless steel, or the like. Other materials having a relatively high thermal conductivity can also be used. Outer cover 230B acts as an insulator for inner panel 222B and is typically made of a material having a lower thermal conductivity than inner panel 222B or panel body 228B. For example, as previously mentioned, outer cover 230B is typically made of polymeric material or polymeric foam, such as polyurethane foam. Again, other materials can also be used.

It is again noted that panels 110A and 110B have substantially the same configuration and the same components but are the mirror image in design. As such, discussions herein with regard to one of panels 110A or 110B are equally applicable to the other panel 110A or 110B.

Panels 110A and B are hingedly coupled together by bracket 140. Specifically, bracket 140 includes a back 142 having a first side 143 and an opposing second side 144 that extend between an upper end 145 and a lower end 146. First side 143 is connected to exterior face 116B of second panel 110B by a pair of spaced apart hinges 147A and 147B that are disposed adjacent to inside edge 118B. Second side 144 is rigidly secured to first panel 110A at side 116A. As a result of this configuration, panels 110A and 110B can be selectively moved between a closed position, as shown in FIG. 5, where panels 110A and B are disposed in substantially parallel alignment, and an open position, as shown in FIG. 6, wherein second panel 110B is outwardly rotated relative to first panel 110A so that panels 110A and B are disposed in diverging planes. In alternative embodiments, it is appreciated that hinges 147A and B can be mounted on first panel 110A instead of or in addition to being mounted on second panel 110B. Furthermore, in an alternative embodiment, instead of being mounted on exterior face 116A and/or 116B, hinges 147A and B can be mounted on inside edges 118A and/or 118B. A variety of other hinge configurations and types can also be used.

Back 142 of bracket 140 is sized so that when panels 110A and B are in the closed position, a gap 148 is formed between interior faces 114A and B of panels 110A and B adjacent to inside edges 118A and B. Gap 148 can be a variety of different thickness depending on factors such as the gas flow rate and the temperature of condenser 100. In some common embodiments, gap 148 is typically in a range between about 0.5 cm and 3 cm with about 1 cm to about 2 cm being more common. Other dimensions can also be used. As discussed below in more detail, gap 148 can be used to regulate the gas flow rate through condenser bag 102.

Figure 9:
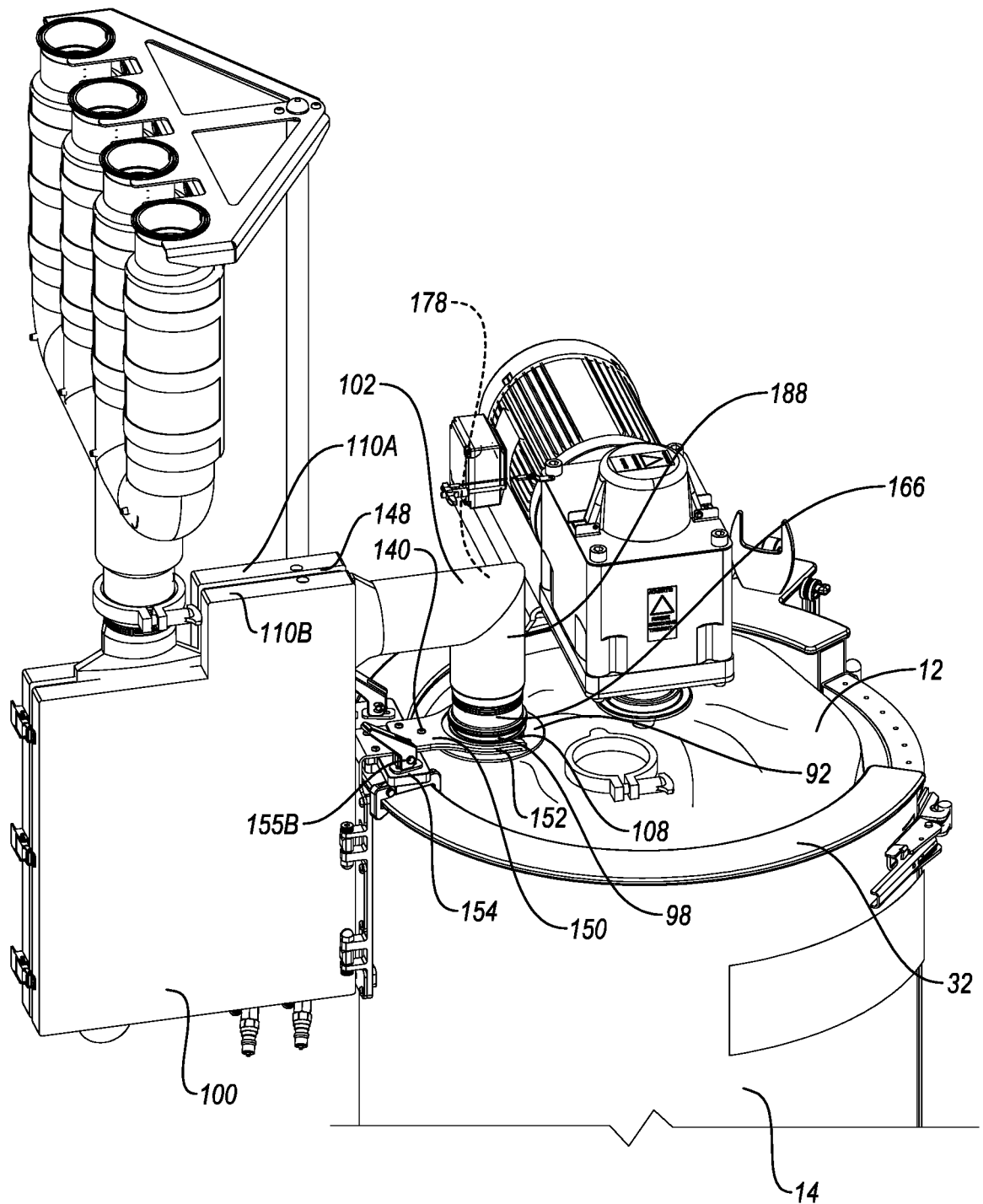
FIG. 9 is a right side perspective view of the system components shown in FIG. 5.

Returning to FIG. 7, bracket 140 also includes an arm 150 outwardly projecting from upper end 145 of back 142. Arm 150 terminates at a U-shaped catch 152 that is positioned vertically over container 12 within support housing 14. Catch 152 is used to capture and retain exhaust port 92 on container 12 (FIG. 2). Attached to and horizontally extending from arm 150 is a mount 154. As depicted in FIGS. 5 and 9, mount 154 is used, in part, for securing condenser 100 to support housing 14. Specifically, fasteners 155A and B, that are secured to lip 32 of support housing 14, are used to releasably attach mount 154 to support housing 14 through holes formed on mount 154. It is appreciated that any number of different types of fasteners can be used to secure mount 154 to support housing 14. In alternative embodiments, mount 154 can be formed as an integral, unitary part of bracket 140, as opposed to being attached thereto, or can be separately attached to one or both of panels 110A and B, either through hinges or rigid fasteners. Other techniques can also be used to secure condenser 100 to support housing 14.

Mount 154 is typically positioned at a location between and spaced apart from top edges 122 and bottom edge 124 of panels 110 so that a portion of condenser 100 projects above lip 32 of support housing 14 and container 12 and a portion projects below lip 32 of support housing 14 when condenser 100 is mounted to support housing 14. For example, top edge 122A is typically at least 5 cm and more commonly at least 10 cm above lip 32 of support housing 14 while bottom edge 124A is typically at least 5 cm and more commonly at least 10 cm below lip 32 of support housing 14. This positioning helps to optimize both access to and operation of condenser bag 102 which is received within condenser 100. However, other positions can also be used. In the attached position, panels 110 are typically vertically orientated and radially outwardly project from the exterior surface of support housing 14. If desired, panels 110 could also be angled, such as in a range between +/−10° or 20° relative to vertical.

Returning to FIG. 6, mounted on outside edge 120A of first panel 110A are a plurality of spaced apart latches 240 while mounted on outside edge 120B of second panel 110B are a plurality of catches 242. When panels 110A and B are in the closed position, latches 240 can engage catches 242 so as to securely lock panels 110A and B in the closed position. Latches 240 are configured so that gap 148 is also formed between panels 110A and B adjacent to outside edges 120A and B when panel 110 are in the closed position. It is appreciated that any number of different types of latches can be used to securely lock panels 110A and B together in the closed position. Examples of other types of latches include Velcro (hook and eye) straps, buckles, ties, clamps, bolts, threaded fasteners, and the like.

In one embodiment of the present invention, means are provided for locking panels 110A and B together in the closed position so that gap 148 between panels 110A and B can be adjusted. One example of such means can include mounting a second catch 242A on outside edge 120B of second panel 110B on the near side and/or far side of each catch 242. As a result, latches 240 can be used to engage catches 242 or 242A depending on the desired width for gap 148. As discussed below in more detail, adjusting the width of gap 148 adjusts the flow rate at which gas passes condenser bag 102 that is held between panels 110A and B. In general, the gas flow rate decreases as the width of gap 148 increases. Thus, by having multiple different catches 242 and 242A, the width of gap 148 can be set to optimize processing parameters. It is appreciated that there are a wide variety of conventional locking techniques, such as Velcro (hook and eye) straps, buckles, ties, adjustable clamps, threaded fasteners, and other types of latches, and the like, that can be used to releasably lock panels 110A and B in the closed position so as to permit adjusting gap 148 between panels 110A and B.

In one embodiment of the present invention, means are provided for regulating the temperature of condenser 100. By way of example and not by limitation, FIG. 1 depicts chiller 104 being fluid coupled to condenser 100 by delivery lines 158A and 158B coupled within inlet ports 130A and B (FIG. 6) and return lines 160A and 160B coupled within outlet ports 132A and B (FIG. 6), respectively. Chiller 104 can comprise a conventional, off-the-shelf recirculating chiller that is configured to hold a volume of fluid (typically water), chill the fluid to a desired temperature, and then circulate the fluid into and out of the chiller body through delivery lines 158 and return lines 160, respectively. One example of chiller 104 is the Neslab RTE-221 recirculating chiller produced by Thermo Fisher Scientific. Other conventional recirculating chillers will also work.

During operation, chiller 104 pumps a continuous stream of a fluid chilled to a desired temperature to inlet ports 130A and B of condenser 100 through delivery lines 158A and 158B. The chilled fluid then flows through fluid channels 128A and B within condenser 100 to outlet ports 132A and B. Finally, the fluid passes out through outlet ports 132A and B and returns to chiller 104 through return line 160A and B. Because of the high thermal conductivity of the material of inner panels 222A and 222B that bound fluid channels 128A and B, the cooled fluid absorbs heat from panels 110A and B and from objects contacting opposing interior faces 114A and B of panels 110. Chiller 104 is typically operated with the fluid passing therethrough being cooled to a temperature in a range between about 3° C. to about 18° C. with about 3° C. to about 10° C. being more common. Other temperatures can also be used.

Other means for regulating the temperature of condenser 100 can also be used. For example, the chiller can be designed to circulate a gas and can be provided with a compressor that compresses and expands the gas so that the chiller operates as a refrigeration system that cools condenser 100. The chiller can also be designed to blow cooled air or other gases through condenser 100. Other conventional chillers and systems for cooling can also be used for cooling condenser 100.

Figure 10:
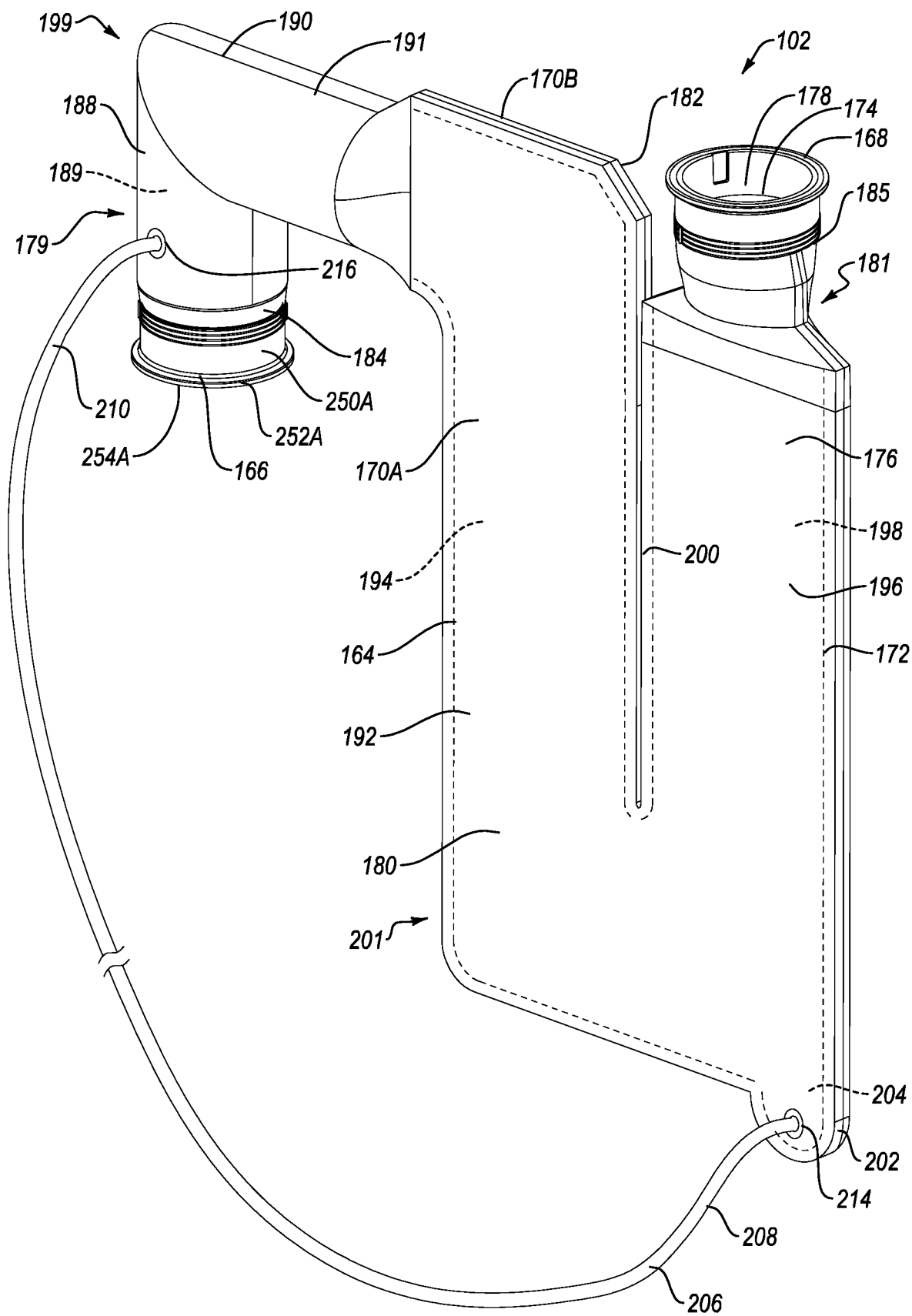
FIG. 10 is a perspective view of a condenser bag that is used with the condenser shown in FIG. 6.

Turning to FIG. 10, condenser bag 102 generally comprises a body 164 having an intake port 166 disposed at one end and an exhaust port 168 disposed at the opposing end. Body 164 comprises a flexible, collapsible bag comprised of one or more sheets of polymeric film. Body 164 can be comprised of the same materials and produced using the same manufacturing methods as previously discussed above with regard to container 12. In the depicted embodiment, body 164 comprises a pillow type bag that is manufactured from two overlapping sheets 170A and B of polymeric film that are seamed together around a perimeter edge 172. Body 164 has an interior surface 174 and an opposing exterior surface 176. Interior surface 174 bounds a channel 178 that extends between a first end 179 and an opposing second end 181. Formed at first end 179 is an inlet opening 184 where intake port 166 is attached while formed at second end 181 is an outlet opening 185 where exhaust port 168 is attached. Exterior surface 176 comprises first side face 180 and an opposing second side face 182.

With reference to FIG. 10, body 164 can be defined in terms of specific parts that bound sections of channel 178. Specifically, body 164 comprising a first leg 188 located at first end 179. First leg 188 upwardly extends from a first end coupled with intake port 166 and an opposing second end coupled with a first arm 190. First leg 188 bounds a first channel section 189 that extends along the length thereof. First arm 190 laterally extends from first leg 188 to a first end of a second leg 192. First arm 190 bounds a second channel section 191 extending along the length thereof. Second leg 192 downwardly projects from its first end to a second end. Second leg 192 bounds a third channel section 194 that extends along the length thereof. In the depicted design, leg 188, arm 190, and leg 192 form a first section of body 164 having a U-shaped configuration, the channel sections extending therethrough also combine to form a U-shaped configuration.

Coupled to the second end of second leg 192 is the first end of a third leg 196. Third leg 196 upwardly projects to a second end in a substantially vertical orientation. Exhaust port 168 is secured to the second end of third leg 196. Third leg 196 bounds a fourth channel section 198 that extends along the length thereof. The combination of legs 192 and 196 and the combination of channel sections 194 and 198 each combine to form a second section having a U-shaped configuration. It is understood that all of the channel sections are coupled together so that gas entering through intake port 166 can sequentially pass through channel sections 189, 191, 194, and 198 and then exit through exhaust port 168. The U-shaped sections of body 164 increase the retention time of the gas therein to improve condensation. Body 164 is also configured so that condensed liquid collects within the second U-shaped section at a lower end 201 of body 164.

Although legs 188, 192 and 196 are shown as being linear and in parallel alignment, in alternative embodiments one or more of the legs can be angled, such as in a range between 1° to 45° relative to vertical, or extend in a curved or irregular path. Likewise, arm 190 can extend horizontally to intersect perpendicular with leg 188 and/or leg 192. Alternatively, arm 190 can extend at an angle, such as in a range between 1° to 45° relative to horizontal or in a curved or irregular path. For example, arm 190 can extend in a curved arch between legs 188 and 192.

In the depicted embodiment, a slot 200 is shown separating legs 192 and 194 except where they are coupled together at lower end 201 of body 164. In alternative embodiments, legs 192 and 194 can be separated by a partition. In one embodiment, the partition can be produced by forming a weld seal between sheets 170A and B along the current location of slot 200 so that fluid cannot pass through the partition. The weld seal is formed by welding together overlapping sheets 170A and B using methods known in the art such as heat energies, RF energies, sonics, or other sealing energies. In an alternative embodiment, the partition can be produced by forming a linear ridge along interior face 114A and/or 114B of condenser 100 (FIG. 6) so that when condenser bag 102 is closed between panels 110A and B, the one or both ridges pinch sheets 170A and B together so as to form a temporary seal along the current location of slot 200. Other methods can also be used. If desired, legs 192 and 194 can be spaced apart similar to legs 188 and 192 by forming a second arm the laterally extends between the second end of second leg 192 and the first end of third leg 196.

The channel sections bounded within the arms and legs of body 164 can also extend in the same orientations as discussed above with regard to the corresponding arms and legs. For example, if it is desired to maintain gas longer within second leg 192 to improve condensation of the gas, second leg 192 can be formed so that third channel section 194 downwardly extends in a sinusoidal path or other curved path.

Body 164 includes an extension 202 downwardly projecting from lower end 201 of body 164 and bounds a collection pocket 204 that forms a portion of channel 178. More specifically, collection pocket 204 is formed at the first end of third leg 196 so as to be in alignment with and in fluid communication with fourth channel section 196. A transfer line 206, such as in the form of a flexible tube, has a first end 208 coupled with extension 202 so as to be in fluid communication with collection pocket 204 and has an opposing second end 210 coupled with first leg 188 so as to be in fluid communication with first channel section 189. Although transfer line 206 typically comprises polymeric tubing, other materials and tube designs can be used. First end 208 of transfer line 206 can couple with extension 202 through a port 214 mounted thereon while second end 210 of transfer line 206 can couple with first leg 188 through a port 216 mounted thereon. As a result, fluid collected in collection pocket 204 can be pumped into first channel section 189. As discussed below in more detail, by pumping the fluid into first channel section 189, the fluid naturally falls under gravitational force down through intake port 166 of condenser bag 102 and through exhaust port 92 of container 12 so as to be returned to compartment 50 of container 12.

As depicted in FIG. 11, intake port 166 of condenser bag 102 comprises a tubular stem 250 having an interior surface 251 and an opposing exterior surface 253 that extends between a first end and an opposing second end. The first end is secured to inlet opening 184 of body 164 such as by being received within inlet opening 184 and being welded thereto. Encircling and outwardly projecting from the second end of stem 250 is a coupling flange 252. Coupling flange 252 has a top surface 254 with an annular seal 256 formed thereon. (Seal 256 is shown on exhaust port 168 which has the same configuration as intake port 166).

Interior surface 251 bounds a port opening 257 that extends through stem 250 and communicates with channel 178. In the depicted embodiment, port opening 257 has a circular transverse cross section. Other configurations can also be used such as elliptical, polygonal, irregular or the like. The transverse cross section of port opening 257 typically has a maximum diameter in a range between about 0.5 cm to about 15 cm with about 2 cm to about 10 cm being more common. For high gas throughput, the maximum diameter is typically greater than 3 cm, 4 cm, 5 cm or 6 cm. Other dimension can also be used depending on the intended application. The body of intake port 166 is typically molded from a polymeric material and is more rigid than body 164. Annular seal 256 is typically formed from an elastomeric material that is more flexible than the port body on which it is attached.

Coupling flange 252 of intake port 166 of condenser bag 102 is configured to mate with coupling flange 99 of exhaust port 92 on container 12 so that when clamp 258 is tightened over the mated flanges 99 and 252, seals 110 and 256 press together forming a gas tight seal that will maintain sterility. In the depicted embodiment, flanges 99 and 252 have the same size and configuration. Furthermore, aligned port openings 97 and 257 have the same size and configuration so that there is no restriction of the gas as it passes between the ports. However, it is not necessary that the ports have the same size port opening as long as a sterile connection can be made between the ports. It is noted that exhaust port 92 on container 12 and intake port 166 of condenser bag 102 are typically coupled together by clamp 258 at the end of the manufacturing stage so that container 12 and condenser bag 102 can be concurrently sterilized, such as by radiation, prior to shipping and use. In contrast to using flanges and a clamp to secure ports 92 and 166 together, it is appreciated that a variety of other types of mechanical connections can be used such as threaded connections, snap-fit connections, bayonet connections, sterile connectors and other types of connectors that can maintain a sterile connection. These types of alternative connections are also applicable to the other port coupling discussed herein where flanges and a clamp is used to form the connection.

Exhaust port 168 can have the same configuration, dimensions, composition and properties as intake port 166 and can be secured to outlet opening 185 at second end 181 of body 164 using the same method as discussed with intake port 166. Accordingly, like elements between ports 166 and 168 are identified by like reference characters.

Condenser bag 102 serves two primary functions. First, humid gas exiting out of container 12 is cooled within condenser bag 102 by condenser 100 so that the vapor condenses into a liquid and is collected within collection pocket 204. The liquid is then subsequently removed. As discussed below, dehumidifying the gas prevents clogging of downstream filters. Second, as a result of adding gas into container 12 through sparger 54 (FIG. 2), foam can be produced at the upper end of container 12. The foam can potentially enter and travel along condenser bag 102. However, if the foam reaches the downstream filters, the foam can clog the filters. Condenser bag 102 is thus formed having channel 178 with a sufficient length so that the humid gas is retained therein for a sufficient time to achieve the desired condensation and to break down any foam entering channel 178 before it exits condenser bag 102. To achieve the desired retention time, it is appreciated that channel 178 can have a variety of different lengths and configurations.

Figure 12:
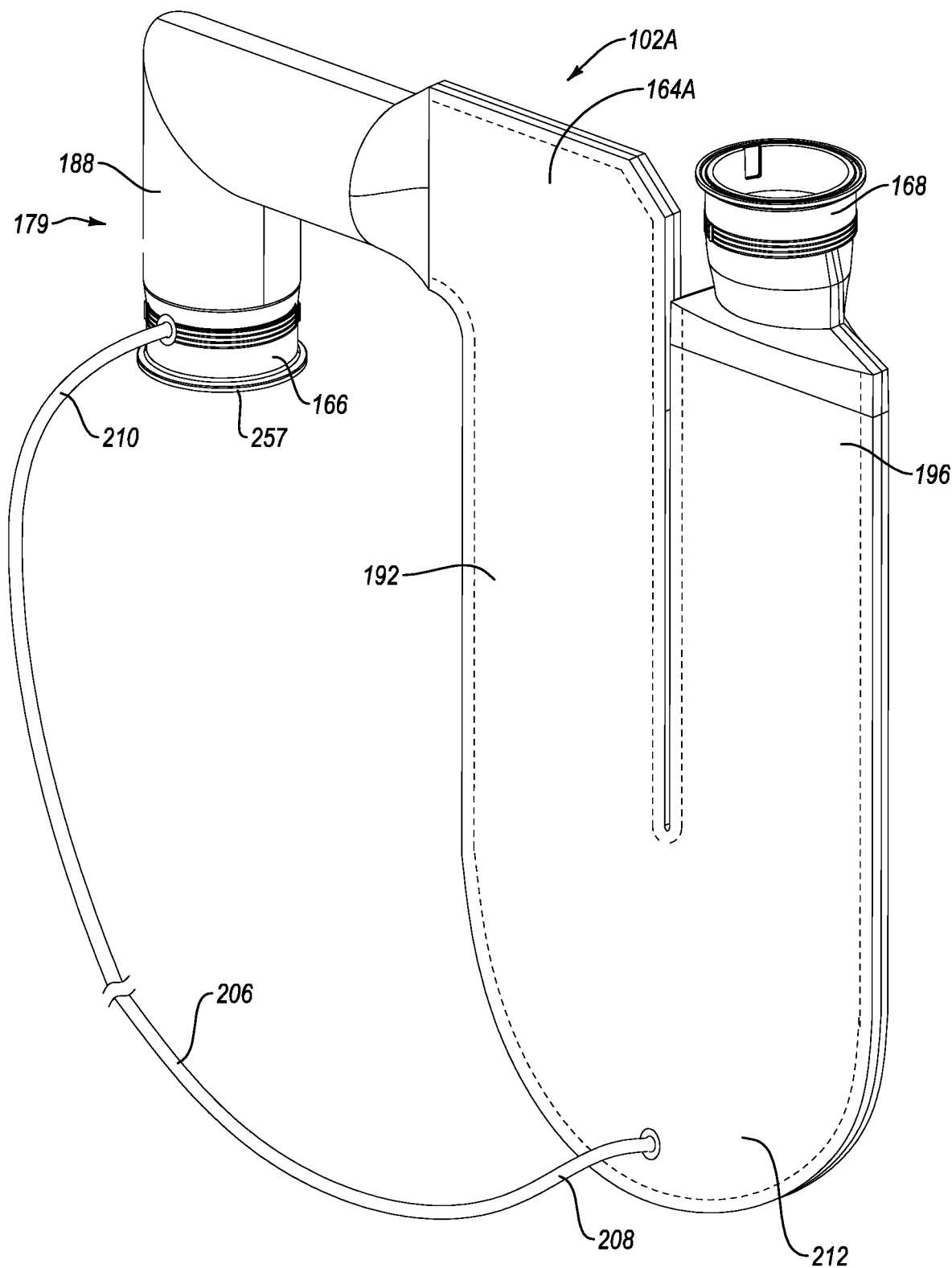
FIG. 12 is a perspective view of an alternative embodiment of the condenser bag shown in FIG. 10.

In addition to channel 178 having a variety of different configurations, transfer line 206 can be connected at a variety of different locations. For example, with reference to FIG. 10, collection pocket 204 could be formed at any location along lower end 201 of body 164, such as in alignment with second leg 192 or at the junction between legs 192 and 196, where water will collect. Collection pocket 204 can also be eliminated and transfer line 206 can be positioned at any location aligned with second leg 192, third leg 196 or at the junction between legs 192 and 196 where water will collect. Furthermore, second end 210 of transfer line 206 need not connect with first leg 188 or first end 179 of body 164 but can be directly coupled with intake port 166. For illustration, depicted in FIG. 12 is an alternative embodiment of a condenser bag 102A wherein like elements between condenser bag 102 and 102A are identified by like reference characters. Condenser bag 102A includes a body 164A that includes legs 192 and 196. Legs 192 and 196 join at U-shaped junction 212 where the condensed liquid collects. First end 208 of transfer line 206 is coupled with body 164A at junction 212. Second end 210 of transfer line 206 is coupled directly with the side of intake port 166 so that the liquid is dispensed into port opening 257 which then falls down into container 12.

Figure 13:
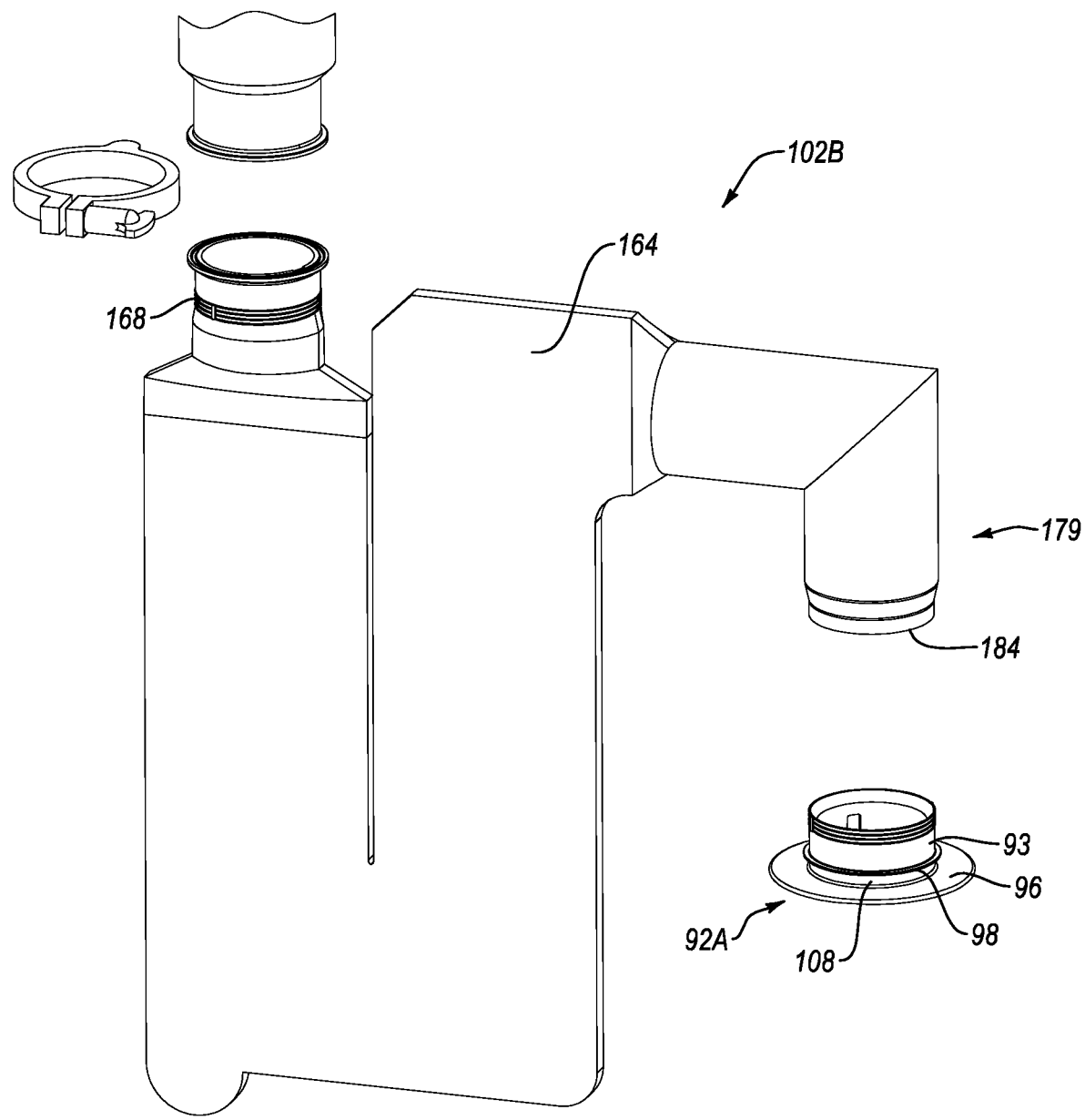
FIG. 13 is a perspective view of another alternative embodiment of a condenser bag that can be coupled with the container shown in FIG. 1 by use of a single port.

In another alternative embodiment, intake port 166 of condenser bag 102 can be eliminated. For example, depicted in FIG. 13 is a condenser bag 102B where like elements between condenser bag 102 and 102B are identified by like reference characters. Condenser bag 102B includes body 164 having exhaust port 168 mounted thereon. However, inlet opening 184 is not coupled with intake port 166 (FIG. 10) but rather is now coupled directly with a modified exhaust port 92A. Like elements between exhaust port 92 on container 12 and exhaust port 92A are identified by like reference characters. Exhaust port 92A includes stem 93 having mounting flange 96 formed at the first end thereof for coupling with container 12, as previously discussed, and includes retention flange 98 with annular groove 108 formed between flanges 96 and 98. However, coupling flange 99 has been eliminated. The second end of stem 93 is now elongated and configured to be received within inlet opening 184 of body 164 so as to be welded and sealed directly thereto. As a result, the opposing ends of port 92A are secured directly to container 12 and body 164, thereby eliminating the need for intake port 166 and clamp 258.

Returning to FIG. 5, container 12 and condenser bag 102 are typically preassembled and sterilized during the manufacturing stage. During use, container 12 is positioned within support housing 14 while attached condenser bag 102 is mounted on condenser 100. Specifically, condenser 100 is moved to the open position, as shown in FIG. 6, following which condenser bag 102 is placed between panels 110A and B. Condenser bag 102 is orientated so that arm 190 projects out from between panels 110A and B toward container 12 while exhaust port 168 is aligned with notches 129. In this position, condenser 100 is moved to the closed position, as shown in FIG. 5, and latches 240 are locked in place so that condenser bag 102 is captured between panels 110A and B. Because of gap 148, however, condenser bag 102 is not compressed between the interior surfaces of panels 110A and B prior to operation but rather is free to expand slightly within gap 148 when gas is received therein. Extension 202 of condenser bag 102 projects down below panels 110A and B so that first end 208 of transfer line 206 is not compressed or potentially kinked between panels 110A and B. In alternative designs, the lower end of body 164 could project below panels 110A and B or a slot, notch, or other opening could be formed on one of panels 110A and B to receive first end 208 of transfer line 206 so that no portion body 164 needs to extend below panels 110A and B. As depicted in FIG. 1, transfer line 206 is coupled with pump 106 so that fluid can be pumped along transfer line 206. Pump 106 typically comprises a peristaltic pump but other pumps could also be used depending on the application.

With reference to FIGS. 9 and 11, exhaust port 92 on container 12 is attached to bracket 140 mounted on support housing 14. Specifically, exhaust port 92 is laterally slid onto catch 152 so that catch 152 is received within first annular grove 108 and retention flange 98 rests on top of catch 152. In this configuration, exhaust port 92 is securely held in place with port opening 97 facing vertically upward. If desired, retention flange 98 can be angled so that exhaust port 92 projects at an angle. For example, exhaust port 92 can have a central longitudinal axis that projects at an angle in a range between 0° and 30° and more common between 0° and 15° relative to vertical. Once condenser bag 102 is attached to condenser 100 and coupled with container 12, an upper end 199 (FIG. 10) of condenser bag 102 can be positioned above and vertically over container 12 while lower end 201 (FIG. 10) of condenser bag 102 can be positioned radially outside of support housing 14 at a location below lip 32 of support housing 14. Although condenser bag 102 can also be in other positions, this position helps to optimize access to condenser bag 102 and coupling with container 12. This configuration also optimizes use of condenser system 16 in rooms with low ceiling heights.

Once container 12 and condenser bag 102 are properly positioned, drive shaft 72 of mixer assembly 18 is coupled with impeller assembly 78 as previously discussed. A fluid solution and any desired components are then fed through various ports into container 12. With reference to FIG. 2, while mixer assembly 18 mixes the contents within container 12, sparger 54 is used to deliver a gas, such as oxygen and/or other gases, into the solution at the lower end of container 12. As the gas passes through the solution, a portion of the gas is absorbed into the solution and gases such as carbon dioxide are desorbed from the solution. The remaining gas that is not absorbed by the fluid increases in humidity as a result of the solution to form a humid gas that passes into a head space 162 at the upper end of container 12. As previously discussed, the gas also typically forms foam that is collected in head space 162.

With reference to FIG. 9, as the gas pressure increases within container 12, the humid gas passes out through exhaust port 92 of container 12 and into channel 178 of condenser bag 102 through intake port 166. The humid gas causes condenser bag 102 to inflate. Leg 188 of condenser bag 102 is positioned outside of condenser 100 and can thus freely inflate. Condenser bag 102 is typically positioned so that when leg 188 is inflated, leg 188 and the channel section therein are longitudinally aligned with port opening 97 of exhaust port 92 (FIG. 11). Thus, where the central longitudinal axis of exhaust port 92 is vertically aligned or offset by an angle relative to vertical, leg 188 and the channel section therein are also typically aligned vertically or are offset by the corresponding angle so as to be aligned.

The portion of condenser bag within condenser 100 expands so that the opposing sides of condenser bag 102 push directly against interior faces 114A and 114B of inner panels 222A and 222B (FIG. 6). Chiller 104 is activated at the start of the process so that inner panels 222A and 222B are cooled by the chilled fluid passing therethrough. As such, the humid gas passing through condenser bag 102 is cooled by thermal energy being absorbed by inner panels 222A and 222B. As the humid gas is cooled, the moisture within the humid gas begins to condense so as to form a condensed liquid and a dehumidified gas. As discussed below, the dehumidified gas passes into filter system 17. The condensed liquid flows downward under gravity to lower end 201 of condenser bag 102 and into collection pocket 204 (FIG. 10).

Through the use of pump 106, the condensed liquid flows out of channel 178 through tubular port 214, travels along transfer line 206 and then dispenses back into first leg 188 or into intake port 166, depending on the embodiment. As previously discussed, because first leg 188 and intake port 166 are aligned either vertically or at some vertical angle with exhaust port 92 on container 12, the condensed fluid freely flows under the force of gravity back into compartment 50 of container 12. In alternative embodiments, it is appreciated that the second end of transfer line 206 could be coupled to a port coupled directly to container 12 or could be coupled to a separate container for collection of the condensed liquid. However, by having transfer line 206 connect back onto body 164, container 12 and condenser bag 102 can be completely manufactured at separate facilities or at different locations following which only a single connection is required to couple container 12 and condenser bag 102 together. As a result, the inventive condenser bag simplifies the manufacturing process and reduces manufacturing costs.

Condenser system 17 also has a number of other advantages over traditional condensers. For example, exhaust port 92 of container 12 and intake port 166 and exhaust port 168 of condenser bag 102 can be formed with large diameter port openings, as discussed herein. These large diameters enable large flow rates of gas to be easily and efficiently processed. For example, the inventive system, depending on the size thereof, can commonly operate at gas flow rates greater than 200 or 600 standard liters per minute ("slpm") and depending on the size thereof, it is envisioned that it can operate at gas flow rates greater than 2000, 5,000 or 10,000 slpm. Of course, the system can also operate at lower flow rates. Expressed in other terms, some embodiments of the system commonly operate at a gas flow rate between about 0.5 to about 2.5 vessel volumes per minute (based on the volume of container 12) with about 1 to about 2 vessel volumes per minute being more common.

Furthermore, in contrast to prior art condensers where the condenser bag is remotely coupled to the reactor bag by tubing, in one embodiment of the present invention the condenser bag 102 is directly coupled to container 12. This configuration occupies less space and simplifies the design and operation of the system while reducing material and manufacturing costs. Furthermore, because condenser 100 and condenser bag 102 can be configured to downwardly project along the length of support housing 14, as opposed to only projecting up above container 12, condenser system 16 is particularly useful in areas where there are low ceiling height restrictions.

An additional benefit of one embodiment of the inventive system is that the gas flow rate within condenser bag 102 can be easily adjusted. For example, if higher gas output is required without increasing gas pressure, gap 148 between the condenser panels 110 can be incrementally widened. This will permit condenser bag 102 to further expand so that a greater flow rate of gas can pass therethrough without increasing gas pressure.

Condenser bag 102 is also beneficial in that it is relatively inexpensive to manufacture, is easy to ship and install, and is disposable, thereby requiring no sterilization between uses. Other benefits also exist.

Figure 12A:
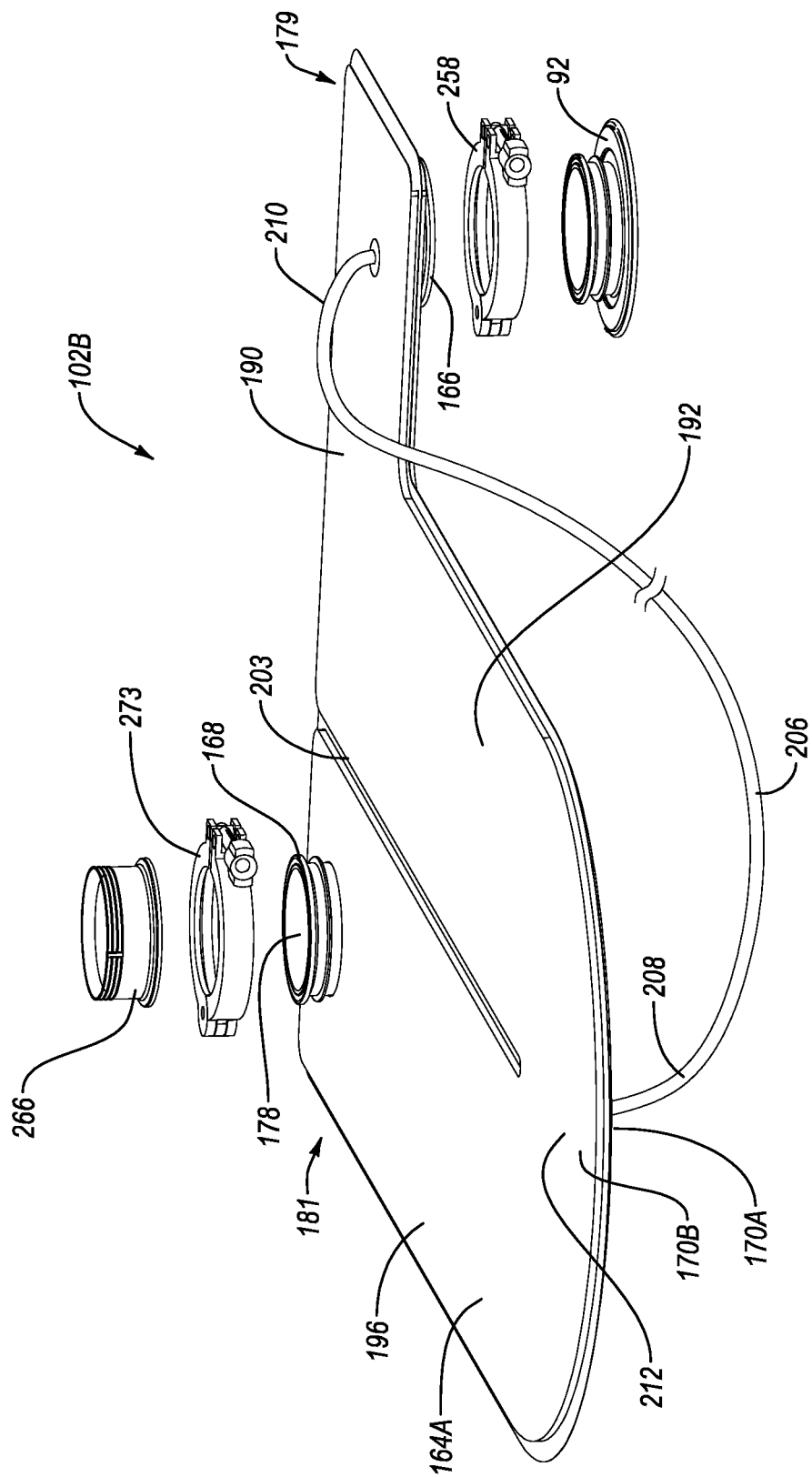
FIG. 12A is a perspective view of an alternative embodiment of the condenser bag shown in FIG. 12.

Depicted in FIG. 12A is another alternative embodiment of a condenser bag 102B wherein like elements between condenser bags 102, 102A and 102B are identified by like reference characters. Condenser bag 102B comprises a bag body 164A that includes overlapping sheets 170A and 170B that are welded or otherwise secured together around their perimeter edge to form a pillow bag. Body 164A bounds a channel 178 extending between opposing ends 179 and 181 and includes arm 190 and legs 192 and 196 which join together at U-shaped junction 212. Legs 192 and 196 are separated along a portion of their length by a partition 203. Partition 203 is formed by a weld seal that welds sheets 170A and 170B together.

In contrast to body 164A (FIG. 12), in body 164B first leg 188 has been eliminated. Intake port 166 is now secured to the face of sheet 170A at an inlet opening at first end 179 and exhaust port 168 is secured to the face of sheet 170B at an outlet opening at second end 181. During use, condenser 100 is mounted to support housing 12 so that condenser 100 is either horizontally disposed, i.e., rotated 90° relative to the vertical orientation depicted in FIG. 9, or is orientated at an angle in a range between 5° and 45° relative to the horizontal or more commonly at an angle in a range between 10° and 30° relative to horizontal. In this position, condenser bag 102B is positioned between panels 110A and 110B so that U-shaped junction 212 is at the low point.

Intake port 166 is then coupled with exhaust port 92 of container 12 so that gas from container 12 flows into condenser bag 102B. When condenser bag 102B is sloped, the condensed fluid collects at U-shaped junction 212 against sheet 170A. Transfer line 206 has first end 208 fluid coupled to the face of sheet 170A at U-shaped junction 212 and opposing second end 210 either coupled to the face of sheet 170B at first end 179, directly above intake port 166, or is coupled to the side of intake port 166. As a result, fluid collected within condenser bag 102B at U-shaped junction 212 can be pumped through transfer line 206 and then dispensed back into container 12 by passing through intake port 166 and exhaust port 92.

The above configuration and placement of condenser bag 102B has many of the same benefits as discussed above. In addition, it permits all of condenser bag 102 to be maintained at a higher elevation. Depending on the application, this can have additional benefits such as in space savings and less energy required to pump the condensed liquid through transfer line 206.

Figure 14:
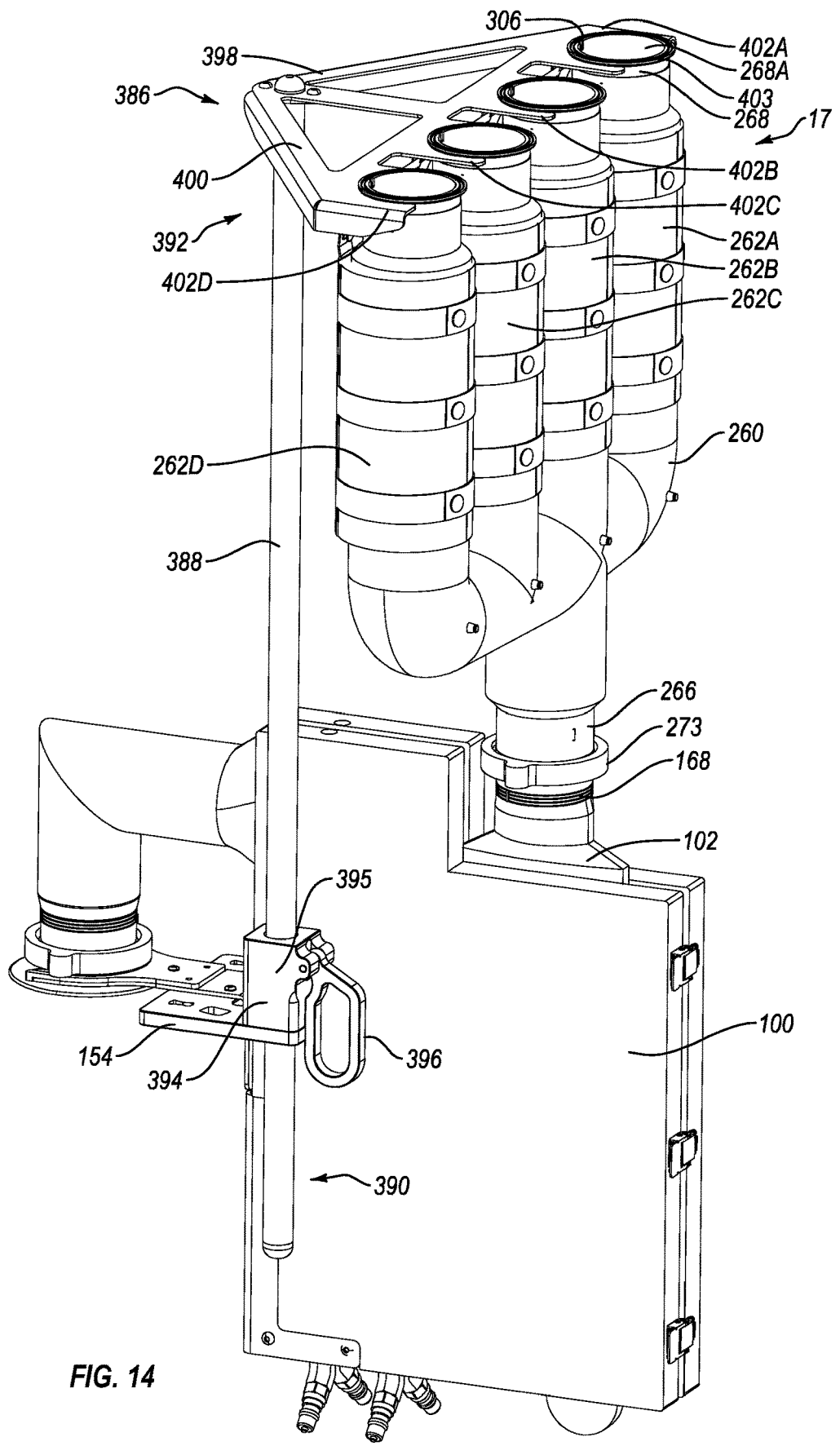
FIG. 14 is an enlarged perspective view of the filter system shown in FIG. 1.
Figure 15:
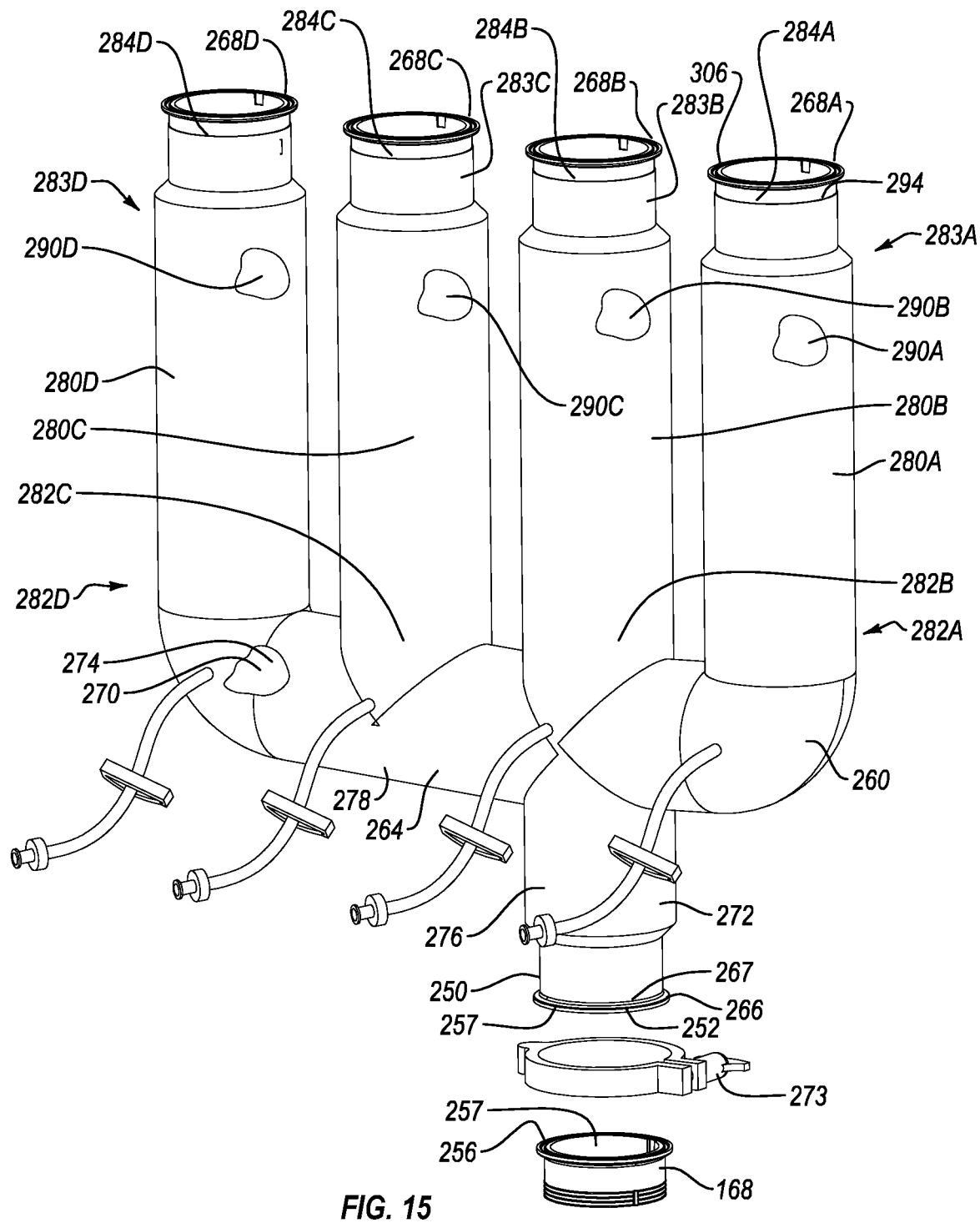
FIG. 15 is a perspective view of the filter assembly of the filter system shown in FIG. 14.

As depicted in FIG. 14, filter system 17 is coupled with exhaust port 168 of condenser bag 102. Filter system 17 includes a filter assembly 260 having a plurality of electrical heating jackets 262A-D mounted thereon. As depicted in FIG. 15, filter assembly 260 comprises a casing having an intake port 266 mounted thereon and a plurality of exhaust ports 268A-D mounted thereon. Casing 264 comprising a flexible, collapsible bag comprised of one or more sheets of polymeric material such as polymeric film. Casing 264 can be comprised of the same materials and be produced using the same manufacturing methods as previously discussed above with regard to container 12. In the depicted embodiment, casing 264 comprises a pillow type bag that is manufactured from two overlapping sheets of polymeric film that are seamed together around the perimeter edge.

Casing 264 has an interior surface 270 and an opposing exterior surface 272. Interior surface 270 bounds a compartment 274. Casing 264 can be defined in terms of specific parts that bound sections of compartment 274. Specifically, casing 264 comprises a tubular inlet 276 having a first end on which an inlet opening 267 is formed. Inlet opening 267 is configured to be coupled with intake port 266. Inlet 276 has an opposing second end that is coupled to a laterally extending tubular manifold 278. Outwardly projecting from manifold 278 on the side opposite of inlet 276 is a plurality of tubular sleeves 280A-D. Each sleeve 280A-D has a first end 282A-D fluid coupled with manifold 278 and an opposing second end 283A-D having a corresponding outlet opening 284A-D formed thereat. Each outlet opening 284A-D is configured to be coupled with a corresponding exhaust port 268A-D. Each inlet 276, manifold 278, and sleeve 280 bounds a portion of compartment 274 so that gas entering through inlet opening 267 can travel through inlet 276, through manifold 278, and through each sleeve 280A-D to outlet openings 284A-D.

In the embodiment depicted, sleeves 280A-D are disposed in parallel alignment and are orthogonal to manifold 278. In alternative embodiments, sleeves 280A-D need not be in parallel alignment and can be angled relative to manifold 278. However, there are operational benefits to using the depicted design. Inlet 276 is depicted as being aligned with sleeve 280B but can be positioned on manifold 278 so as to be offset from sleeves 280. Furthermore, in alternative embodiments inlet 276 can be eliminated by having inlet opening 267 and intake port 266 disposed directly on manifold 278.

Intake port 266 can have the same configuration, dimensions, composition and properties as previously discussed with regard to intake port 166 of filter bag 102. As such, like elements between intake port 166 and intake port 266 are identified by like reference characters. Intake port 266 is typically secured to casing 264 using the same method that intake port 166 of filter bag 102 is secured to body 164. For example, stem 250 of intake port 266 can be secured to inlet 276 by being received within inlet opening 267 and welded to inlet 276 so that coupling flange 252 is openly exposed. During use, intake port 266 of filter assembly 260 is coupled with exhaust port 168 of condenser bag 102 in the same way that intake port 166 of condenser bag 102 is coupled with exhaust port 92 on container 12, as previously discussed.

That is, the coupling flanges of intake port 266 and exhaust port 168 are clamped together using a clamp 273 so that the aligned seals 256 press together forming a gas tight seal that will maintain sterility. Again, the aligned port openings 257 of the ports typically have the same size and configuration so that there is no restriction of the gas as it passes between the ports. However, it is not necessary that the ports have the same size port opening as long as a sterile connection can be maintained between them.

Figure 16:
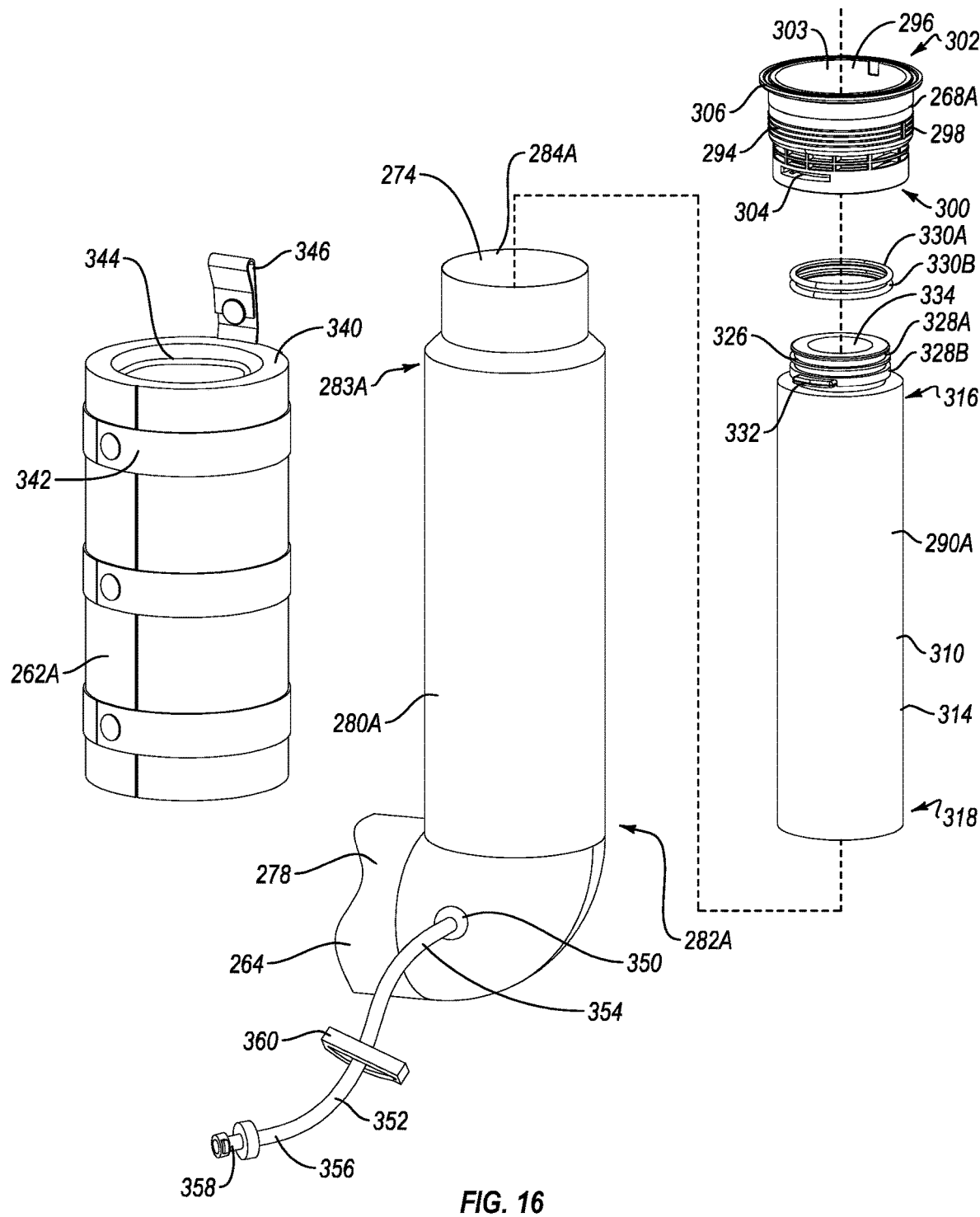
FIG. 16 is an exploded view of a portion of the filter system shown in FIG. 14.

As depicted in FIG. 16, each exhaust port 268 comprises a tubular stem 294 having an interior surface 296 and an opposing exterior surface 298 extending between a first end 300 and an opposing second end 302. Formed on interior surface 296 at first end 300 is a connector. In the depicted embodiment, the connector comprises a pair of opposing bayonet slots 304 formed on first end 300 so as to form half of a bayonet connection. Interior surface 296 bounds a port opening 303 which can have the same configurations and dimensions as previously discussed with regard to port opening 257 of inlet port 166. Encircling and radially outwardly projecting from second end 302 of stem 294 is a flange 306. During attachment, first end 300 of stem 294 of each exhaust port 268A-D can be received within the corresponding outlet opening 284A-D and welded to corresponding sleeve 280A-D so that flanges 306 are openly exposed.

Figure 17:
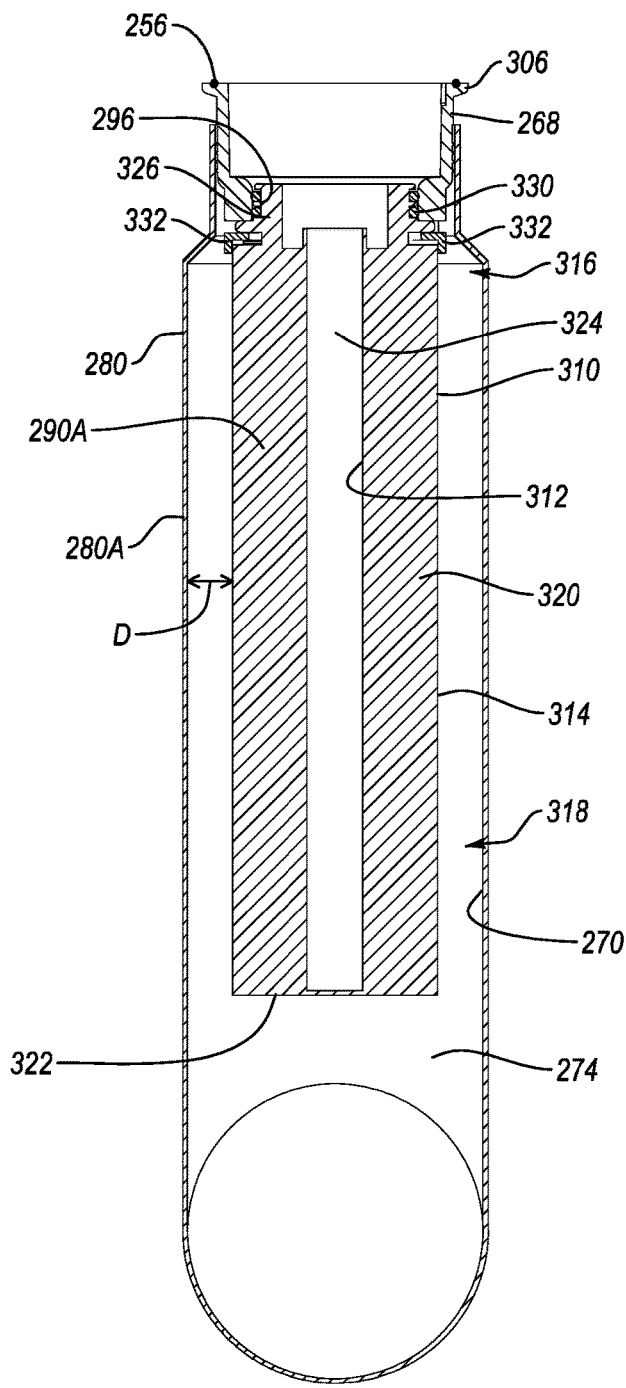
FIG. 17 is a cross sectional side view of the portion of the filter assembly shown in FIG. 15.

Returning to FIG. 15, disposed within each sleeve 280A-D of casing 264 is a corresponding filter 280A-D that is coupled with a corresponding exhaust port 268A-D. As depicted in FIGS. 16 and 17, filter 290A comprises a filter body 310 having an interior surface 312 and an exterior surface 314 extending between a first end 316 and an opposing second end 318. Filter body 310 includes a tubular side wall 320 that extends between opposing ends 316 and 318 and a floor 322 disposed at second end 318. As such, interior surface 312 bounds a blind channel 324 that centrally extends along the length of filter body 310 but which is blocked at second end 318 by floor 322. Upwardly projecting from first end 316 of filter body 310 is a tubular neck 326. A pair of annular grooves 328A and B encircle the exterior surface of neck 326 and are configured to receive corresponding annular seals 330A and B. Also outwardly projecting from the exterior surface of neck 326 at a location below grooves 328A and B are a pair of opposing bayonet prongs 332. An opening 324 extends through neck 326 and communicates with channel 324.

In one embodiment, filter body 310 is made of a porous material through which gas can pass but through which unwanted contaminants, such as bacteria and microorganisms, cannot. The porous material is typically hydrophobic which helps it to repel liquids. For example, filter body 310 can be comprised of polyvinylidene fluoride (PVDF). Other materials can also be used. Where the system is acting as a bioreactor or fermentor, filter body 310 typically needs to operate as a sterilizing filter and will thus typically have a pore size of 0.22 micometers ($\mu$m) or smaller. The term "pore size" is defined as the largest pore in the material through which a particle can pass. Commonly, filter body 310 has a pore size in a range between 0.22 and 0.18 $\mu$m. However, for pre-filtering applications or for non-sterile applications, filter body 310 can have a larger pore size, such as in a range between about 0.3 and 1.0 $\mu$m. In still other applications, the pore size can be greater than 1.0 $\mu$m or smaller than 1.0 $\mu$m. One example of filter body 310 is the DURAPORE 0.22 $\mu$m hydrophobic cartridge filter produced by Millipore. Another example is the PUREFLO UE cartridge filter available from ZenPure.

During assembly, seals 330 are received within annular grooves 328 following which neck 326 of filter 290A is coupled to exhaust port 268 by bayonet prongs 332 being received and rotated within bayonet slots 304. In this configuration, filter 290A is securely attached to exhaust port 268A with seals 330 forming a gas tight seal between neck 326 and interior surface 296 of exhaust port 268A. Next, filter 290A is slid within sleeve 280A of casing 264 so that exhaust port 268A is partially received within sleeve 280A. A gas tight seal is then formed between sleeve 280A and exhaust port 268A such as by welding sleeve 280A to exterior surface 290 of stem 294. Filters 290B-D have the same configuration as filter 290A and the same process can be used for attaching filters 290B-D to exhaust ports 268B-D and then securing filters 290B-D within sleeves 280B-D of casing 264. During use, as discussed below in more detail, gas from condenser bag 102 enters filter assembly 260 from intake port 266 but can only exit filter assembly 260 by passing through a corresponding filter body 310, traveling along channel 324 and then exiting out through a corresponding exhaust port 268A-D. As such, filters 290 sterilize or otherwise filter all gas passing out of filter assembly 260. Likewise, the only way gas and other matter from the outside environment can enter filter assembly 260 is through filters 290. As such, filters 290 also function as sterilizing filters that prevent outside contaminates from accessing the compartment of filter assembly 260 which could then potentially contact the fluid within container 12.

Filter assembly 260 is designed to be capable of filtering high flow rates of gas. Specifically, as gas enters filter assembly 260, flexible casing 264 expands to the configuration shown in FIGS. 15 and 17. In the expanded configuration, each sleeve 280 is spaced apart from exterior surface 314 of each corresponding filter body 310 along the length of filter body 310. As such, the gas can freely access and pass through filter body 310 from all sides and along the full length of filter body 310, thereby optimizing the use of filter body 310 and maximizing the gas flow rate therethrough. In one embodiment, the annular gap distance D between exterior surface 314 of filter body 310 and the interior surface of the corresponding sleeve 280 is in a range between about 0.15 cm to about 3 cm with about 0.2 cm to about 1 cm being more common. In some embodiments, the gap distance D can be greater than 1 cm or 2 cm. Other dimensions can also be used. In one embodiment filter body 310 has a maximum transverse diameter in a range between about 5 cm and about 10 Other dimensions can also be used. Furthermore, gap distance D typically extends over at least 80% and more commonly at least 90%, 95% or 100% of the length of filter body 310. Filter assembly 260 can also process a high gas flow rate because the port openings of intake port 266 and exhaust port 268 can be designed having a surprising large diameter, such as greater than 3 cm, 4 cm, 5 cm or 6 cm, and because filter assembly 260 can be designed to simultaneous operate with a plurality of filters 290 that are disposed in parallel communication with the gas flow.

Figure 17A:
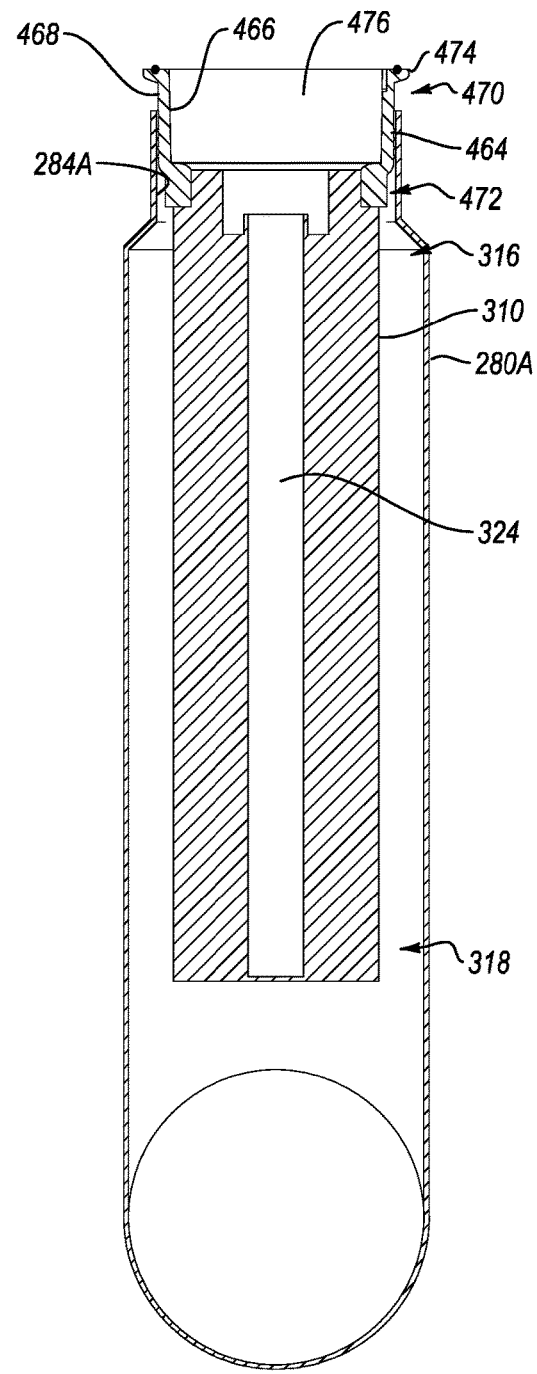
FIG. 17A is a cross sectional side view of an alternative embodiment of the portion of the filter assembly shown in FIG. 17.

In an alternative embodiment, the filter and exhaust port can be formed as a single piece. For example, depicted in FIG. 17A is a filter 460. Like elements between filter 460 and previously discussed filter 290 are identified by like reference characters. Filter 460 includes filter body 310 which has the same structure, composition and properties as previously discussed. However, rather than including neck 326 at first end 316, filter 460 includes an exhaust port 462 that is permanently fixed to first end 316 of filter body 310 such as by over molding, adhesive, welding, or the like. As such, no separate seal is needed between exhaust port 462 and filter body 310. Exhaust port 462 includes a stem 464 having an interior surface 466 and an opposing exterior surface 466 that extend between a first end 470 and an opposing second end 472. Second end 472 is secured to filter body 310 as discussed above. Encircling and outwardly projecting from first end 470 is a flange 474. Interior surface 466 bounds a port opening 476 that extends therethrough and communicates with channel 324 of filter body 310. Filter body 310 is received within sleeve 280A and exterior surface 466 of exhaust port 462 is received within outlet opening 284A of sleeve 280A. Exterior surface 466 is sealed to sleeve 280A, such as by welding, so as to form a gas tight seal. Exhaust port 462 is typically comprised of a non-porous polymeric material while filter body 310 is comprised of a porous material, as previously discussed. In another embodiment, it is envisioned that exhaust port 462 could be eliminated and that sleeve 280A could be welded or otherwise secured directly to first end 316 of filter body 310.

Continuing with FIG. 16, as will be discussed below in greater detail, to assist in integrity testing of filters 290 following use, disposed at first end 282 of each sleeve 280 or on manifold 278 adjacent to first end 282 is a port 350 that communicates with compartment 274. A fill line 352, such as a flexible tube, has a first end 354 connected to port 350 and an opposing second end 356 having a connector 358 secured thereto. Connector 358 can be a lure lock connector or any other type of connector which can connect to a gas source for delivering a gas through fill line 352 to compartment 274. A clamp 360, such as a tube clamp, is disposed on fill line 352. Clamp 360 seals fill line 352 closed prior to use so that contaminates cannot enter compartment 274 through fill line 352. To eliminate clamps 360, connector 358 can be a type of connector that is sealed closed prior to use. For example, a sterile connector can be used.

In some embodiments, the distance between intake port 266 and each filter 290, measured along the path at which the gas flows, is at least 4 cm and more commonly at least 8 cm, 12 cm or 16 cm. Other dimensions can also be used. This spacing adds minimal cost because it is formed by casing 264 and adds the benefit of increasing filter life because there is more space for liquid to condense from the gas before it reaches filters 290. The spacing also provides area for seaming casing 264 closed for the purpose of integrity testing, as discussed below.

As also depicted in FIG. 16, each heating jacket 262 includes an insulation pad 340 that can be wrapped into a cylindrical loop and held in the desired configuration by straps 342 that encircle the exterior of pad 340. Disposed either within pad 340 or on the interior surface thereof is electrical heating tape 344. A hanger 346 can also project from the upper end of pad 340 by connecting to either pad 340 or straps 342. During use, each heating jacket 262 is wrapped around a corresponding sleeve 280. Jackets 262, however, are sized so that sleeves 280 can still inflate to provide the desired gap between filters 290 and sleeves 280 but are also typically configured so that sleeves 280 push against the interior surface of heating jackets 264 to produce an efficient heat transfer therebetween. Moisture that passes out of condenser bag 102 and into filter assembly 260 will collect on filters 290 and eventually clog the filters. By activating heat tape 344, heating jackets 264 assist to heat and vaporize the condensed liquid on filters 290 so that it can pass through and out of filters 290, thereby prolonging the active life of filters 290.

As depicted in FIG. 14, filter system 17 is supported by a rack assembly 386. Rack assembly 386 includes a pole 388 having a first end 390 and an opposing second end 392. First end 390 is slidably received within a retainer 394 that is secured on mount 154. Retainer 394 is configured to permit pole 398 to be raised and lowered to a desired position relative to condenser 100 and then releasably lock pole 398 in place when it is at its desired position. In the depicted embodiment, retainer 394 comprises a clamp having a body 395 secured on mount 154 with a passage extending therethrough in which pole 388 is slidably received. A cam arm 396 is rotatably mounted on body 395 and is configured to press against pole 388 within the opening. Clamp arm 396 moves between a raised first position where pole 388 can be raised and lowered and a lowered second position, as depicted, where clamp arm 396 cams against pole 388 to lock it in place. It is appreciated that retainer 394 can comprise a variety of other types of clamps or retainers to adjustably secure pole 388.

Mounted on second end 392 of pole 388 is a rack 398. Rack 398 includes a frame 400 having a first end mounted to pole 388 and an opposing second end having a plurality of spaced apart catches 402A-D formed thereat. Each catch 402 has a U-shaped slot 403 formed thereon. Slots 403 are configured so that second end 302 of stem 294 (FIG. 16) of each exhaust port 268 can be snugly received within a corresponding slot 403 so that flange 306 is supported on the top surface of each catch 402. As a result, exhaust ports 268 are securely retained on rack 398. With exhaust ports 268 secured to rack 398 while intake port 266 is secured to exhaust port 168 of condenser bag 102, raising and lowering pole 388 enables filter assembly 260 to be expanded to its desired height so that when gas is passed therethrough, casing 264 is inflated to its desired configuration. For example, if casing 264 is not fully expanded by rack assembly 386, casing 264 can buckle when inflated and push against filters 290, thereby decreasing filter performance.

In the above assembled configuration, filter assembly 260 is disposed vertically above and in alignment with condenser bag 102 and is otherwise configured so that any liquid that condenses within casing 264 can naturally flow under the force of gravity from filter assembly 260 and into condenser bag 102 by passing through intake port 266 and exhaust port 168. Removing condensed liquid from filter assembly 260 helps to preserve the operating life of filters 290. In one embodiment, during use exhaust port 168 of condenser bag 102, which is coupled with filter assembly 260, can have a central longitudinal axis that projects vertically or projects at an angle in a range between 0° and 20° and more common between 0° and 10° relative to vertical.

Figure 14A:
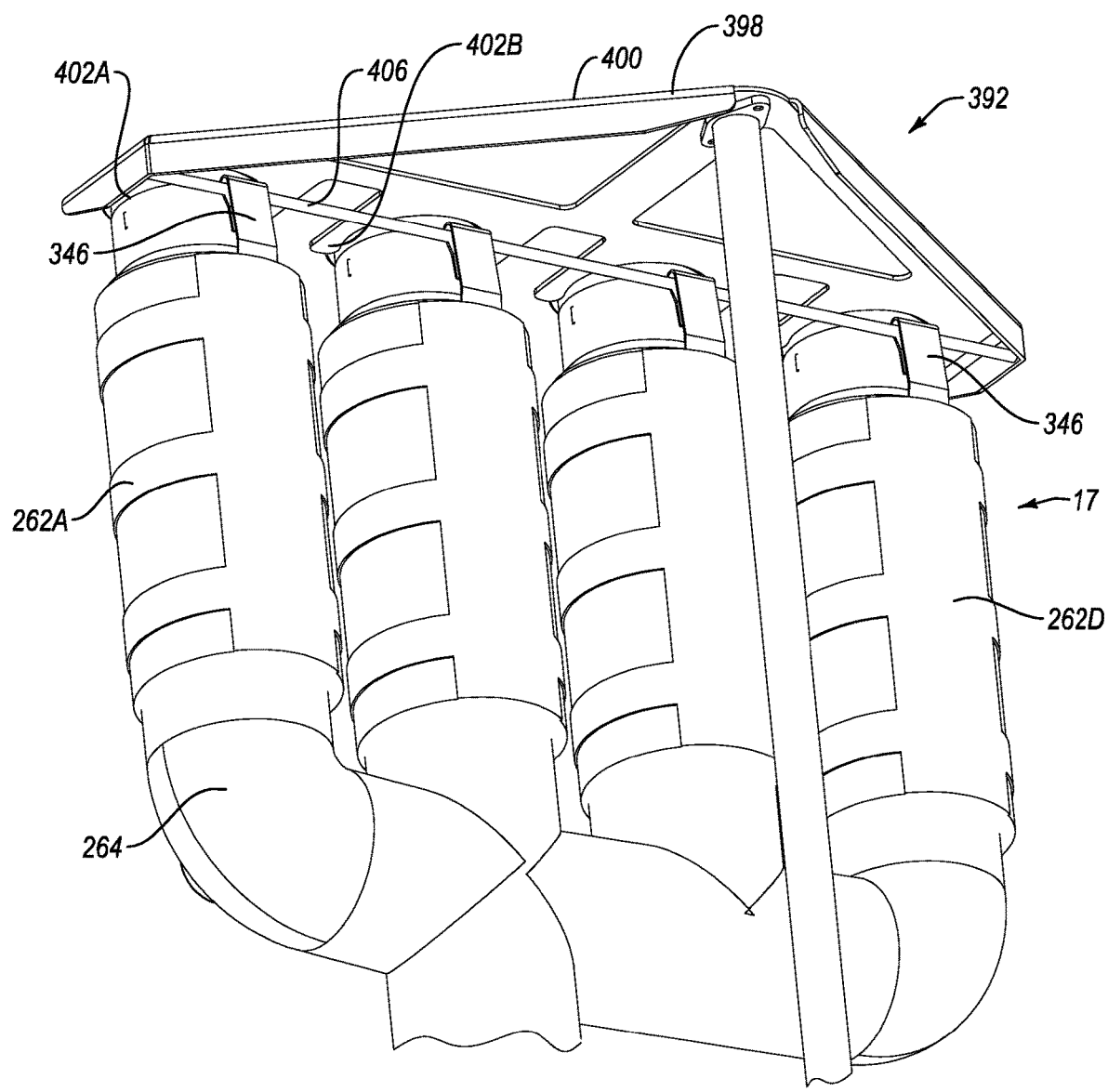
FIG. 14A is a bottom perspective view of the filter system shown in FIG. 14.

As depicted in FIG. 14A, a tie rod 406 can be secured on the bottom side of frame 400 so as to extend adjacent to each catch 402. Hangers 346 of each heating jacket 262 can be secured to tie rod 406. As a result, the weight of each heating jacket 262 is primary supported by rack 398 as opposed to casing 264. Furthermore, the use of tie rod 406 ensures that heating jackets 262 are always properly positioned relative to casing 264. It is appreciated that heating jackets 262 can be secured to rack 398 using a variety of other techniques and structures.

During assembly, intake port 166 of condenser bag 102 is coupled with exhaust port 92 on container 12 while intake port 266 of filter assembly 260 is coupled with exhaust port 168 of condenser bag 102, as previously discussed. The connected container 12, condenser bag 102 and filter assembly 260 can then be concurrently sterilized, such as by radiation, so that the compartments therein are sterilized. The assembled system can then be shipped for use. During use, container 12 is received within support housing 14, condenser bag 102 is secured to condenser 100, and filter assembly 260 is mounted on rack assembly 386 and adjusted, as previously discussed. In this assembled state, the sparged gas from container 12 passes into condenser bag 102. The dehumidified gas from condenser bag 102 then passes into filter assembly 260 where it exits out to the environment through filters 290.

Filter assembly 260, used either independently or in conjunction with container 12 and/or condenser bag 102, has a number of unique benefits. For example, because casing 264 of filter assembly 260 is made from polymeric film, as opposed to being a metal container or rigid plastic housing, filter assembly 260 is relatively simple and inexpensive to produce. As such, filter assembly 260 is a single use item that can be disposed of or recycled after a single use, thereby avoiding any need for cleaning or sterilization.

Because container 12, condenser bag 102 and filter assembly 260 are each comprised of a polymeric film which is used to contain the gas being exhausted, fluid processing system 10 is typically designed to operate at a relatively low gas pressure. That is, processing system 10 is typically configured so that during operation container 12, condenser bag 102 and/or filter assembly 260 operate at an internal gas pressure of under 10 kPa and typically in a range between about 0 kPa to about 8 kPa with about 2 kPa to about 5 kPa being more preferred. Furthermore, container 12, condenser bag 102 and/or filter assembly 260 can be designed to fail by rupture of the polymeric film or seams formed on the polymeric film when they are subject to an internal gas pressure of 50 kPa or more commonly 60 kPa or 70 kPa.

To optimize operation at low gas pressures, processing system 10 can be designed so that the only back pressure produced in the gas flow path extending from container 12 through filter assembly 260 is caused by the gas passing through filter(s) 290. For example, some traditional bioreactor systems include a rigid reactor container, a rigid condenser system and a rigid filter system through which the gas passes. These rigid components are designed so that they can safely operate at relatively high gas pressures, such as around 500 kPa. The traditional rigid components are typically fitted with small diameter gas inlet ports and gas outlet ports, i.e., circular ports having a maximum inside diameter that is commonly less than 2 cm. When high gas flow rates are processed through these conventional systems, each of the gas intake ports and exhaust ports forms a gas restriction point that causes back pressure. Traditional systems use small diameter ports because the amount of back pressure produced is minimal relative to the pressure that can be safely handled by the rigid components and because small diameter ports are less expensive and more standard in the industry. In one embodiment of the present invention, however, each of the gas intake ports and the gas exhaust ports for container 12, condenser bag 102 and filter assembly 260 are formed having a diameter or area that is sufficiently large so that no back pressure is produced as the gas passes therethrough. For low gas flow rates, such ports can be relatively small. For high gas flow rates, however, such as, for example, flow rates greater than 300 slpm or 500 slpm, the gas intake ports and the gas exhaust ports for each of container 12, condenser bag 102 and filter assembly 260 can be formed having a maximum inside diameter that is greater than 3 cm and more commonly greater than 4 cm, 5 cm, 6 cm or 10 cm. The use of such sized ports is unique in the field of bioreactors and fermenters. It is understood that the larger ports can be used at lower gas flow rates or that smaller ports can be used at lower gas flow rates.

An additional benefit to using large diameter ports through which the gas passes is that the ports minimize the speed at which the gas passes through the ports. As previously mentioned, one of the intended benefits of one embodiment of the present invention is that if any moisture from the gas condenses within filter assembly 260, the condensed liquid is free to flow under the force of gravity down through intake port 266 and into condenser bag 102. However, if exhaust port 168 or intake port 266 are too small, the velocity of the gas passing therethrough can be substantially increased. The high velocity gas can both preclude condensed liquid from flowing under gravity from filter assembly 260 into condenser bag 102 and can force liquid that has condensed within condenser bag 102 adjacent to intake port 266 to flow into filter assembly 260. Fluid collecting within filter assembly 260 can eventually contact and occlude filters 290, thereby requiring the use of more filters. In view of the foregoing, using large diameter ports in the present system enables the system to handle large gas flow rates with minimal back pressure so as to avoid the risk of rupturing the polymeric film and enables fluid to freely flow out of filter assembly 260 and into condenser bag 102 or container 12 so as to extend the life of filters 290.

The gap distance D between filters 290 and sleeves 280, as previously discussed, can also be selected to preclude or minimize back pressure. For example, with reference to a transverse cross section normal to the longitudinal axis of filter 290 and extending through filter 290 and sleeve 280, the area of the cross section within the gap region that encircles filter 290 (hereinafter "the gap area") can be sufficiently large at all points along the length of filter 290 or over a select length of filter 290 so that no additional back pressure in created as a result of the gas passing along the gap area. Rather, the back pressure is produced solely or substantially by the gas passing through filter 290. To achieve the foregoing, in one embodiment the gap area is in a range equal to the area of gas intake port 266 or gas exhaust port 168+/−10%, 15% or 20%. It is appreciated that it is not critical that the only back pressure be produced by gas passing through filter 290. A small amount of back pressure can also be produced by gas passing through the intake ports, exhaust ports and/or through the gap area as long as the back pressure is not so great that it risks the safe operation of container 12, condenser bag 102 or filter assembly 260.

Select embodiments of filter assembly 260 and other components also have other benefits. For example, because filter assembly 260 is coupled directly to condenser bag 102, as opposed to being coupled with tubing, material costs and assembly time is reduced. Likewise, because both condenser bag 102 and filter assembly 260 are mounted to support housing, the system has a relative small footprint that occupies minimal space. Furthermore, by keeping the elevation of condenser system 16 relatively low, the maximum height of filter assembly 260 is minimized, thereby enabling use in low ceiling areas. The fluid processing system can operate under a large range of gas flow rates, thereby permitting the processing of a variety of different types of fluid. The system is particularly adapted for functioning as a fermenter that processes microorganisms due to the high gas flow rate required to grow microorganisms. Furthermore, because the system operates at a relatively low gas pressure, a less rigid containment structure is required and the system is safer to work around. The system and the components thereof also have other advantages.

In the depicted embodiment, filter assembly 260 includes four sleeves 280A-D and four corresponding filters 290A-D.

Figure 18:
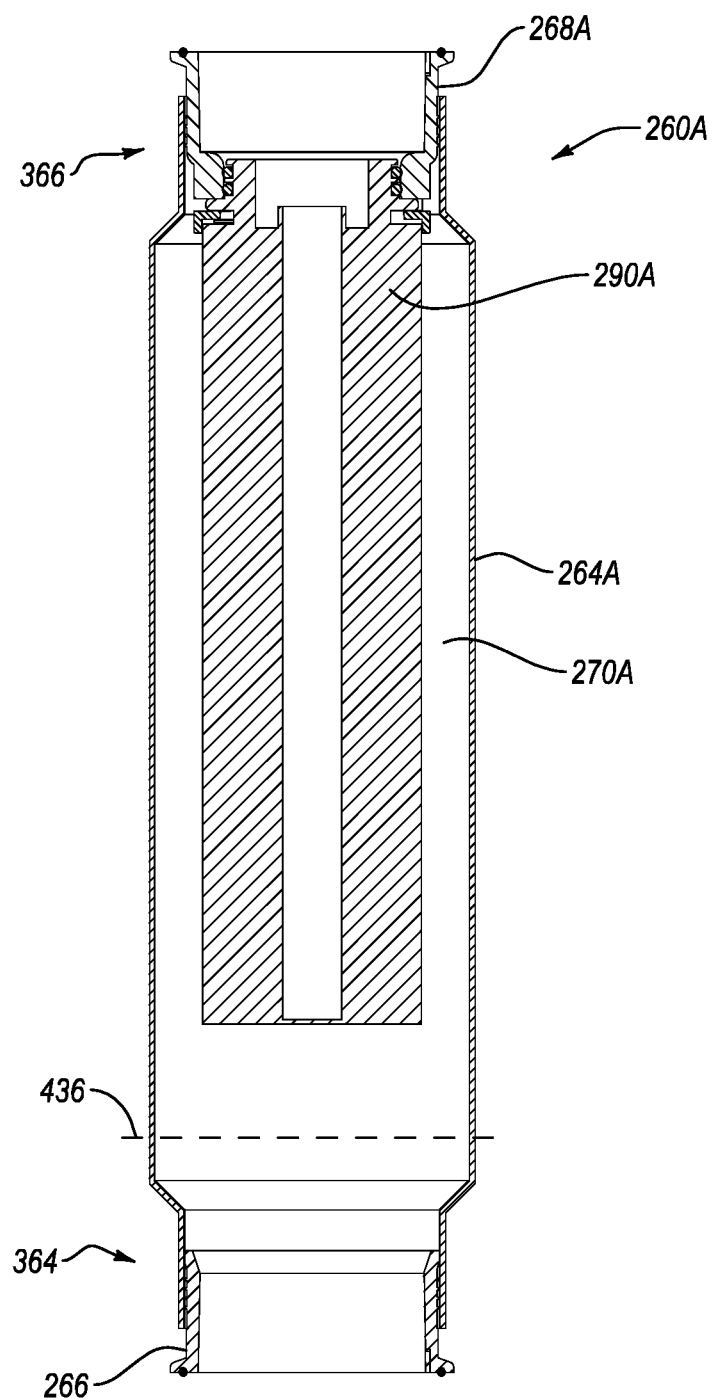
FIG. 18 is a cross sectional side view of an alternative embodiment of the filter assembly shown in FIG. 15 that includes a single filter.

The number of filters 290 used is largely dependent on the volume of culture or other fluid being processed. In alternative embodiments, filter assembly 260 can comprise one sleeve 280, two sleeves 280, three sleeves 280, or five or more sleeves 280 along with a corresponding number of filters 290. For example, depicted in FIG. 18 is an alternative embodiment of a filter assembly 260A that includes a single filter. Like features between filter assemblies 260 and 260A are identified by like reference characters. Filter assembly 260A includes a casing 264A in the form of an elongated linear tubular sleeve that bounds a compartment 270A extending between a first end 364 and an opposing second end 366. Casing 264A can be made from the same materials, such as polymeric films, and have the same properties as discussed above with regard to casing 264. Intake port 266 is secured to first end 364 while exhaust port 268A is secured to second end 366. Filter 290A is secured to exhaust port 268A and is disposed within compartment 270A in the same manner so as to operate in the same way as discussed above with regard to filter 290A in sleeve 280A (FIG. 17). Fill line 352 can be mounted on casing 264A so as to communicate with compartment 270A.

Figure 19:
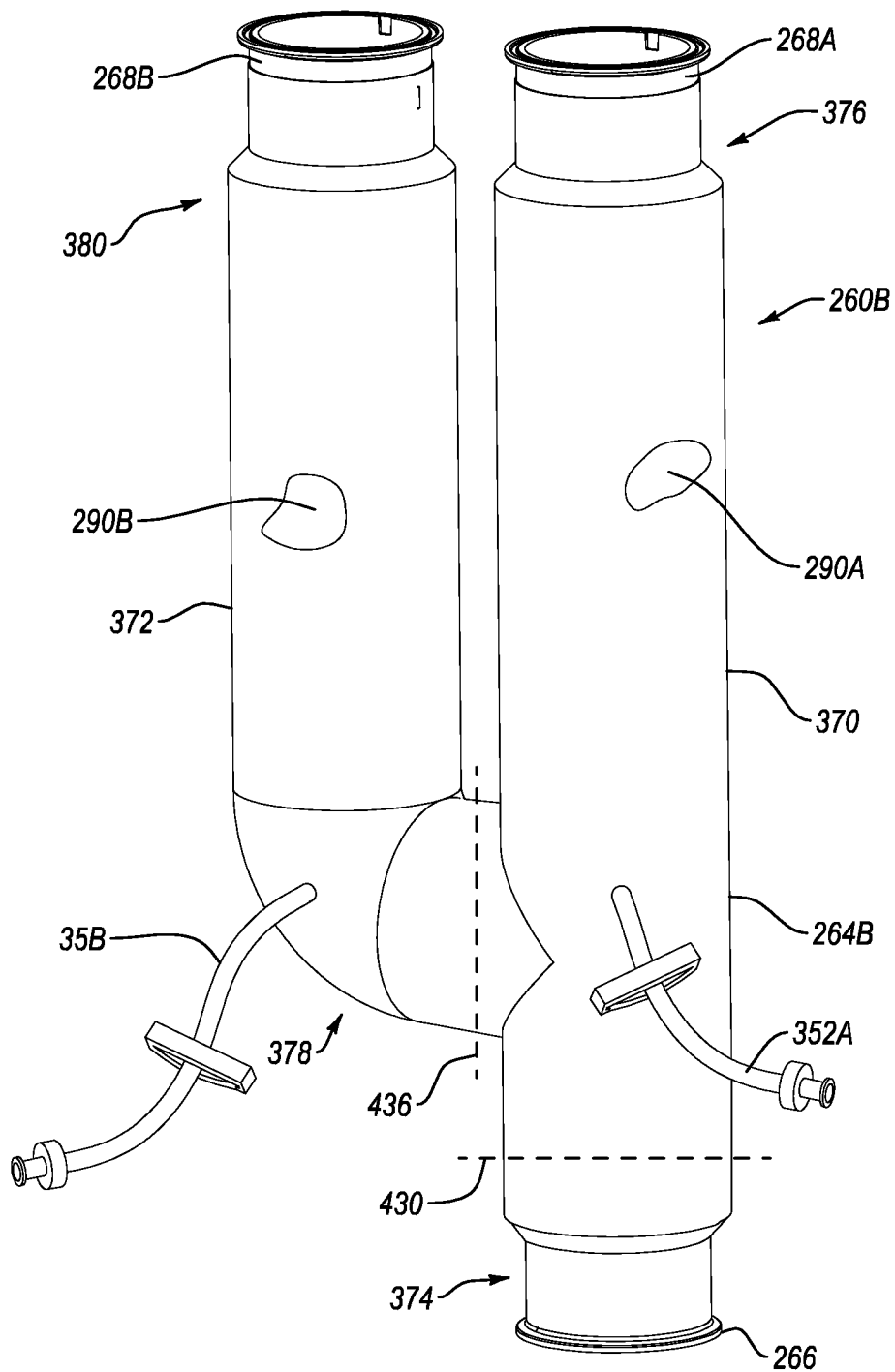
FIG. 19 is a perspective view of an alternative embodiment of the filter assembly shown in FIG. 15 that includes two filters.

Depicted in FIG. 19 is another alternative embodiment of a filter assembly 260B that includes two filters. Like features between filter assemblies 260 and 260B are identified by like reference characters. Filter assembly 260B includes a casing 264B that bounds a compartment 270B. Casing 264B can be made from the same materials, such as polymeric films, and have the same properties as discussed above with regard to casing 264. Casing 264B includes a tubular first sleeve 370 and a tubular second sleeve 372. First sleeve 370 is linear and extends between a first end 374 and an opposing second end 376. Intake port 266 is secured to first end 374 while exhaust port 268A is secured to second end 376. Filter 290A is secured to exhaust port 268A and is disposed within sleeve 370 in the same manner so as to operate in the same way as discussed above with regard to filter 290A in sleeve 280A (FIG. 17). Second sleeve 372 includes a first end 378 and an opposing second end 380. First end 378 has an L-shaped curve that couples in fluid communication with first sleeve 370 at a location between the bottom of filter 290A and intake port 266. Exhaust port 268B is secured to second end 380. Filter 290B is secured to exhaust port 268B and is disposed within second sleeve 372 in the same manner so as to operate in the same way as discussed above with regard to filter 290A in sleeve 280A (FIG. 17). Fill lines 352A and B can be mounted on sleeves 370 and 372 so as to communicate with the corresponding compartment sections. A filter assembly with three filters can be formed by securing a third sleeve, identical to second sleeve 372, on the opposing side of first sleeve 370 and securing exhaust port 268C and filter 290C thereto.

Figure 20:
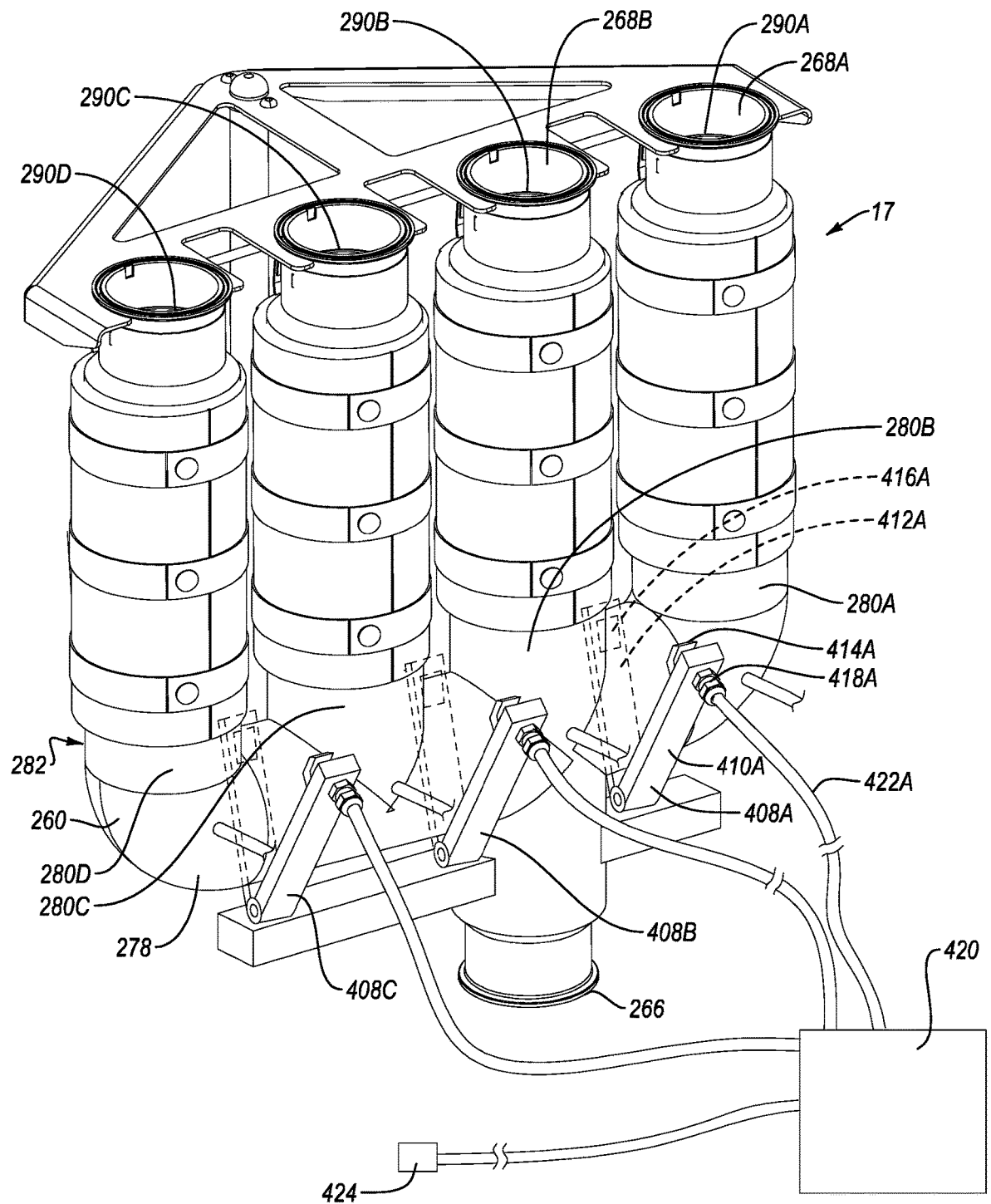
FIG. 20 is a perspective view of the filter system shown in FIG. 14 having an automated clamping system coupled thereto.

In the above discussed embodiments, the filter assemblies can operate so that gas is concurrently exiting out of each filter 290 during operation. In an alternative embodiment, one or more clamps can be used to isolate one or more filters 290 from the gas flow. When the filter(s) in use begins to plug, the clamps can be released, either concurrently or in stages, to permit the gas to flow through the new filter(s). For example, depicted in FIG. 20, a plurality of clamps 408A-C can be mounted on filter assembly 260. Specifically, clamp 408A extends across manifold 278 between first sleeve 280A and second sleeve 280B; clamp 408B extends across manifold 278 between second sleeve 280B and third sleeve 280C; and clamp 408C extends across manifold 278 between third sleeve 280C and fourth sleeve 280D. Clamps 408 can be moved between a closed position that seals closed the section of manifold 278 over which the clamp extends so that gas cannot pass therethrough and an open position which permits the gas to freely pass through manifold 278. In one embodiment, clamps 408 can simply be clamps that are manually opened and closed.

During operation, gas is delivered to filter assembly 260 through intake port 266. The gas travels up through second sleeve 280B, through filter 290B and out through outlet port 268B. Clamps 408A and B preclude any of the gas from traveling out through filters 290A, C or D. As filter 290B starts to clog, the gas pressure within container 12, condenser bag 102 and filter assembly 260 starts to increase. This pressure can be measured by a pressure sensor that communicates with the head space in container 12. However, the pressure sensor could also be in communication with the gas at any location between container 12 and filter 290B.

As previously discussed, filter assembly 260 is designed to operate at a relatively low gas pressure. Accordingly, as the gas pressure increases, there is an increased risk that casing 264, condenser bag 102 and/or container 12 could fail due to rupture. Accordingly, when it is determined that the gas pressure has exceeded a predetermined value, either by sensing the gas pressure or otherwise determining the amount of clogging of filter 290B, clamp 408A can be opened, thereby decreasing the gas pressure by allowing at least a portion of the gas to now pass through filter 290A. The monitoring of the gas pressure is continued and when it again exceeds the predetermined value, clamp 408B is opened to again decrease the gas pressure by allowing the gas to now flow out through gas filter 290C. If needed, clamp 408C can be opened to permit gas to pass out through gas filter 290D.

As previously mentioned, clamps 408 can be manual clamps. As such, as the gas pressure increases, clamps 408A-C can be manually opened consecutively. Alternatively, clamps 408A-C can be configured to open automatically when the gas pressure exceeds the predetermined value. For example, in the depicted embodiment clamp 408A comprises a first arm 410A hingedly coupled to a second arm 412B. A barbed latch 414A is pivotably mounted on first arm 410 and is configured to engage and lock with second arm 412B by passing into an opening 416A on second arm 412A. That is, as latch 414A passes into opening 416, the barb on latch 414A catches on the back side of second arm 412 so as to lock arms 410A and 410B together. A solenoid 418A engages with latch 414A and selectively moves latch 414A between a catch position where latch 414A will engage with second arm 412A and a release position where latch 414A downwardly pivots to disengage from second arm 412A. Solenoid 418A is controlled by a central processing unit (CPU) 420 through an electrical wire 422A. Clamps 410B-D have the same configuration as clamp 410A and are operated in the same manner by being electrically coupled with CPU 420. CPU 420 is also electrically coupled with a pressure sensor 424 that is coupled with container 12 so as to detect the gas pressure within head space 162 of container 12 (FIG. 2).

Accordingly, during initial operation, each clamp 408A-C is in the closed position so that gas can only pass through filter 290B of sleeve 280B. When CPU determines that the gas pressure within container 12 exceed a predetermined value, CPU automatically moves latch 414A to the release position. The gas pressure within casing 264 forces clamp 408A to open and thereby allow gas to pass through filter 290A of sleeve 280A. CPU 420 can then consecutively automatically open clamps 408B and 408C, as needed, based on the level of gas pressure sensed in container 12 through pressure sensor 424.

As previously mentioned, sensor 424 can also communicate with condenser bag 102 or with filter assembly 260 so long as it is measuring, either directly or indirectly, the gas pressure to which container 12, condenser bag 102 and filter assembly 260 are being subjected. Furthermore, the clamps, whether manual or automatic, can have a variety of different configuration and methods of use. The clamps need only be able to clamp portions of casing 264 closed so that no gas can reach the restricted filters. The location of the clamps can also vary. For example, rather than placing clamps 408 on manifold 278, clamps 408 could be placed across first end 282 of each sleeve 280 below the corresponding filter 290. The same is also true for the alternative embodiments of the filter assembly having only two, three, or other numbers of filters.

By using the above clamping process to isolate the filters, only filters that are needed are used. It is desirable to limit the number of filters used because no integrity testing, as discussed below, is required for unused filters. Furthermore, because filters are relatively expensive, if a filter is unused it could potentially be recycled and used in a separate filter assembly.

Figure 21:
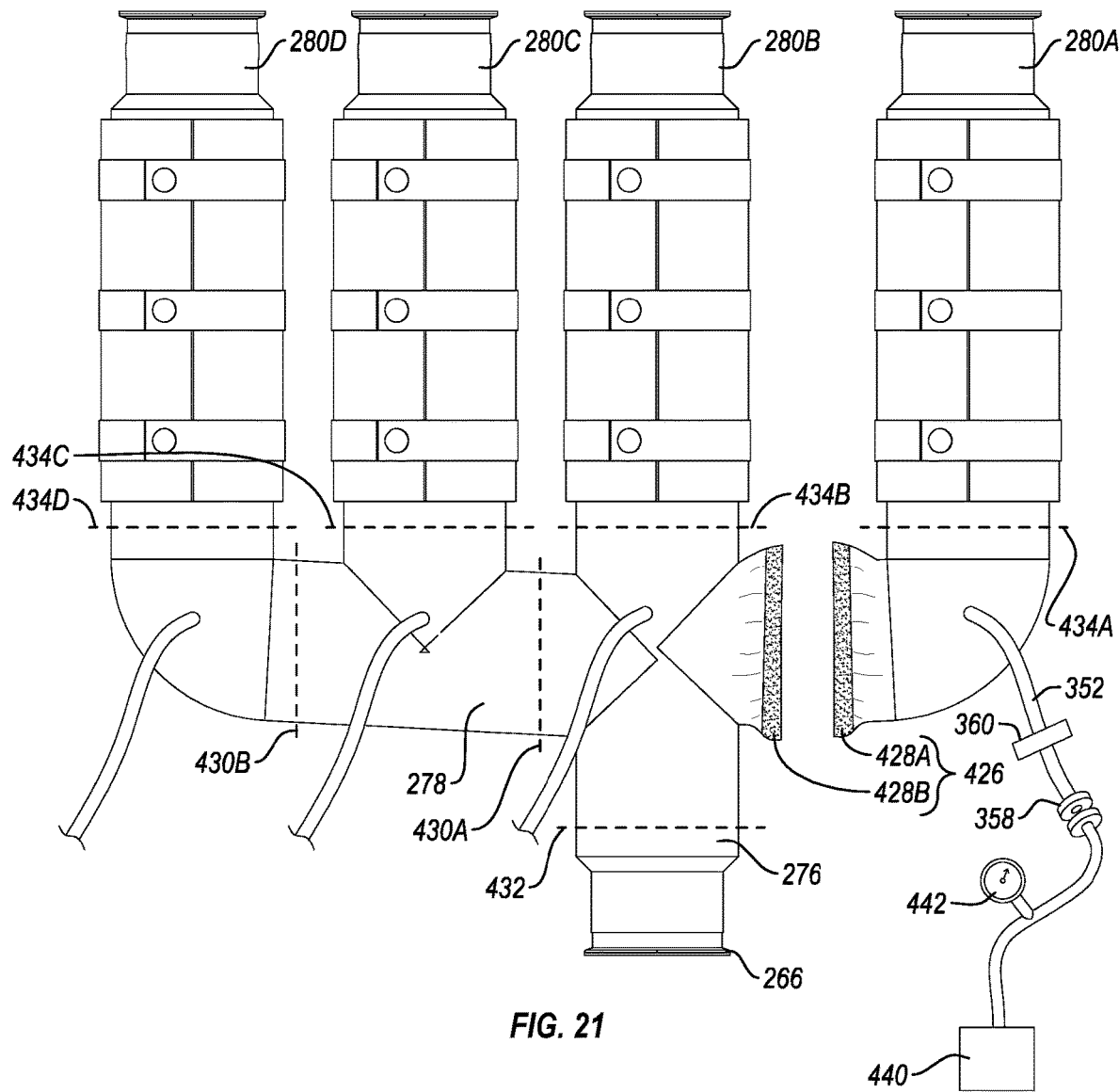
FIG. 21 is a perspective view of the filter system shown in FIG. 20 with a portion of the filter assembly being separated for integrity testing of the filter.

Following the processing of a culture, standard processing techniques require that filter(s) 290 be tested to ensure that the filters functioned properly so that no contaminates could have accessed the culture within container 12 through filter assembly 260. In one method of this integrity testing, each sleeve 280 with the corresponding filter 290 is separated from the remainder filter assembly 260. Specifically, as depicted in FIG. 21, a weld seam 426 is formed across manifold 278 between sleeves 280A and 280B so that no gas can pass though seam 426. Weld seam 426 is typically formed by compressing the opposing sides of manifold 278 together, which is formed by polymeric film, and then applying heat energies, RF energies, sonics, or other sealing energies across the compressed polymeric film, as is known in the art, so as to weld the film together.

Once seam 426 is formed, a cut is then centrally made along the length of seam 426 so as to separate sleeve 280A and corresponding filter 290A from the remainder of filter assembly 260. Specifically, seam 426 is bisected by the cut so that a portion 428A of seam 426 remains on the section of manifold 278 connected to sleeve 280A and a portion 428B of seam 426 remains on the section of manifold 278 connected to sleeve 280B. Both portions 428A and 428B of seam 426 independently form a gas tight seal across their corresponding section of manifold 278. Once sleeve 280A is removed, the integrity of filter 290A can be tested through a standard integrity testing method, such as through the bubble point test, diffusion test, pressure hold test or pressure decay test. For example, in one method clamp 360 is removed from fill line 352 and connector 358 is coupled with a gas source 440 that delivers a gas, such as air, and a component that will partially occlude the filter, such as ethanol. Next, the gas and the filter occluding component are delivered into the compartment bounded within sleeve 280A through fill line 352. The gas is delivered until a predetermined pressure is reached. The rate at which the filter occluding component passes through filter 290 can then be measured to determine the integrity of filter 290. Alternatively, the gas pressure can be monitored through a pressure gauge 442 for a predetermined period of time to determine if there is any loss in pressure or the rate of loss of pressure to determine the integrity of filter 290.

In another method, fill line 352 is used to fill the compartment of sleeve 280A with a detectable gas, such as helium, to a predetermined pressure. Either before or after dispensing the detectable gas, the separated sleeve 280A is enclosed within a sealed chamber of a detector and a vacuum is applied to the chamber. The detector then senses for the presence of the detectable gas within the chamber over a predetermined period of time to determine the integrity of filter 290. It is appreciated that the integrity tests are standard and known in the art and that other integrity tests can also be used.

In the same manner that sleeve 280A and filter 290A therein is tested, each of the remaining sleeves 280B-D and corresponding filters 290B-D can also be tested by forming weld seams along lines 430A and B. With regard to testing sleeve 280B and corresponding filter 290B, a gas tight cap can be connected to intake port 266 or a weld seam can be formed along line 432 across inlet 276. In alternative embodiments the weld seams can be placed at different locations. For example, by upwardly moving where each fill line 352 connects to a location higher on each sleeve 280A-D, the weld seams could be formed across the first end of each sleeve 280A-D below the corresponding fill line 352, such as along lines 434A-D. In the embodiments shown in FIGS. 18 and 19, the weld seam can be formed along lines 436 or at other locations consistent with the above discussion. Furthermore, in contrast to forming a single weld seam 426 and then bisecting the weld seam to separate the different sleeves, two spaced apart weld seams can be formed and casing 264 cut between the weld seams. Likewise, a single weld seam 426 can be replaced by clamps with casing 264 being cut between the clamps. Other techniques can also be used.

Figure 22:
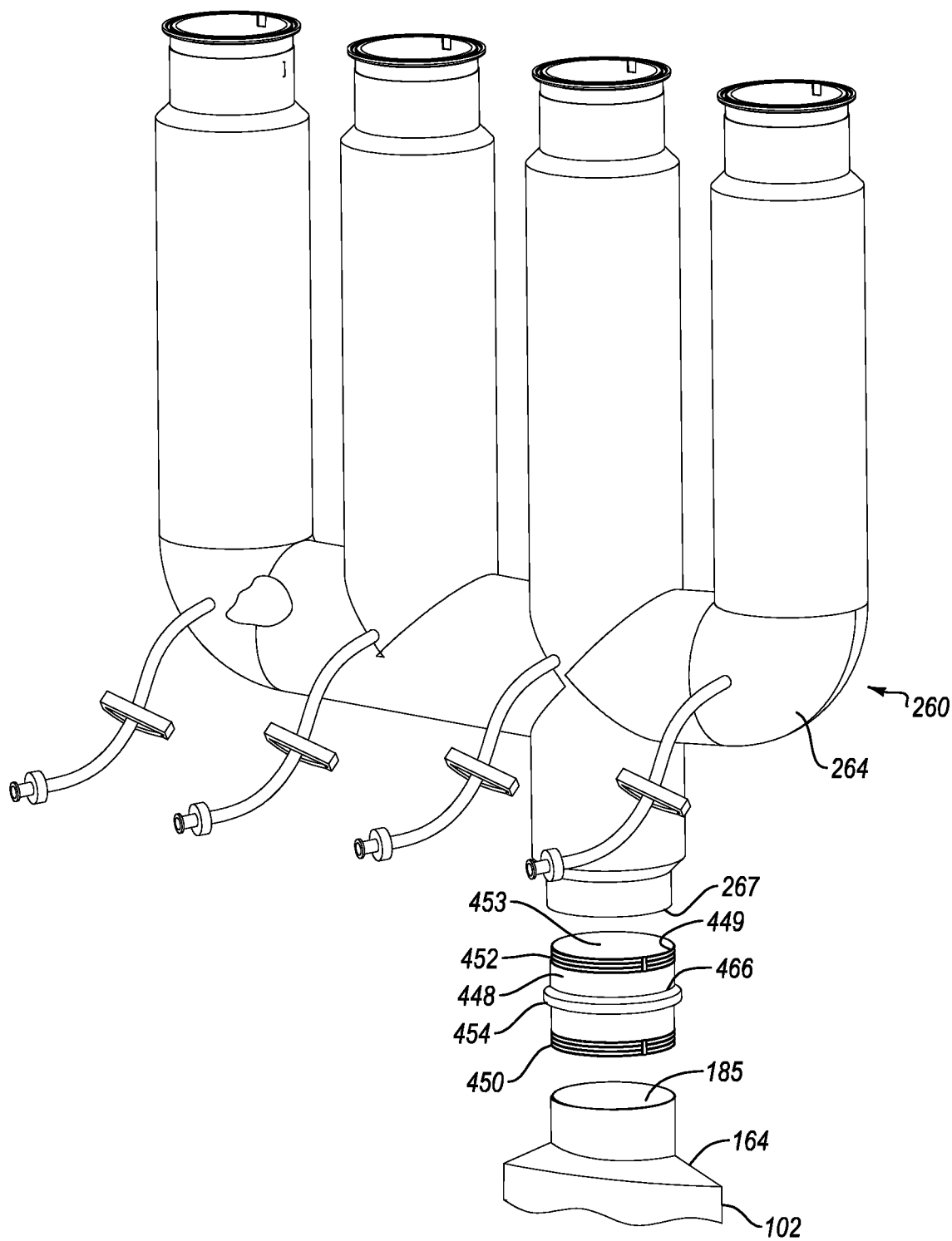
FIG. 22 is a perspective view of the filter assembly shown in FIG. 15 being coupled to the condenser bag by a single port.

In alternative embodiments, it is appreciated that filter assembly 260 can be connected to condenser bag using different techniques. For example, in FIG. 22 a single port 446 can be used to connect casing 264 of filter assembly 260 to body 164 of condenser bag 102. Port 446 includes an elongated stem 448 having an interior surface 449 and an exterior surface 452 that extend between a first end 450 and an opposing second end 452. Interior surface 449 bounds a port opening 453 that extends therethrough and that can have a size and configuration the same as the other port openings discussed herein. An optional alignment flange 454 encircles and radially outwardly projects from exterior surface 452 of stem 448 at a central location between opposing ends 450 and 452. First end 450 can be received and welded within outlet opening 185 of body 164 of condenser bag 102 while second end 452 can be received and welded within inlet opening 267 of body 264 of filter assembly 260. As a result, port 446 forms direct fluid communication between outlet opening 185 of condenser bag 102 and inlet opening 267 of filter assembly 260 without the use of a clamp.

Figure 23:
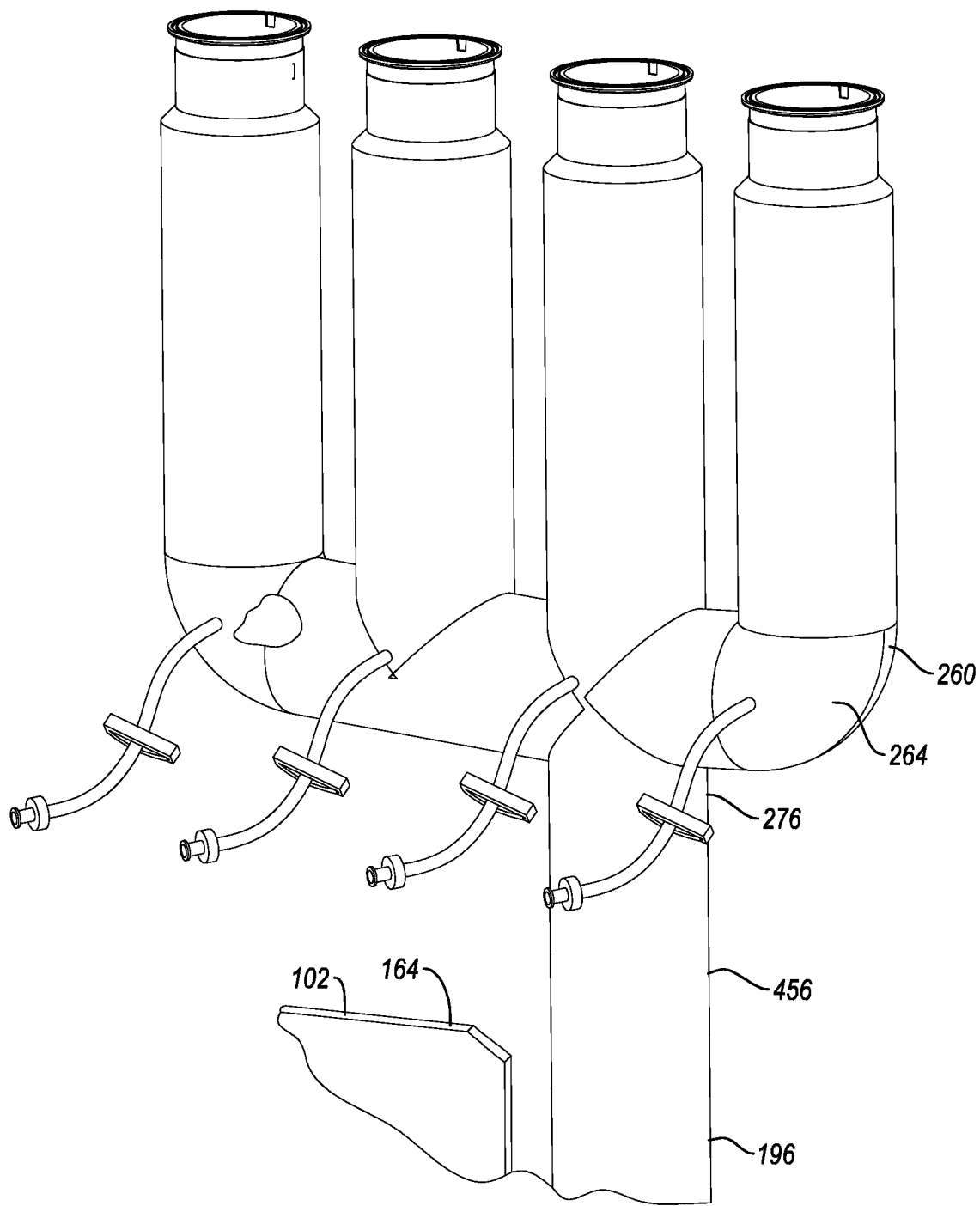
FIG. 23 is a perspective view of the filter assembly and condenser bag being integrally formed using a single continuous bag.

In another alternative embodiment as depicted in FIG. 23, body 164 of condenser bag 102 can be integrally formed with casing 264 of filter assembly 260 so that condenser bag 102 and filter assembly 260 are in fluid communication without the use of any clamp, port or other coupler. Specifically, as depicted in FIG. 23, third leg 196 of body 164 is integrally formed with inlet 276 of casing 264 so that third leg 196 and inlet 276 form a single continuous member 456. For example, body 164 and casing 264 can be formed as a single continuous pillow bag formed from two overlapping sheets of polymeric film that are welded together around their perimeter edge.

Figure 24:
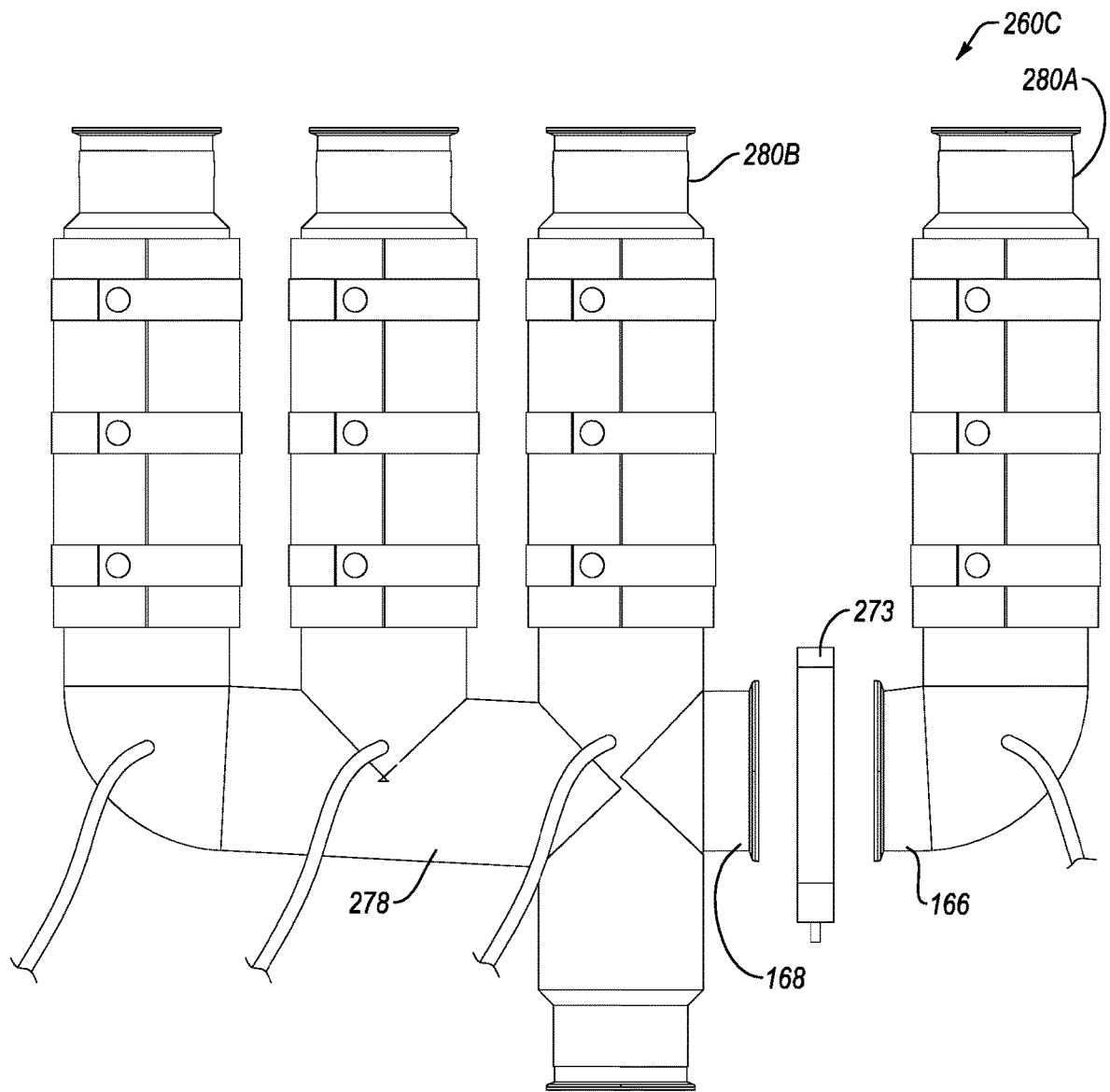
FIG. 24 is a perspective view of an alternative embodiment of a filter assembly that is modular.

Depicted in FIG. 24 is another alternative embodiment of a filter assembly 260C. Like elements between filter assembly 260 and 260C are identified by like reference characters. Filter assembly 260C is identical to filter assembly 260 except that it is modular in design. Specifically, manifold 278 between sleeves 280A and 280B is connected together by exhaust port 168 and intake port 266, previously discussed, that are mounted on opposing halves of the manifold section. Ports 168 and 266 can be coupled together using clamp 273 to form as gas tight seal therebetween as also previously discussed. By using ports 168 and 266 on manifold 278, any desired number sleeves 280 and filters 290 can be easily added to filter assembly 260C during the manufacture stage. For example, a separate pair of ports 168 and 266 can be formed along manifold 278 between each pair of sleeves 280. In this configuration, any desired number of single sleeves 280 and corresponding filters 290 can be sequentially added or removed in series, prior to sterilization, to form the desired filter assembly 260C.

Figure 25:
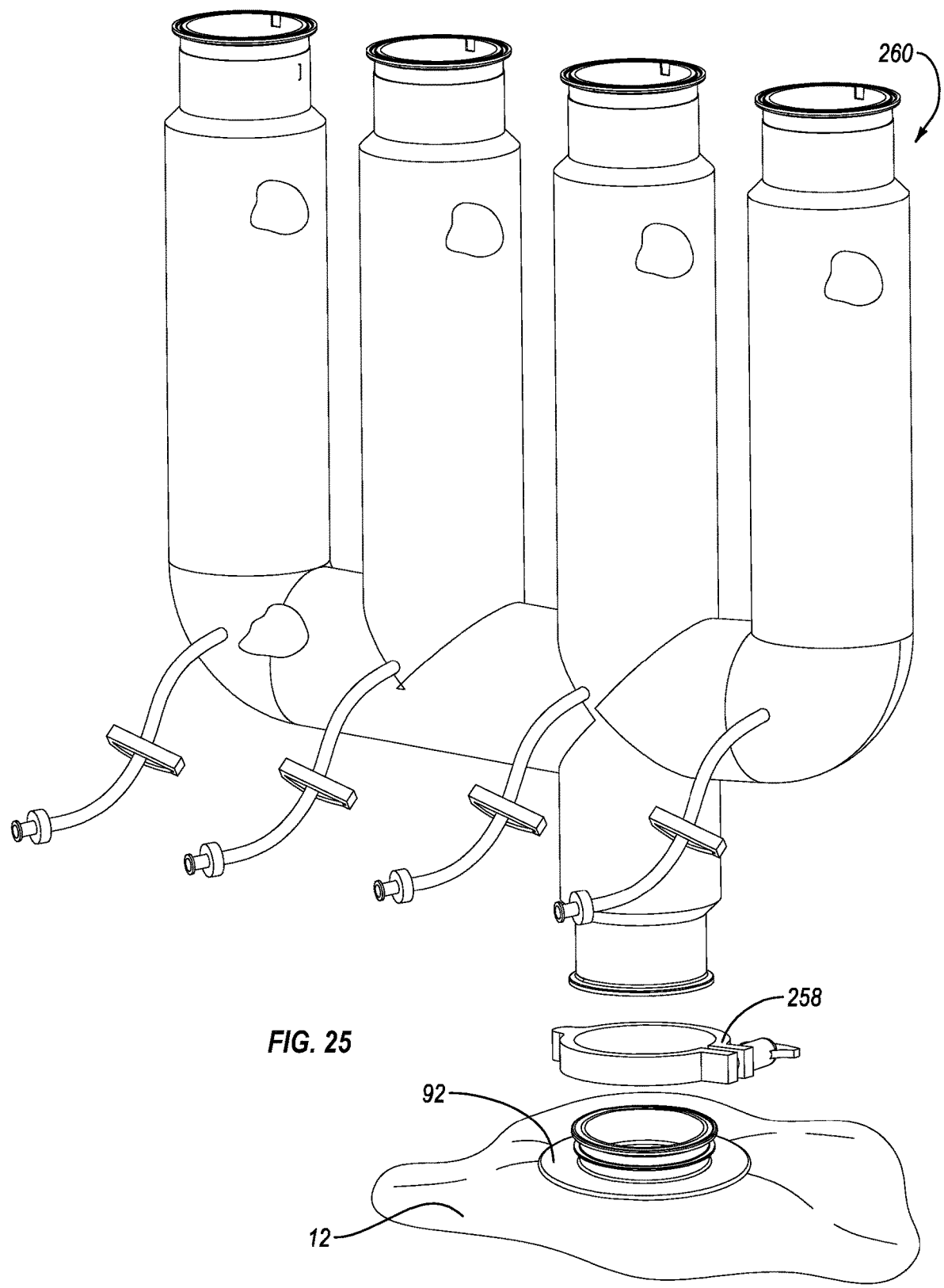
FIG. 25 is a perspective view of the filter assembly shown in FIG. 15 being directly coupled with the container in FIG. 1.

Finally, in the embodiments previously depicted herein, condenser bag 102 is coupled between container 12 and filter assembly 260. However, in an alternative use where the gas flow rate is very low so that only a minimal amount of moisture is being carried into condenser bag 102, condenser bag 102 and the remainder of condenser system 17 can be eliminated. According, as depicted in FIG. 25, filter assembly 260 and all of the other alternative filter assemblies discussed herein can be directly coupled to exhaust port 92 on container 12. Furthermore, alternative embodiments discussed herein of how condenser bag 102 can be secured to container 12, including the use of port 92A depicted in FIG. 13, are also applicable to how filter assemblies can be connected to container 12.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A condenser system comprising:
a collapsible container bag bounding a compartment and having an upper end and an opposing lower end, the container bag being comprised of a polymeric film and being adapted to hold a fluid, an exhaust port being physically secured to the upper end of the container bag;
a condenser bag comprising a body comprised of a polymeric film and bounding a channel that extends between a first end and an opposing second end, an inlet port being directly physically secured to the polymeric film at the first end of the body so as to communicate with the channel, and an exhaust port directly physically secured to the polymeric film at the second end of the body, the inlet port of the condenser bag being secured directly to the exhaust port on the collapsible container so that the first end of the condenser bag is fluid coupled with the upper end of the container bag; and
a tubular transfer line having a first end directly mechanically coupled with the condenser bag at a first location so as to communicate with the channel and an opposing second end directly mechanically coupled with the condenser bag at a second location located between the container bag and the first location so as to communicate with the channel, wherein the transfer line bounds a single, closed channel extending between the first end and the second end that does not fork.

2. The condenser system as recited in claim 1, wherein the first end of the condenser bag is removably coupled with the upper end of the container bag.

3. The condenser system as recited in claim 1, wherein the second end of the transfer line is directly mechanically coupled with the intake port so as to communicate with the channel.

4. The condenser system as recited in claim 1, wherein the second end of the transfer line is directly mechanically coupled with the body at a location spaced apart from the intake port so as to communicate with the channel.

5. The condenser system as recited in claim 1, wherein the condenser bag comprises a first leg connected to the container bag, a second leg, and an arm that extends between the first leg and the second leg, the first leg, second leg and arm forming a substantially U-shaped configuration with the channel passing therethrough, the second end of the transfer line being connected to the first leg.

6. The condenser system as recited in claim 5, wherein at least a portion of the first leg extends parallel to the second leg.

7. The condenser system as recited in claim 5, wherein the condenser bag further comprises a third leg, the portion of the channel bounded by and extended between the second leg and the third leg having a substantially U-shaped configuration.

8. The condenser system as recited in claim 7, wherein the first end of the transfer line is coupled with the second leg or the third leg.

9. The condenser system as recited in claim 7, wherein the condenser bag further comprises an extension projecting from the second leg or the third leg, the extension bounding a collection pocket that communicates with the channel, the first end of the transfer line coupling with the extension so as to communicate with the collection pocket.

10. The condenser system as recited in claim 1, wherein the channel of the condenser bag is sterile.

11. The condenser system as recited in claim 1, further comprising a pump coupled with the transfer line.

12. The condenser system as recited in claim 8, further comprising:
a condenser comprising a first panel and a second panel, the condenser bag being sandwiched between the first panel and the second panel; and
a chiller in fluid communication with at least the first panel or the second panel for cooling the temperature of the panel.

13. The condenser system as recited in claim 1, wherein the transfer line has a uniform transverse cross section at all locations between the first end the second end.

14. The condenser system as recited in claim 1, wherein the condenser bag is releasably secured directly to the exhaust port.

15. A condenser system comprising:
a support housing bounding a chamber;
a collapsible container bag bounding a compartment adapted to hold a fluid and being at least partially disposed within the chamber of the support housing, the container bag having an upper end and an opposing lower end and being comprised of a polymeric film;
a condenser coupled to the support housing so that at least a portion of the condenser is disposed at an elevation above the support housing; and
a condenser bag coupled to the condenser so that at least a portion of the condenser bag is disposed at an elevation above the container bag, the condenser bag comprising a body comprised of a polymeric film and bounding a channel that extends between a first end and an opposing second end, an inlet port being directly physically secured to the polymeric film at the first end of the body so as to communicate with the channel, and an exhaust port directly physically secured to the polymeric film at the second end of the body, the inlet port of the condenser bag being secured directly to the exhaust port on the collapsible container so that the first end of the condenser bag is fluid coupled with the upper end of the container bag.

16. The condenser system as recited in claim 15, wherein the condenser comprises a first panel and a second panel that are both at least partially disposed at an elevation above the support housing, the condenser bag being sandwiched between the first panel and the second panel.

17. The condenser system as recited in claim 16, wherein the support housing has an upper end that terminates at a terminal end face, at least a portion of the first panel and the second panel being disposed at an elevation above the terminal end face and at least a portion of the first panel and the second panel being disposed at an elevation below the terminal end face.

18. The condenser system as recited in claim 16, wherein no portion of the first panel or the second panel is disposed vertically above the chamber of the support housing.

19. The condenser system as recited in claim 16, further comprising a chiller in fluid communication with at least the first panel or the second panel for cooling the temperature of the panel.

20. The condenser system as recited in claim 15, wherein at least a portion of the condenser bag is disposed vertically above the container bag.

21. The condenser system as recited in claim 15, further comprising a sparger disposed at the lower end of the container bag for delivering a gas into the compartment of the container bag.

22. The condenser system as recited in claim 15, further comprising a filter assembly coupled with the condenser bag, the filter assembly comprising:
a casing comprised of a polymeric film and bounding a compartment, the casing having an inlet opening communicating with the channel of the condenser bag and having a first outlet opening, at least a portion of the casing being disposed at an elevation above the condenser bag; and
a first filter at least partially disposed within the compartment of the casing so that gas passing through the compartment of the casing from the inlet opening to the first outlet opening must pass through the filter.

23. A condenser system comprising:
a collapsible container bag bounding a compartment and having an upper end and an opposing lower end, the container bag being comprised of a polymeric film and being adapted to hold a fluid, an exhaust port being physically secured to the upper end of the container bag;
a condenser bag comprising a body comprised of a polymeric film and bounding a channel that extends between a first end and an opposing second end, an inlet port being directly physically secured to the polymeric film at the first end of the body so as to communicate with the channel, and an exhaust port directly physically secured to the polymeric film at the second end of the body, the inlet port of the condenser bag being releasably secured directly to the exhaust port on the collapsible container so that the first end of the condenser bag is fluid coupled with the upper end of the container bag;

a tubular transfer line having a first end directly mechanically coupled with the condenser bag at a first location so as to communicate with the channel and an opposing second end directly mechanically coupled with the condenser bag at a second location located between the container bag and the first location so as to communicate with the channel; and a pump secured to the transfer line so that activation of the pump transfers a liquid through the transfer line from the first end to the second end when the liquid is disposed within the condenser bag at the first location.

* * * * *